United States Patent
Wang et al.

(10) Patent No.: US 7,579,091 B2
(45) Date of Patent: Aug. 25, 2009

(54) WHITE ELECTROLUMINESCENT POLYMERIC MATERIAL AND PREPARATION THEREOF

(75) Inventors: Lixiang Wang, Changchun (CN); Guoli Tu, Changchun (CN); Jianxin Cao, Changchun (CN); Jun Liu, Changchun (CN); Dongge Ma, Changchun (CN); Xia Bin Jing, Changchun (CN); Fosong Wang, Changchun (CN)

(73) Assignee: Changchun Institute of Applied Chemistry Chinese Academy of Science, Changchun (CN)

( * ) Notice: Subject to any disclaimer, the term of this patent is extended or adjusted under 35 U.S.C. 154(b) by 255 days.

(21) Appl. No.: 11/042,193

(22) Filed: Jan. 26, 2005

(65) Prior Publication Data

US 2005/0214568 A1   Sep. 29, 2005

(30) Foreign Application Priority Data

Mar. 29, 2004   (CN) .................. 2004 1 0010770

(51) Int. Cl.
*B32B 19/00* (2006.01)
*C09K 11/06* (2006.01)

(52) U.S. Cl. .................. 428/690; 428/917; 528/480; 528/424; 528/423; 528/422; 528/373

(58) Field of Classification Search .................. 428/690, 428/917; 528/480, 424, 423, 422, 373
See application file for complete search history.

(56) References Cited

U.S. PATENT DOCUMENTS 6,555,840 B1 * 4/2003 Hudson et al. .................. 257/40

OTHER PUBLICATIONS

Claim 1 with (A) species of U.S. Appl. No. 11/779,101.*
Wang et al; Energy transfer—and preparation; 2003; Changchun Institute of applied chemistry, Chinese Acadamy of sciences, Peop. Rep. China; Chem Abstracts 140: 171903 and 140: 171902.*
Burroughes et al., Nature, vol. 347, pp. 539-541 (1990).
Kido et al., Applied Physics Letters, vol. 64, No. 7, pp. 815-817 (1994).
Granstrom et al., Applied Physics Letters, vol. 68, No. 2, pp. 147-149 (1996).
Tasch et al., Applied Physics Letters, vol. 71, No. 20, pp. 2883-2885 (1997).
Lee et al., Applied Physics Letters, vol. 79, No. 3, pp. 308-310 (2001).
Paik et al., Macromolecules, vol. 35, pp. 6782-6791 (2002).
Liu et al., Journal of Materials Chemistry, vol. 18, pp. 319-327 (2008).
Liu et al., Journal of Materials Chemistry, vol. 16, pp. 1431-1438 (2006).
Liu et al., Advanced Materials, vol. 19, pp. 4224-4228 (2007).
Liu et al., Advanced Functional Materials, vol. 17, pp. 1917-1925 (2007).
Liu et al., Advanced Functional Materials, vol. 16, pp. 957-965 (2006).
Tu et al., Advanced Functional Materials, vol. 16, pp. 101-106 (2006).

* cited by examiner

*Primary Examiner*—Duc Truong
(74) *Attorney, Agent, or Firm*—Dickstein Shpairo LLP

(57) ABSTRACT

This invention relates to a white electroluminescent polymeric material and preparation thereof. Based on the physical idea that white light emission can be achieved by regulating the relative luminous intensities of blue- and orange-light emitting units located in a single polymer molecule, the present invention provides three types (main chain type, pendant chain type, and terminal group type) of high efficiency and stable white electroluminescent polymeric material systems.

1 Claim, No Drawings

WHITE ELECTROLUMINESCENT POLYMERIC MATERIAL AND PREPARATION THEREOF

TECHNICAL FIELD

This invention relates to a white electroluminescent polymeric material and preparation thereof.

BACKGROUND ART

Since the electroluminescence of poly(p-phenylene vinylene) (PPV) was first reported by Burroughs et al, Cambridge Univ. U.K. in 1990, the polymeric electroluminescent material and manufacturing device thereof has been extensively concerned and investigated by the research and industry circles due to its prominent characteristics of simple process, easy to achieve large screen display and flexible display etc. At present, some typical blue-, green- and red-light polymeric luminescent material systems, such as poly(p-phenylene) (PPP), poly(alkylfluorene) (PAF), poly(phenylvinylene) (PPV), polythiophene (PTh) etc, have been developed. All the performance indexes of the monochromatic light polymeric electroluminescent device made of them can fulfill practical requirements. By contrast, there is a larger gap between every performance index of white light polymeric device and practical requirement. It is necessary to research deeply the material design and device structure separately so as to accelerate the course of industrialization of white light polymeric device.

The means for achieving white light polymeric electroluminescent device mainly include: (1) blending system of organic fluorescent dye/polymer; (2) blending system of polymer/polymer; (3) single white light polymeric system. For example, J. kido et al. disclosed a method for obtaining white luminescence with a maximum luminance of 3400 cd/m$^2$ by dispersing three kinds of fluorescent dyes (red, green and blue) in poly(vinylcarbazol) (PVK) and regulating the contents of the three dyes, Appl. Phys. Lett., 64, 815, 1994; Inganas et al. disclosed another method for obtaining a white light emission (CIE 0.220, 0.466) by blending the polythiophene derivatives (red, green and blue) with an inert polymer (such as PMMA) under a high driving voltage (20V), Appl. Phys. Lett., 68, 147, 1996. But the system has the following disadvantages: the obvious phase separation between polymer and polymer results in the voltage-dependence of white light emission, and thus a stable white light device is difficult to be obtained. Leising research group disclosed a method for obtaining a white light polymeric device having an external quantum efficiency of 1.2% by dispersing a trace amount (0.66 wt %) of red light poly (perylene-co-diethynylbenzene) (PPDB) in a high efficiency blue light laddertype (polyparaphenylene) (m-LPPP), in which the voltage-dependence of white color purity was improved to a certain extent due to the formation of a homogeneous blending system of polymer/polymer, see Appl. Phys. Lett., 71, 2883, 1997. For the single polymeric white light system disclosed in "Appl. Phys. Lett., 79, 308, 2001" and "Macromolecules, 35, 6782, 2002", it is obtained by forming an exciplex during the electroluminescence of PPV polymer (blue or blue-green), which can bring about a wideband luminescence, so the white light polymeric device made thereof has a sharp voltage-dependence of color and relatively poor performances.

DISCLOSURE OF THE INVENTION

The object of this invention is to provide a white electroluminescent polymeric material.

Another object of this invention is to provide a method for preparing a white electroluminescent polymeric material.

The inventors of the present invention find that white light emission can be achieved by regulating the relative luminous intensities of blue- and orange-light emitting units located in a single polymer molecule. Based on such a physical idea, the present invention provides three types (main chain type, pendant chain type, and terminal group type) of high efficiency and stable white electroluminescent polymeric material systems.

The present invention provides the following aspects.

1. A white electroluminescent polymeric material, which comprising a single white electroluminescent polymeric material selected from a group consisting of:

type (I): main chain type single white electroluminescent polymeric material,

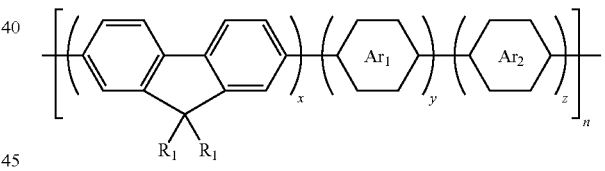

wherein: $R_1$ is alkyl or aryl, Ar1 is a naphthalimide derivative basic unit having one or more structures as listed below:

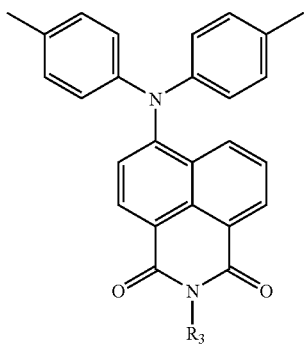

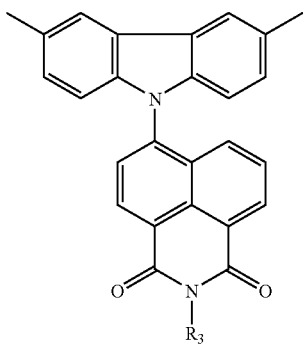

-continued
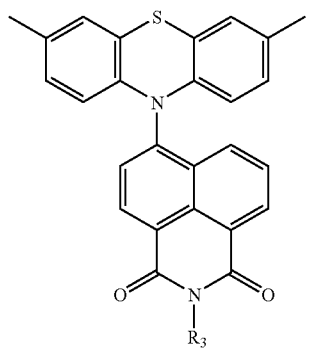
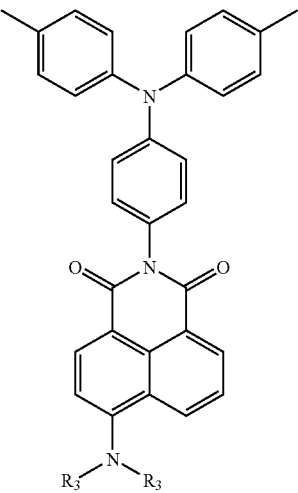
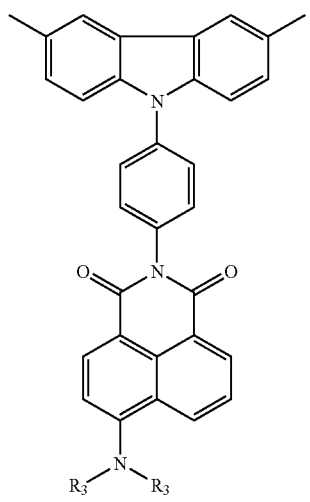
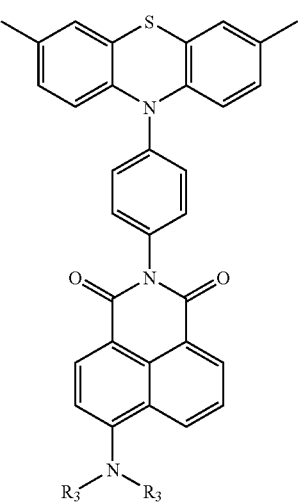
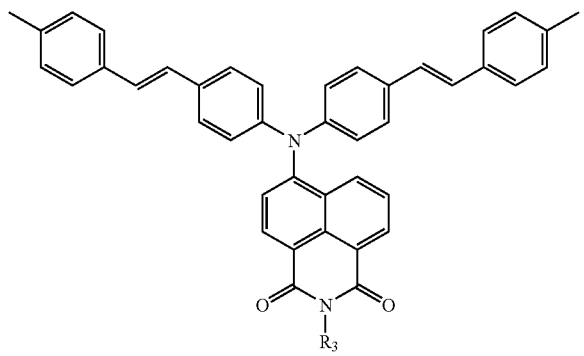
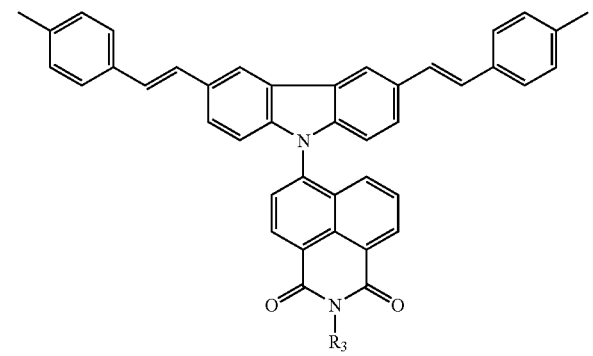

-continued
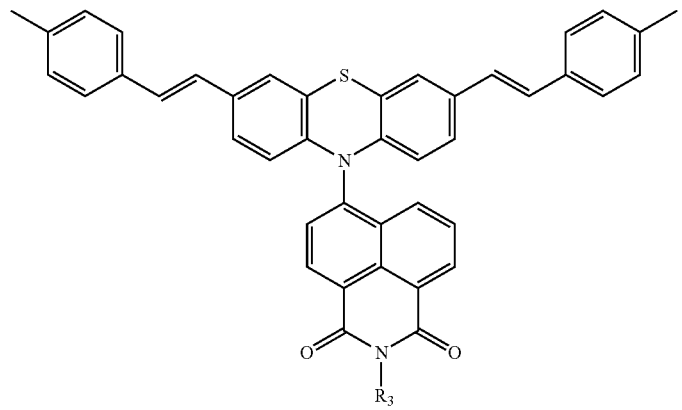
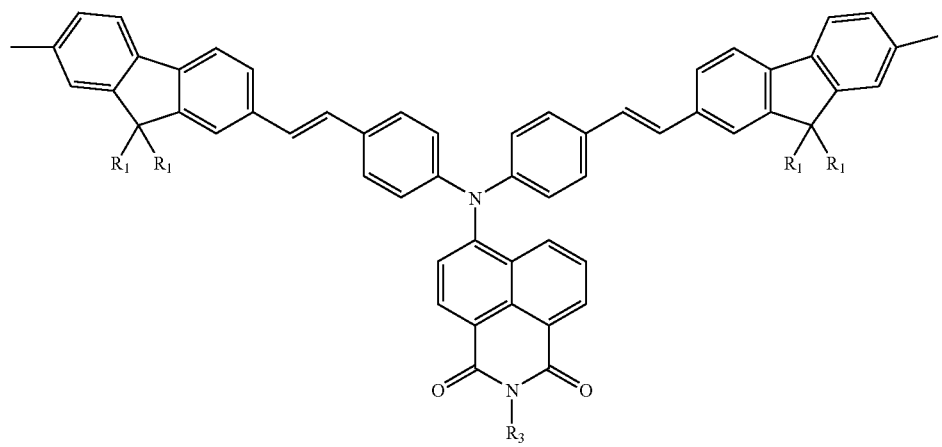
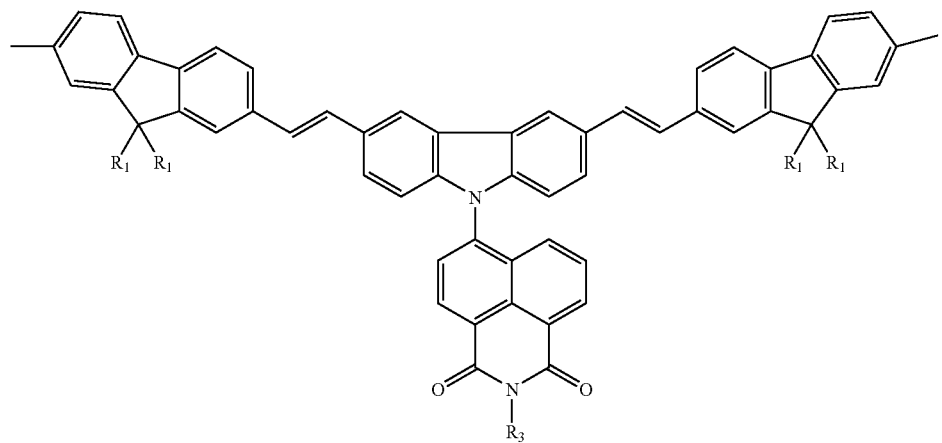

-continued
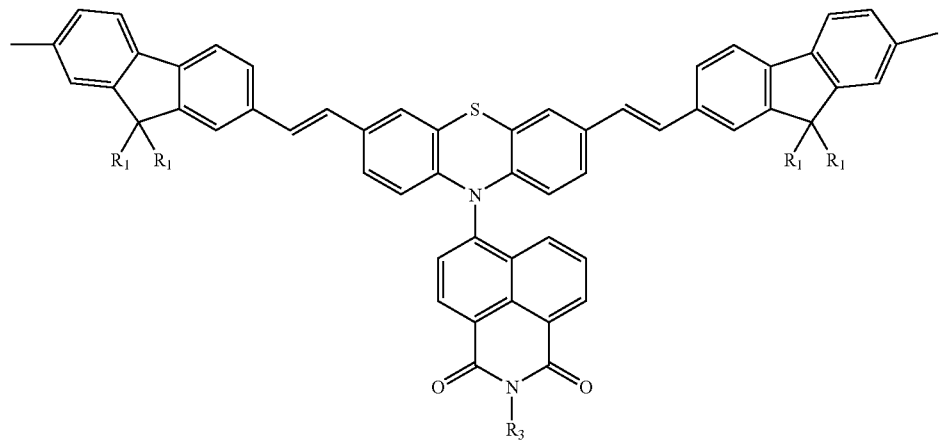
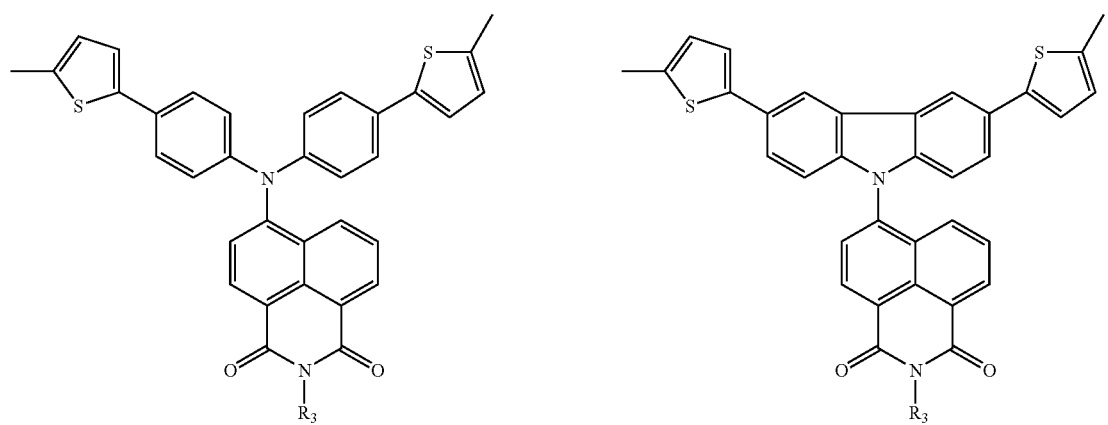
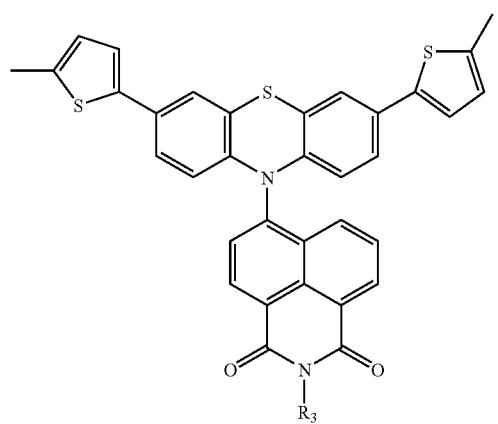

-continued
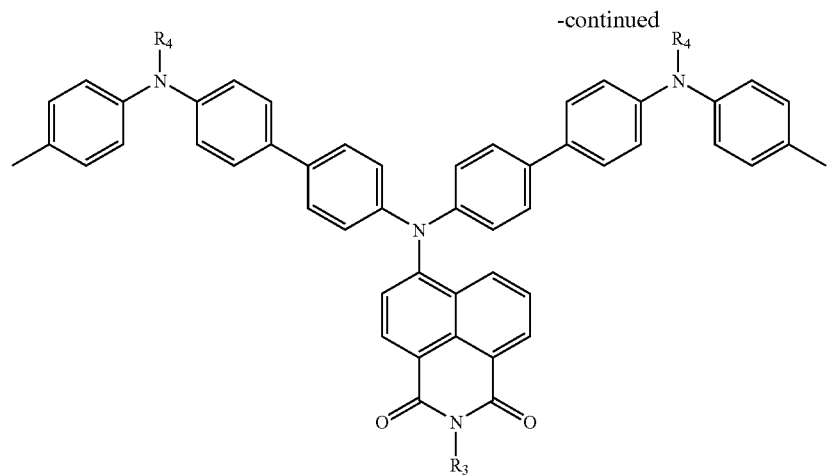
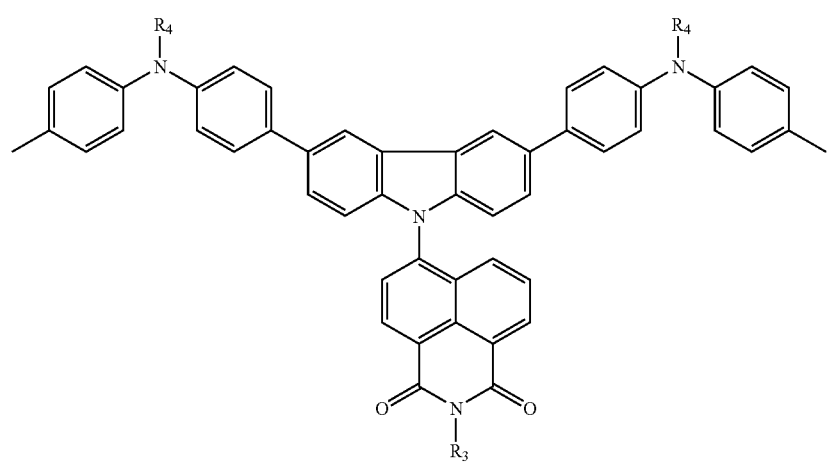
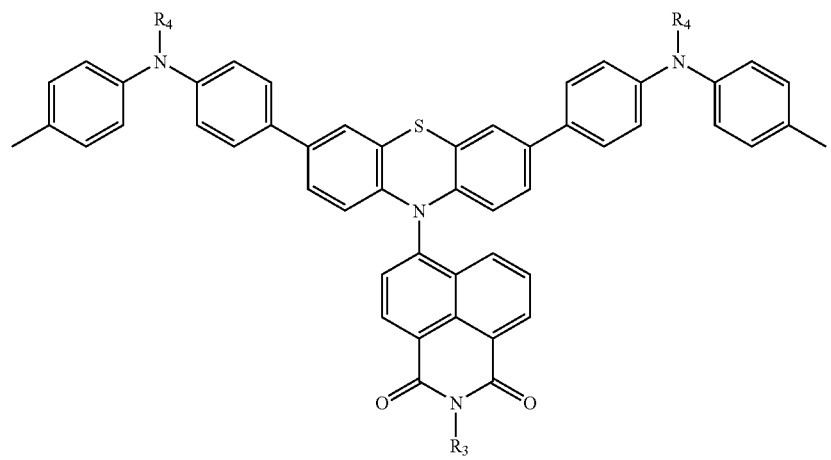

-continued
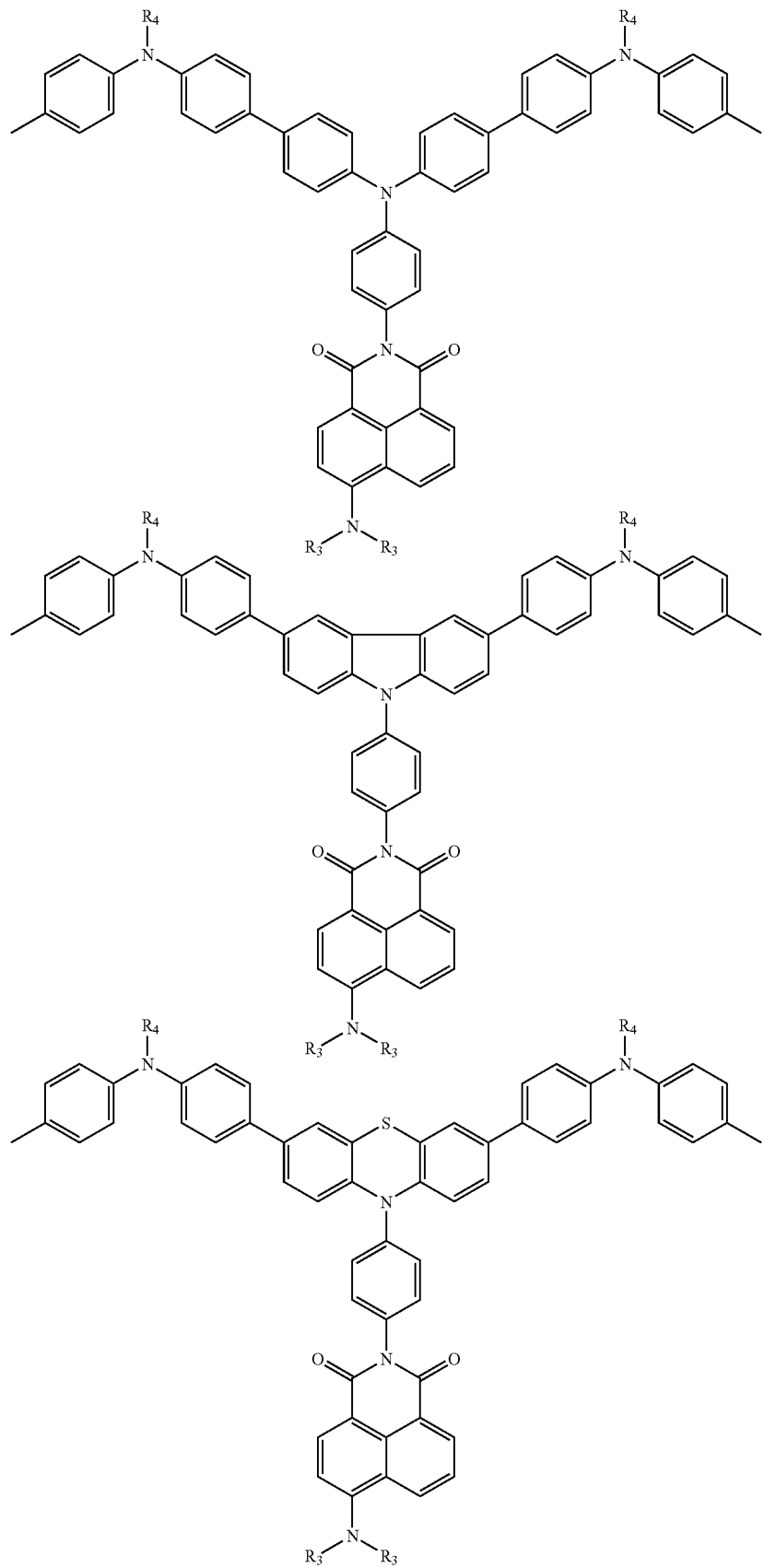

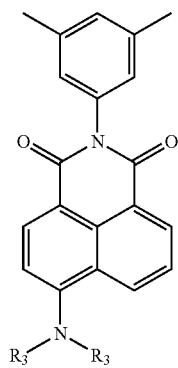
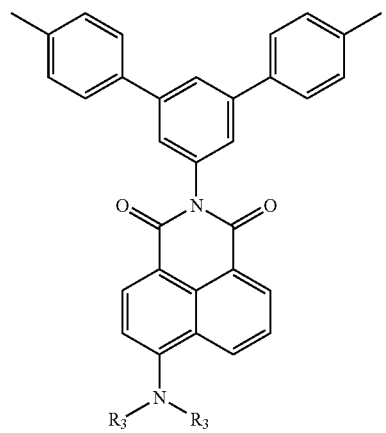
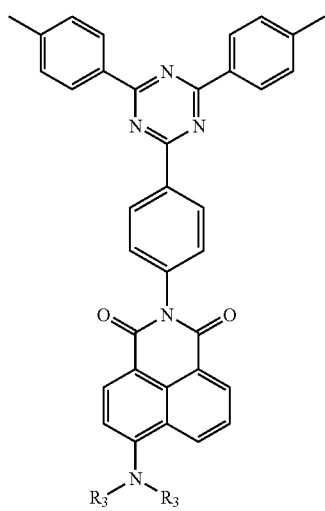
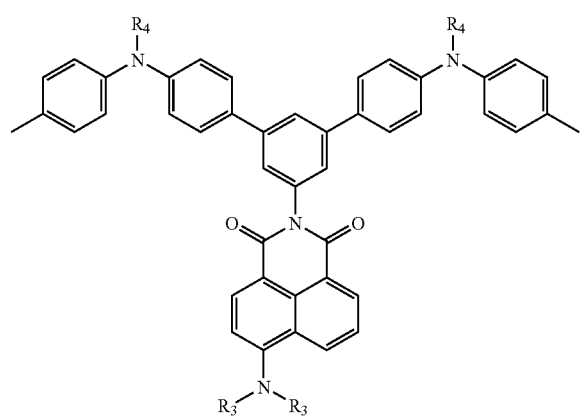
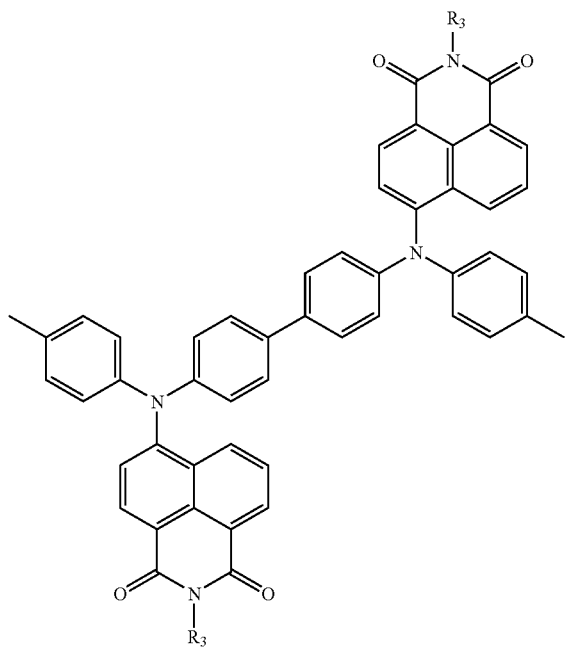
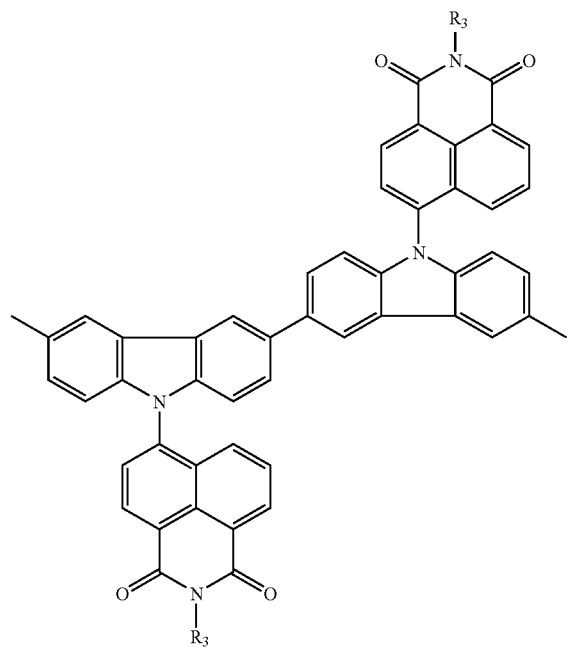

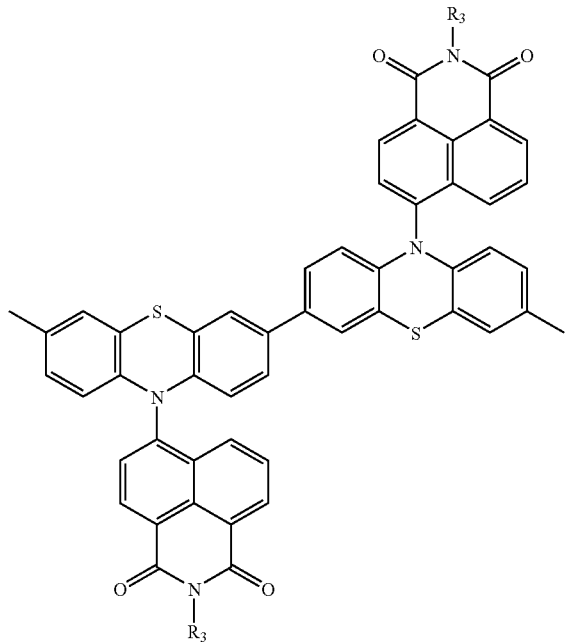

wherein, Ar2 is an electron transport basic unit, a hole transport basic unit or a luminescence basic unit; x, y, and z each represents the content of one basic unit, satisfying $0<x<1$, $0<y<1$, $0\leqq z<1$, $x+y+z=1$, and $n=1$-300, wherein, the chain lengths of the alkyl and the alkoxy are 1-18; the aryl is selected from a group consisting of phenyl, naphthyl, fluorenyl, triphenylamino, oxadizolyl, and phenyl or naphthyl substituted by alkyl or alkoxy; $R_3$ and $R_4$ independently represent an alkyl having a chain length of 1-18 or an aryl, wherein the aryl is selected from a group consisting of phenyl, naphthyl, and phenyl or naphthyl substituted by alkyl or alkoxy;

Ar2 has one or more structural units selected from the following units:

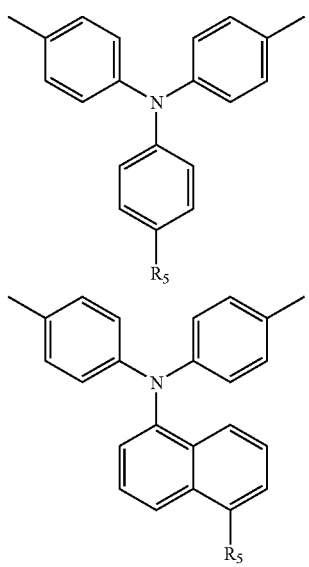

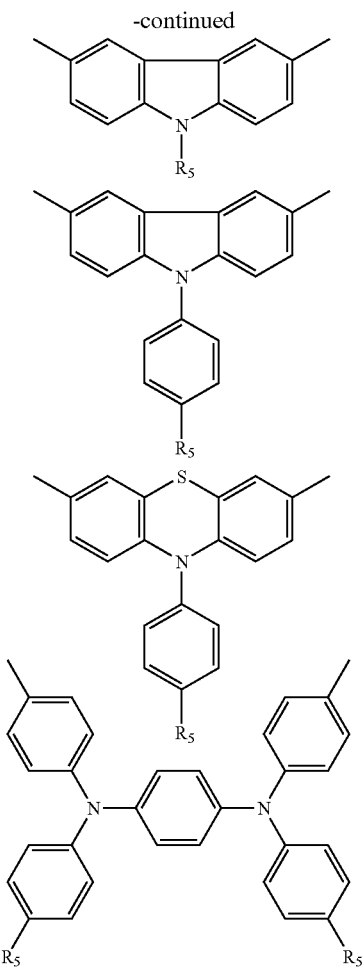

-continued
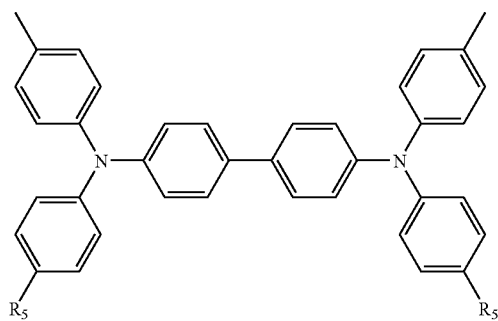
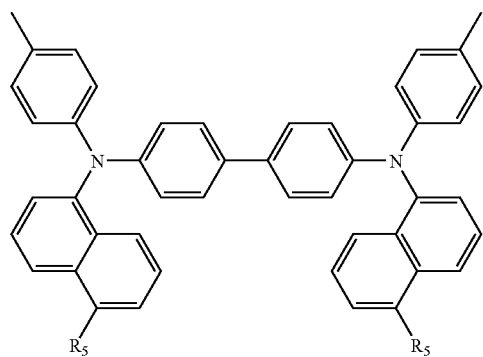
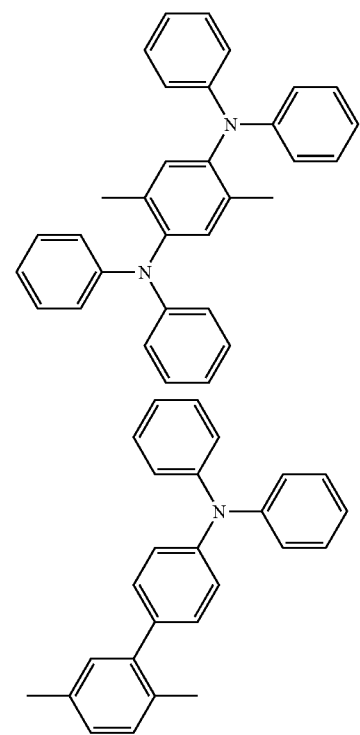
-continued
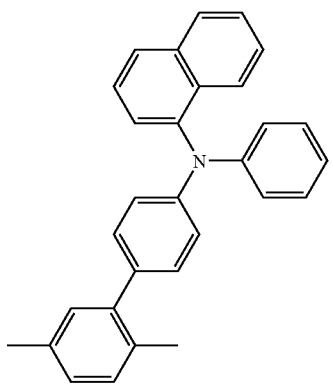
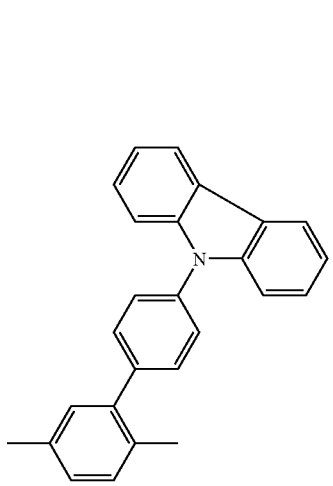
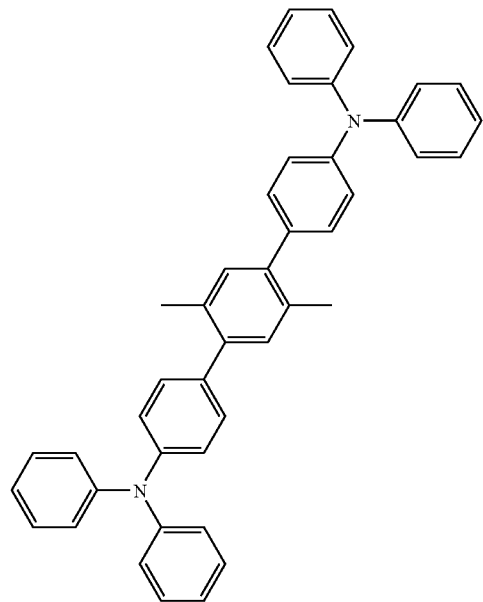

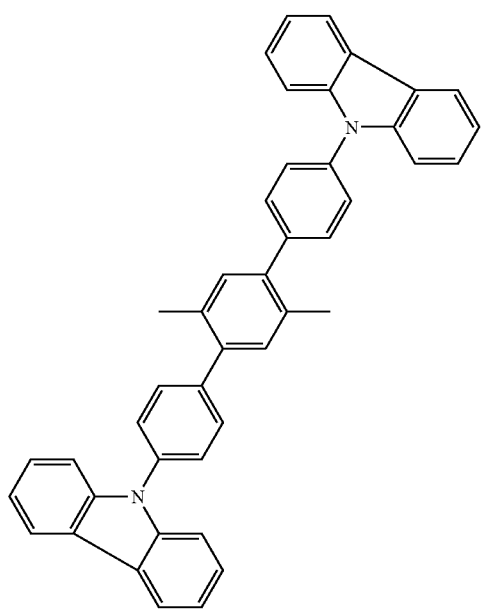

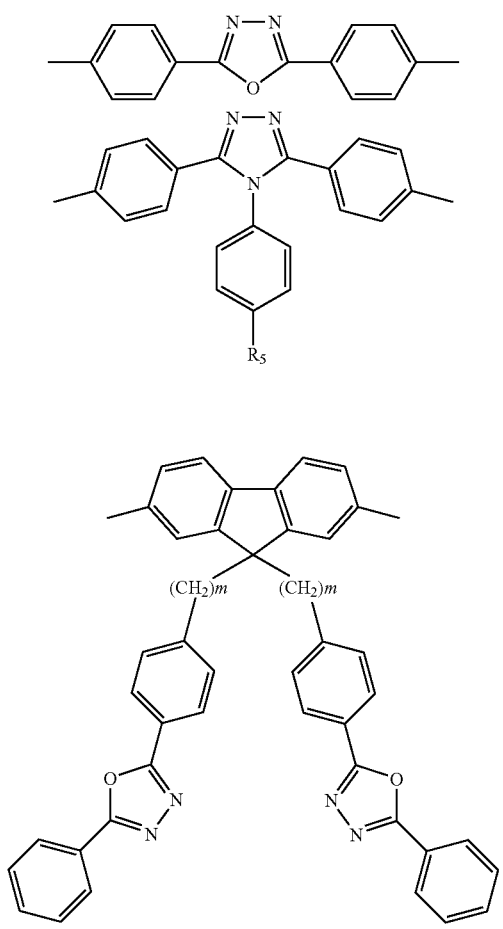

wherein $R_5$ is selected from a group consisting of alkyl, phenyl, naphthyl, and phenyl or naphthyl substituted by alkyl or alkoxy, m=0-20; wherein, the chain lengths of the alkyl and the alkoxy are 1-18;

type (II): pendant chain type single white electroluminescent polymeric material

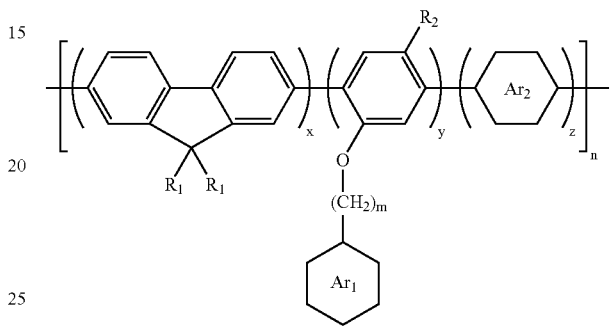

wherein: $R_2$ is selected from a group consisting of alkyl, alkoxy, phenyl, and phenyl substituted by alkyl or alkoxy; Ar1 is a naphthalimide derivative basic unit; The basic structure of Ar2 is the same as the Ar2 of the main chain type single white luminescent polymeric material; Each basic unit content—x, y and z satisfy $0<x\leqq1$, $0<y<1$, $0\leqq z<1$, x+y+z=1, m=0-20, n=1-300; wherein the chain lengths of the alkyl and the alkoxy are 1-18;

Ar1 has one or more structures as listed below:
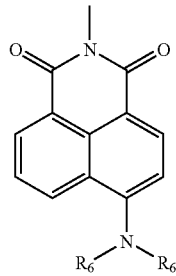
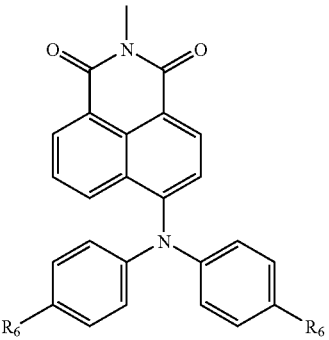
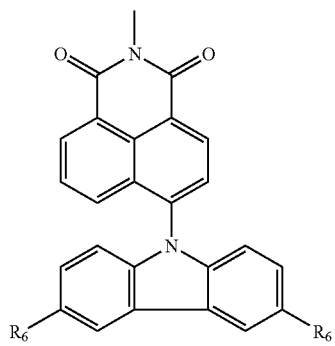
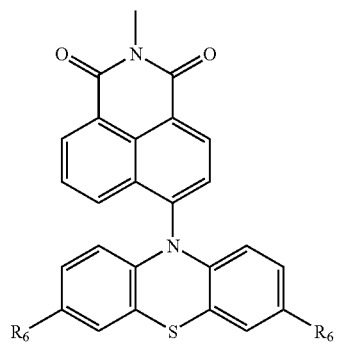
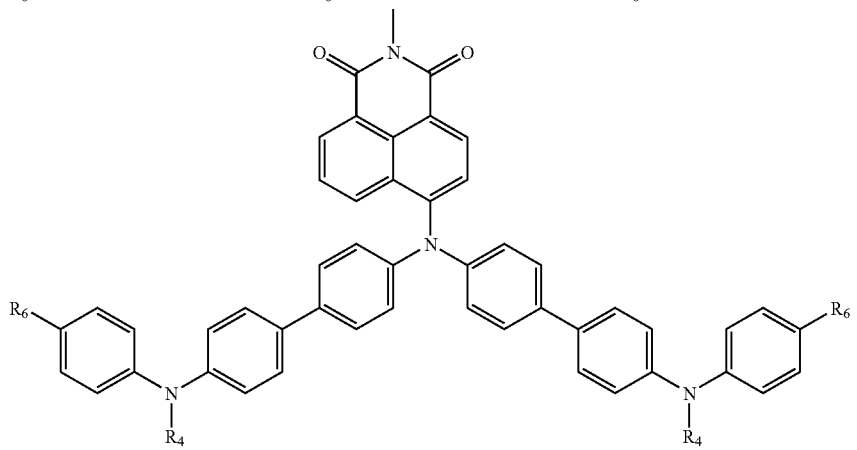
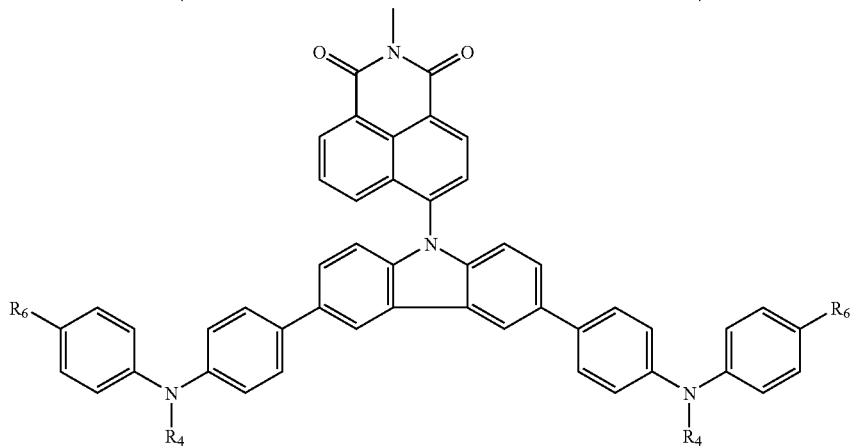

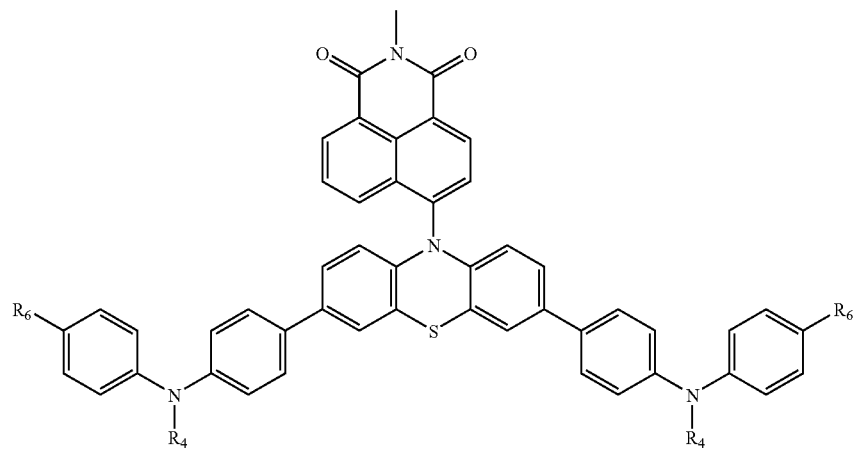
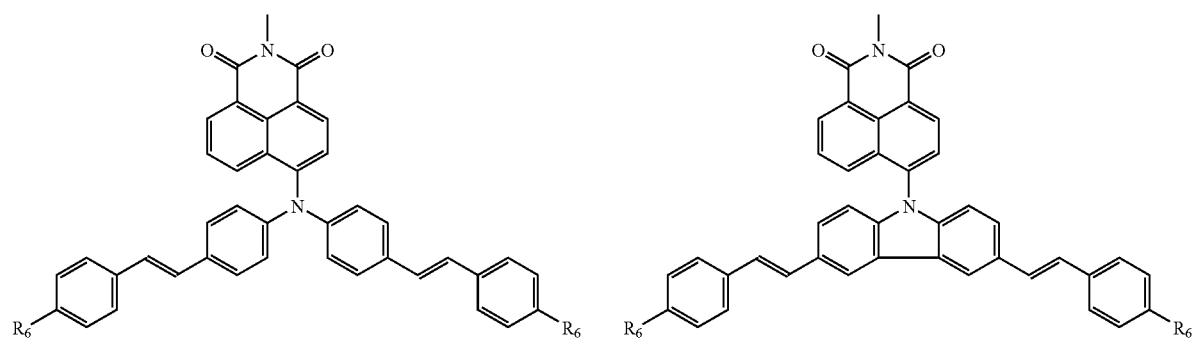
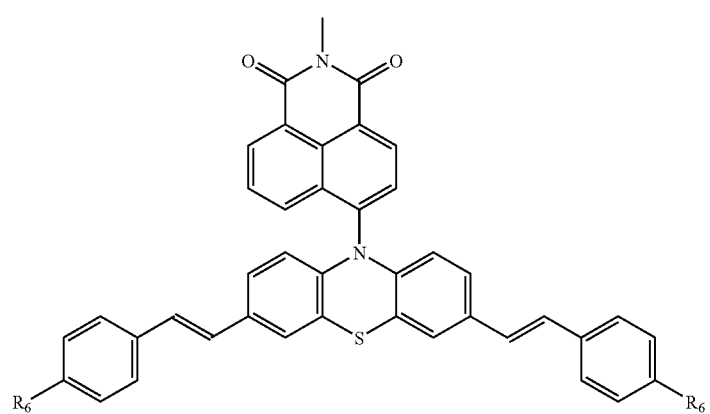
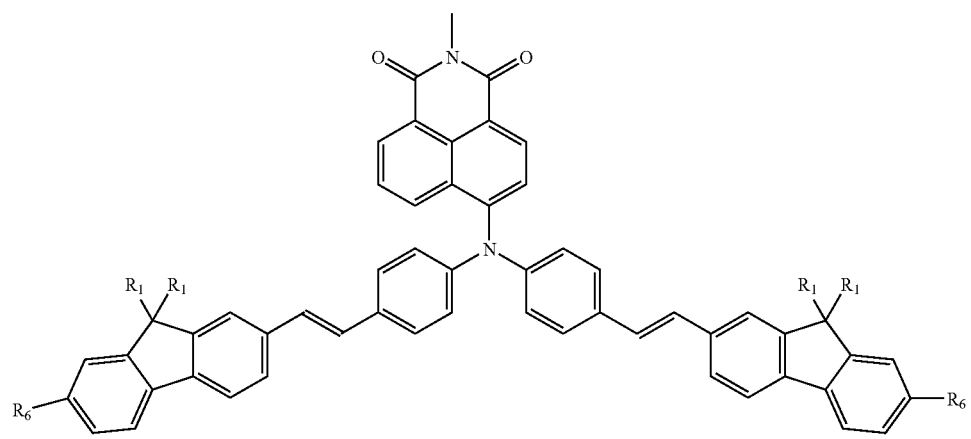

-continued
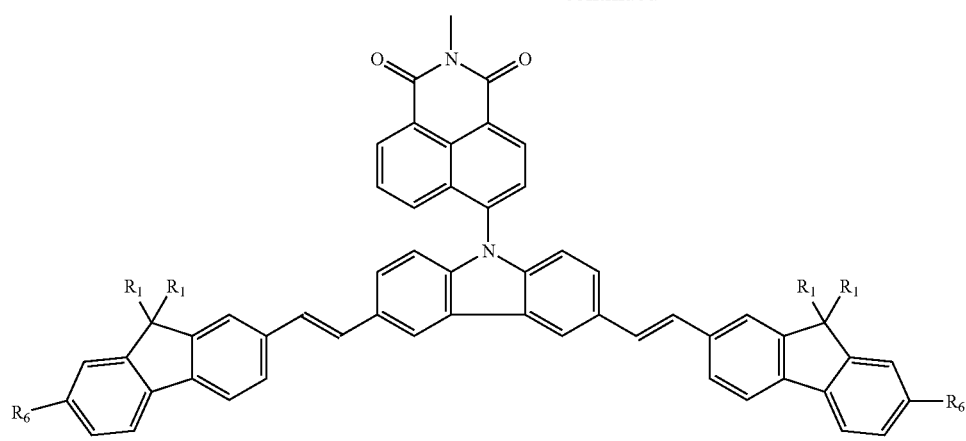
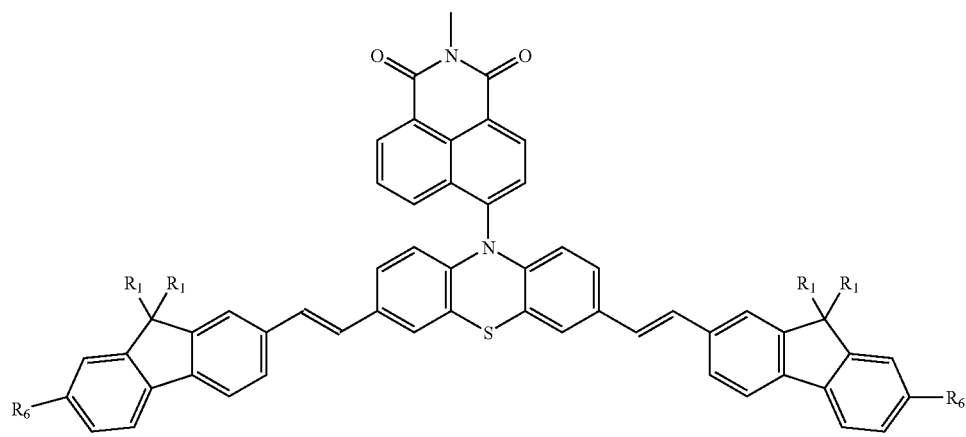
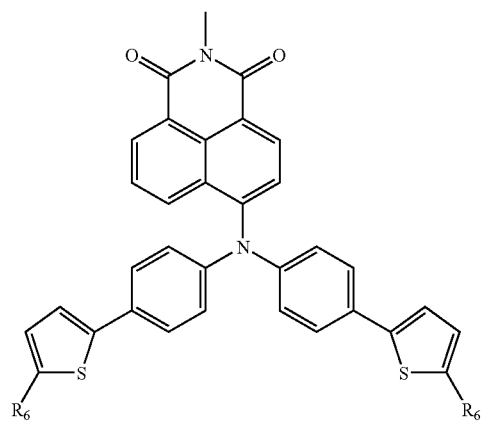
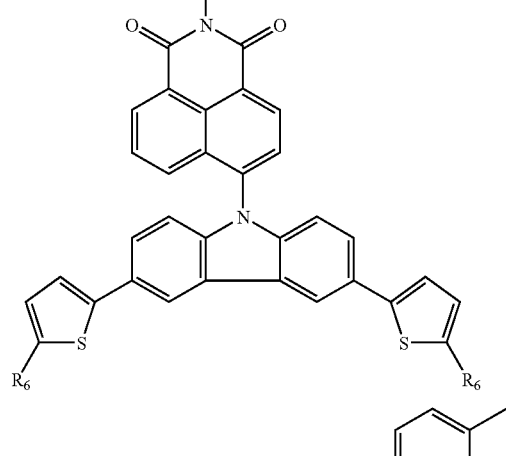
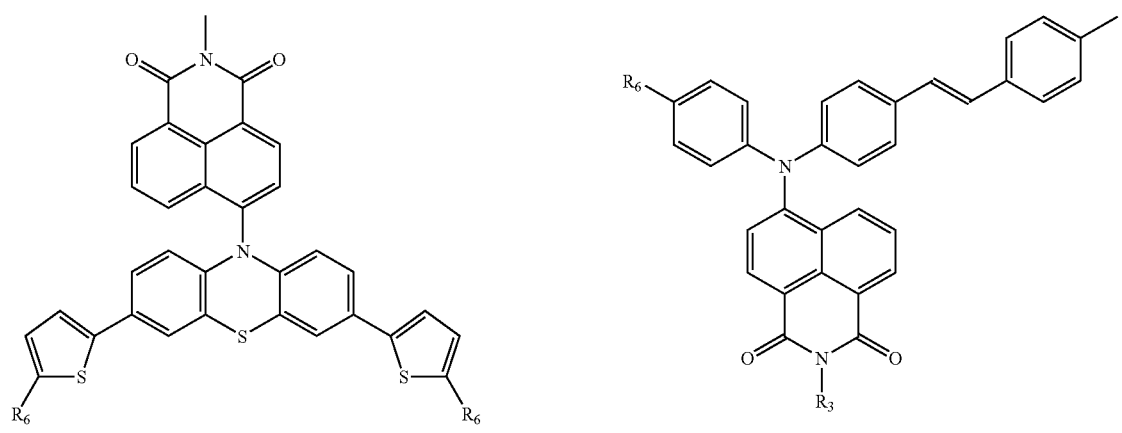
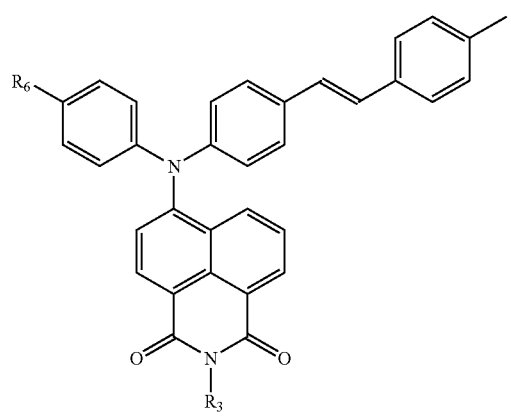

-continued

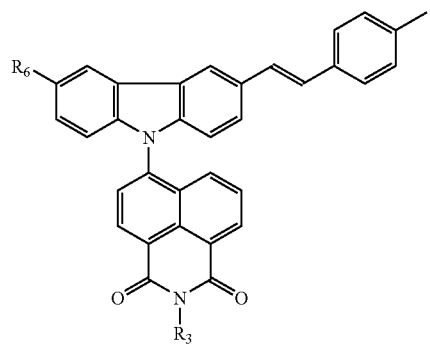
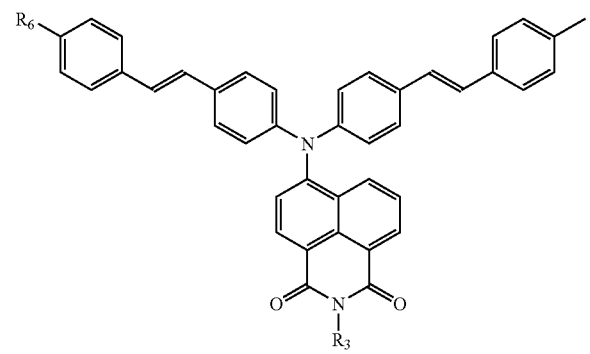

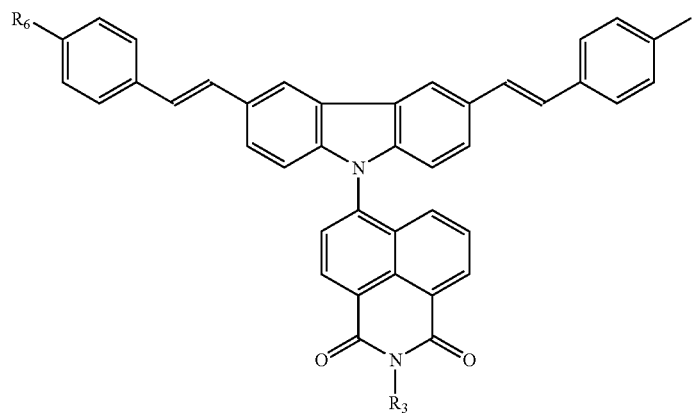

wherein R₆ is alkyl, phenyl, naphthyl, a phenyl or naphthyl group substituted by alkyl or alkoxy, wherein the chain lengths of the alkyl and the alkoxy are 1-18; and type (III): Terminal group type single white electroluminescent polymeric material

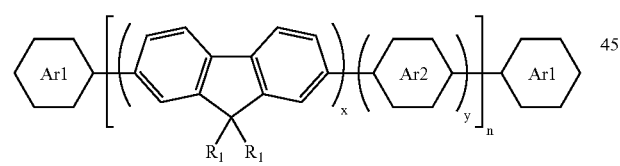

wherein: Ar1 is a naphthalimide derivative basic unit; the structure of Ar2 is the same as the Ar2 of the main chain type single white luminescent polymeric material; x and y are basic unit contents and satisfy $0<x\leqq1$, $0<y<1$, $x+y=1$; $n=1$-300;

Ar1 has one or more structures as listed below:

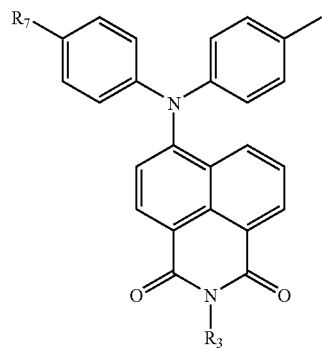
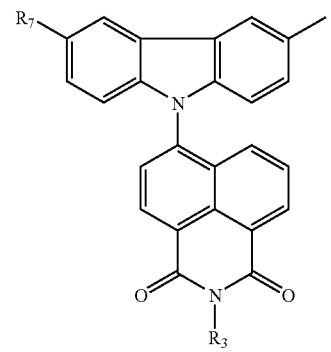

-continued
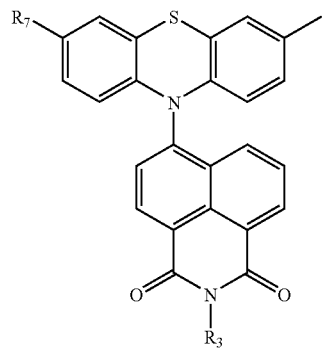
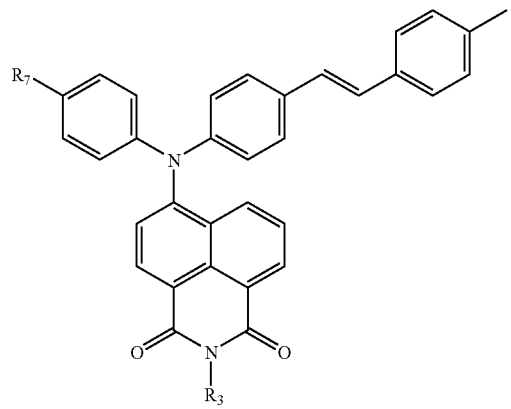
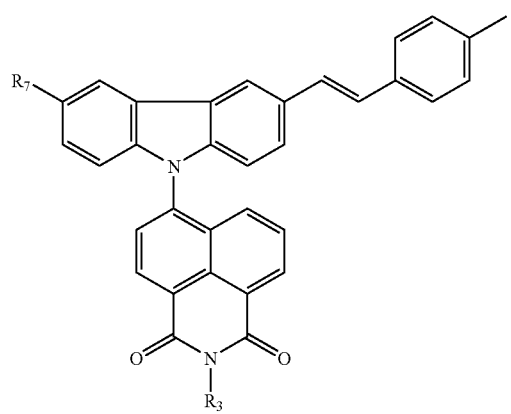
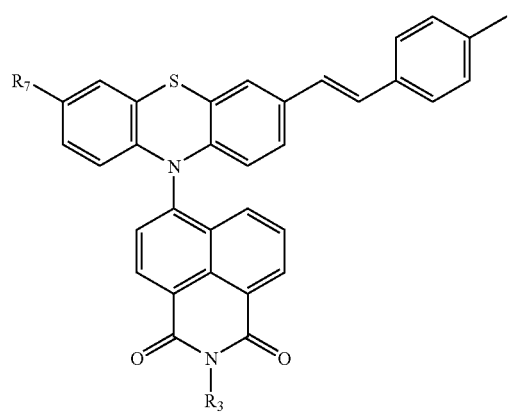
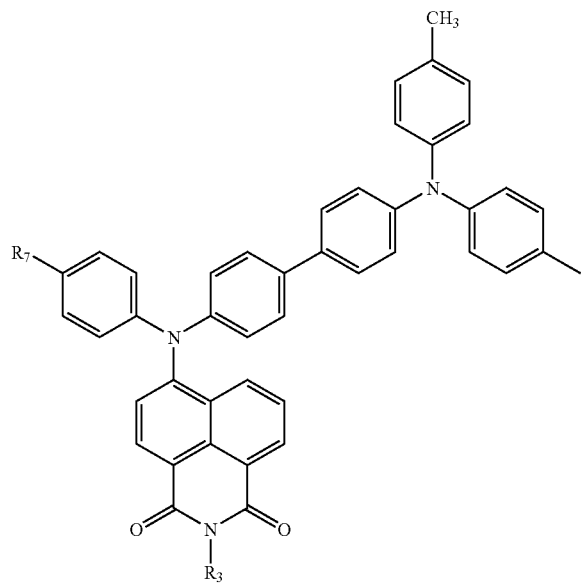
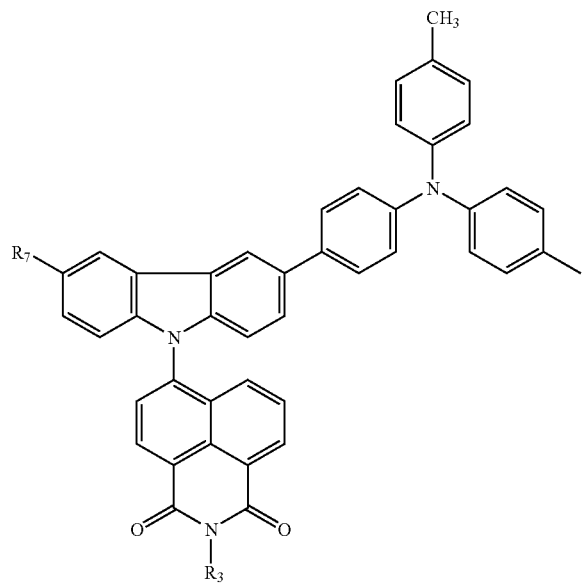

-continued
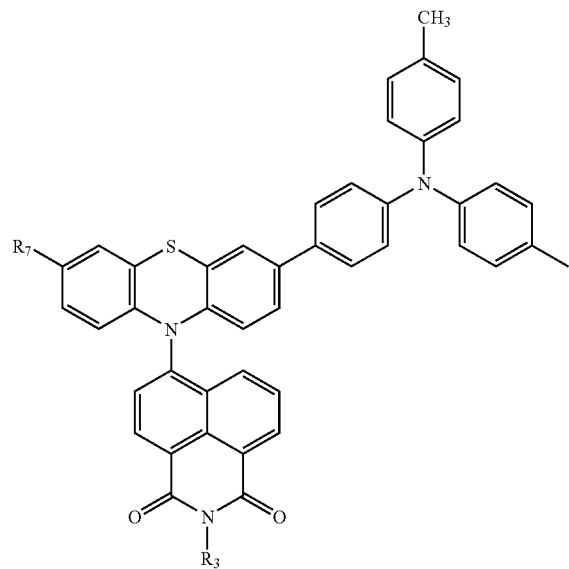
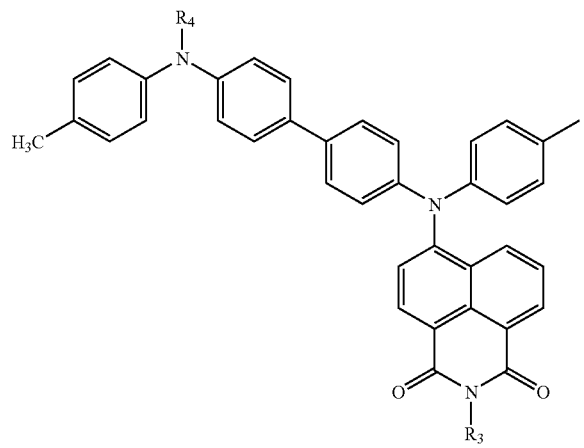
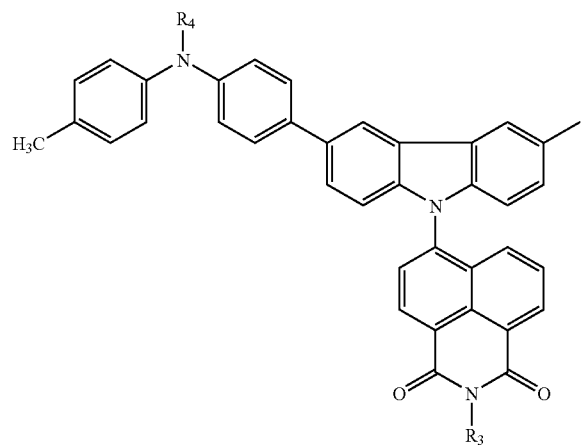
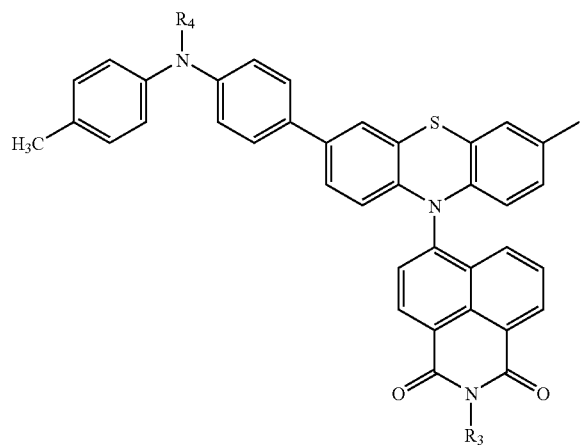
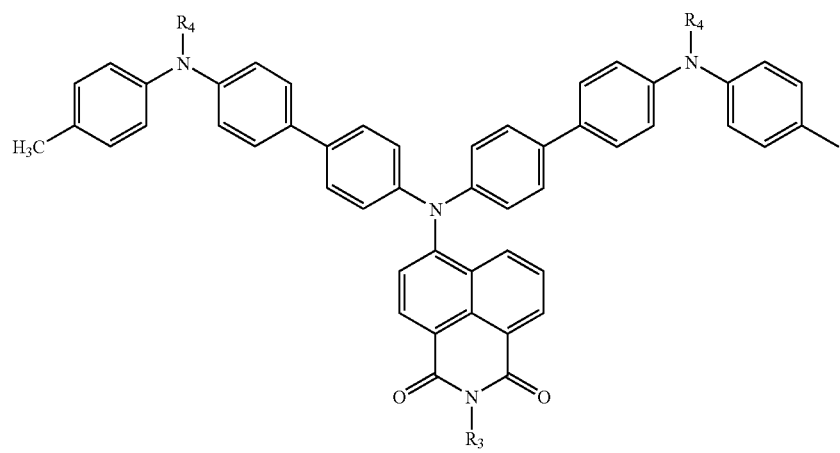

-continued

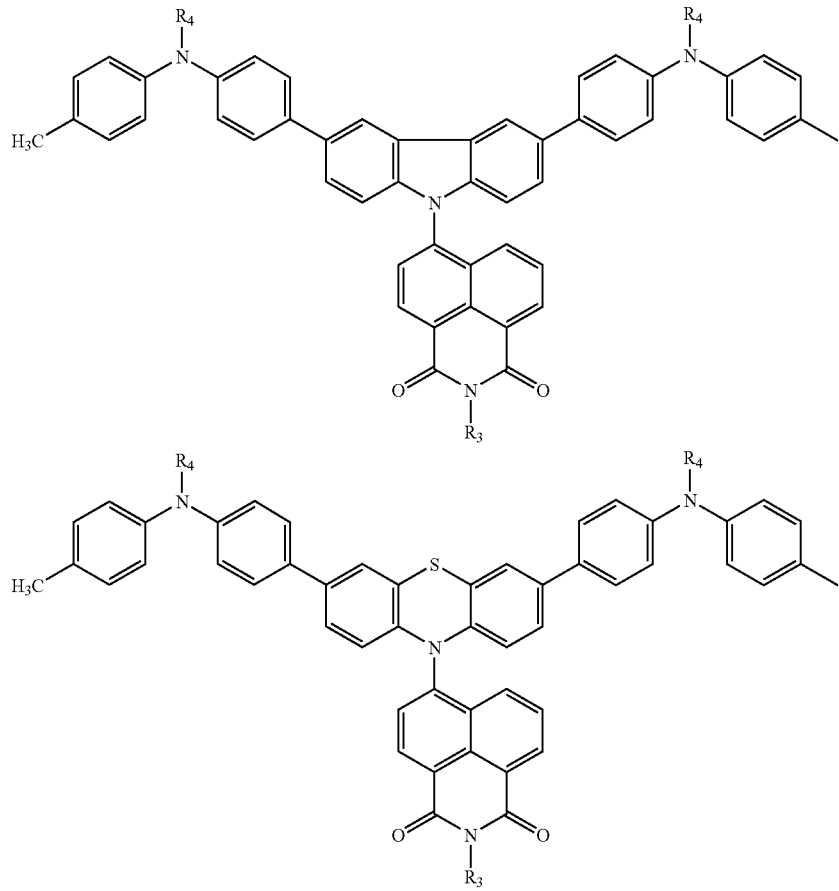

wherein R₇ is alkyl, phenyl, naphthyl, or a phenyl or naphthyl group substituted by alkyl or alkoxy; wherein the chain length of alkyl and alkoxy is 1-18.

2. A process for preparing the white electroluminescent polymeric material according to aspect 1, comprising steps of:
 a. providing a monomer selected from a group consisting of:
 (1) monomers with a formula as follows:

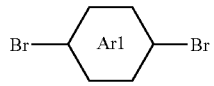

wherein, Ar1 is the same as that in the main chain type single white luminescent polymeric material according to aspect 1;

(2) monomers with a formula as follows:

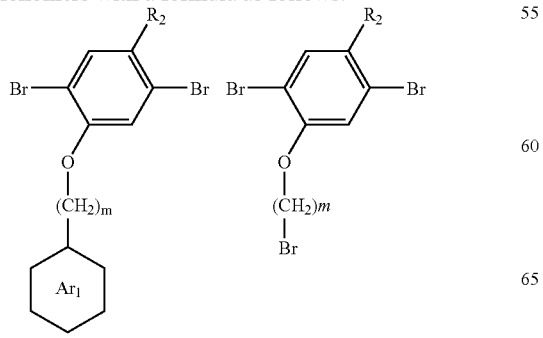

wherein, Ar1 is the same as that in the pendant chain type single white luminescent polymeric material according to aspect 1, m=0-20, preferably 1-20;

(3) monomers with a formula as follows:

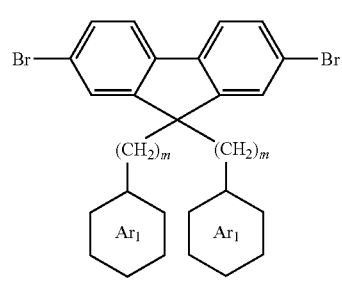

wherein, Ar1 is the same as that in the pendant chain type single white luminescent polymeric material according to aspect 1, m=0-20, preferably 1-20; and (4) monomers with a formula as follows:

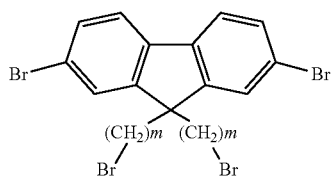

wherein, Ar1 is the same as that in the pendant chain type single white luminescent polymeric material according to aspect 1, m=0-20, preferably 1-20;

b. providing a monomer selected from a group consisting of:

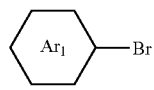

wherein, Ar1 is the same as that in the terminal group type single white luminescent polymeric material defined in aspect 1; and c. polymerizing a monomer obtained in step (a) and a monomer obtained in step (b) using the Yamamoto polymerization method or the Suzuki polymerization method.

3. The method according to aspect 2, wherein the monomer (1) in step a is prepared by a method comprising steps of: dissolving naphthalimide derivative Ar1 and 2-4 mole equivalents of tetrabutyltriammonium bromide in dichloromethane; reacting the resulting solution, preferably at room temperature, for 10-1200 min; and separating the reaction product.

4. The method according to aspect 2, wherein the monomer (2) in step a is prepared by a method comprising steps of: dissolving 4-amino-1,8-naphthalimide and 1-5 mole equivalents of 2-(m-bromoalkoxy)-5-substituted-1,4-dibromobenzene in dimethyl sulfoxide; adding 1-10 mole equivalents of MOH wherein M represents Li, Na or K; reacting at 50-150° C. for 1-120 hr; stopping the reaction and separating the intermediate product; dissolving the intermediate product, 2-20 mole equivalents of iodobenzene, 2-20 mole equivalents of carbonate, preferably, sodium carbonate or potassium carbonate, 1-5% mole equivalent of 18-crown-6 and 1-5% mole equivalent of cuprous iodide in a solvent, preferably DMPU (1,3-dimethyl-3,4,5,6-tetrahydro-2(1H)-primidinone); heating to 140-200° C. under an inert gas, preferably N$_2$ gas, to react for 5-50 hr; and separating the product.

5. The method according to aspect 2, wherein the monomer (3) in step a is prepared by a method comprising steps of: contacting N,N-diphenyl-1,8-naphthalimide derivative with 15-80 mole equivalents of POCl$_3$ in dimethyl formamide at 50~100° C. for 20-100 hr to produce 4-aldo or 4,4'-dialdo-N,N-diphenyl-1,8-naphthalimide derivative; dissolving the resulting product and 0.5-1 mole equivalents of 9-phenyl-9-(4-bromotributylphosphino-methylenephenyl)-2,7-dibromofluorene or 9,9-(4-bromotributylphosphino-methylenephenyl)-2,7-dibromofluorene in a chloroform solution; adding a solution of 4-10 mole equivalents of sodium ethoxide; reacting at room temperature for 10-50 hr; and separated the reaction product.

6. The method according to aspect 2, wherein the monomer (4) in step a is prepared by a method comprising the steps of: dissolving 9,9-(m-bromoalkyl)-2,7-dibromofluorene and 2-3 mole equivalents of 4-amino-1,8-naphthalimide in a solvent, preferably, DMSO; adding 2-20 mole equivalents of MOH wherein M represents Li, Na or K; reacting at 50-150° C. for 1-120 hr; separating the intermediate product; dissolving the intermediate product, 4-20 mole equivalents of iodobenzene, 6-20 mole equivalents of potassium carbonate, 2-10% mole equivalents of 18-crown-6, 2-10% mole equivalent of cuprous iodide in a solvent such as DMPU; heating the solution to 140-200° C. to react for 5-50 hr; and separated the product.

7. The method according to aspect 2, wherein the monomer b in step b is prepared using a method comprising steps of: dissolving naphthalimide derivative Ar1H and 1-2 mole equivalents of tetrabutyltriammonium bromide in a solvent, preferably, dichloromethane; reacting, preferably at room temperature, for 10-1200 min; and separated the product.

8. The method according to aspect 2, wherein, for obtaining the main chain type single white light polymeric material, the Yamamoto polymerization method comprising steps of:
dissolving 2,7-dibromofluorene derivative monomer, 0.01%-10% mole equivalent of dibromonaphthalimide derivative monomer and 0-30% mole equivalent of dibromoaromatic monomer in a solvent, preferably anhydrous toluene, under the protection of an inert gas, preferably N$_2$ gas;
dropping the resulting solution into a solution of 2-3 mole equivalents of Ni (0) in a solvent, preferably dimethyl formamide;
reacting at 50-100C. for 24-120 hr; and
separating the product.

9. The method according to aspect 2, wherein, for obtaining the main chain type single white light polymeric material, the Suzuki polymerization method comprising steps of:
dissolving 2,7-diborate fluorene derivative monomer, 0.01-10% mole equivalent of dibromonaphthalimide derivative monomer and 0-20% mole equivalent of dibromoaromatic monomer in a solvent, preferably toluene;
adding 3 mole equivalents of carbonate, preferably potassium carbonate or sodium carbonate, in a solution form;
under the protection of an inert gas, preferably N$_2$ gas and at 50-100° C., adding 0.05% mole equivalent of tetra(triphenylphosphino) palladium (0);
reacting for 1-200 hr; and
separating the product.

10. The method according to aspect 2, wherein, for obtaining the pendant chain type single white light polymeric material, the Yamamoto polymerization method comprising steps of:
dissolving 2,7-dibromofluorene derivative monomer, 0.01%-10% mole equivalent of any one of monomers (2)-(4) in step a, and 0-30% mole equivalent of dibromoaromatic monomer in a solvent, preferably anhydrous toluene, under the protection of an inert gas, preferably N$_2$ gas;
dropping the resulting solution into a solution of 2-3 mole equivalents of Ni (0) in a solvent, preferably dimethyl formamide;
reacting at 50-100° C. for 24-120 hr; and
separating the product.

11. The method according to aspect 2, wherein, for obtaining the pendant chain type single white light polymeric material, the Suzuki polymerization method comprising steps of:
dissolving 2,7-diborate fluorene derivative monomer, 0.01-10 mole equivalent of any one of monomers (2)-(4) in step a, and 0-20% mole equivalent of dibromoaromatic monomer in a solvent, preferably toluene;

adding 3 mole equivalents of carbonate, preferably potassium carbonate or sodium carbonate, in a solution form;

under the protection of an inert gas, preferably N₂ gas and at 50-100° C., adding 0.05% mole equivalent of tetra(triphenylphosphino) palladium (0);

reacting for 1-200 hr; and separating the product.

12. The method according to aspect 2, wherein, for obtaining the terminal group type single white light polymeric material, the Yamamoto polymerization method comprising steps of:

dissolving 2,7-dibromofluorene derivative monomer and 0-30% mole equivalent of dibromoaromatic monomer in a solvent, preferably anhydrous toluene, under the protection of N₂ gas;

dropping the resulting solution into a solution of 2-3 mole equivalents of Ni (0) in a solvent, preferably dimethyl formamide;

reacting at 50-100° C. for 24-120 hr; and separating the product.

13. The method according to aspect 2, wherein, for obtaining the terminal group type single white light polymeric material, the Suzuki polymerization method comprising steps of:

dissolving 2,7-diborate fluorene derivative monomer and 0-30% mole equivalent of dibromoaromatic monomer in a solvent, preferably toluene;

adding 3 mole equivalents of carbonate, preferably potassium carbonate or sodium carbonate, in a solution form;

under the protection of N₂ gas and at 50-100° C., adding 0.050% mole equivalent of tetra(triphenylphosphino) palladium (0);

reacting for 24-120 hr;

adding 0.01-10% mole equivalent of monobromonaphthalimide derivative monomer;

reacting at 50-100° C. for 1-48 hr; and separating the product.

PREFERRED EMBODIMENTS OF THE INVENTION

In this invention, polyfluorene and its derivative are used as the structural unit for blue light, naphthalimide derivative as that for orange light.

In the present invention, otherwise indicated, the term "alkyl" means a straight or branched alkyl having 1-18, preferably 1-10, more preferably 1-6 carbon atoms, the term "alkoxy group" means a straight or branched alkoxy group having 1-18, preferably 1-10, more preferably 1-6 carbon atoms, and the term "aryl" means an aryl optionally substituted by an alkyl or aryl, more preferably, having 6-18 carbon atoms.

The preparation methods for the three types of white electroluminescent polymeric material mainly relates to five types of monomers and two types of copolymerization reactions.

Examples of the preparations methods are provided as follows:

1. Preparation of 2,7-dibromofluorene and the Monomer Derived therefrom

The general structural formulas of 2,7-dibromofluorene and the monomer derived therefrom are as follows:

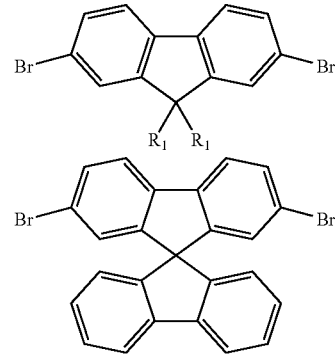

That is, 2,7-dibromofluorene and the monomer derived therefrom can be classified as 9,9-dialkyl-2,7-dibromofluorene monomer and 9,9-diaryl-2,7-dibromofluorene. Their preparation methods are respectively described as follows:

a) Preparation of 9,9-dialkyl-2,7-dibromofluorene monomer 2,7-dibromofluorene and 2-6 mole equivalents of excessive bromoalkane are dissolved in toluene, then 2-50 mole equivalents of 10-70% NaOH aqueous solution was added. After reacting under the protection of N₂ gas for 1-24 hr at 30-100° C., the reaction product was poured into water, and then the organic phase was separated, washed repeatedly with water, dried, concentrated and recrystallized to obtain 9,9-dialkyl-2,7-dibromofluorene.

b) Preparation of 9,9-diaryl-2,7-dibromofluorene monomer

First, 2,7-dibromofluorene ketone is dissolved in ethyl ether, under the protection of N₂ gas, 1-4 mole equivalents of an aryl Grignard reagent is then added. After reacting under reflux for 1-24 hr, 9-hydroxy-9-aryl-2,7-dibromofluorene is obtained. 9-hydroxy-9-aryl-2,7-dibromofluorene is then dropped slowly into an aryl hydrocarbon sulfuric acid solution in a mole ratio of 1:1-5. After refluxing for 1-24 hr, the reaction product is poured into water. The resulting organic phase is separated, washed repeatedly with water, dried, concentrated and recrystallized to obtain 9,9-diaryl-2,7-dibromofluorene.

2. Preparation of 9,9-disubstituted-2,7-biborate and Monomer Derived therefrom

The general structural formula of 9,9-disubstituted-2,7-biborate and monomer derived therefrom is one of the following formulas:

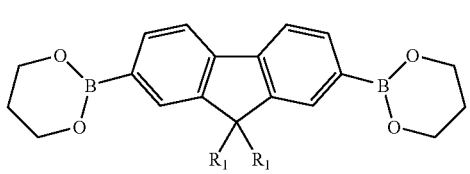

-continued

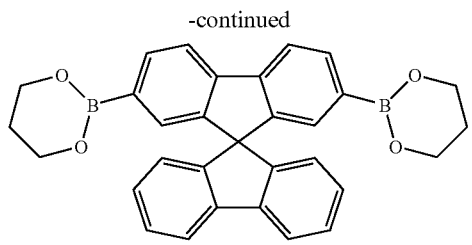

The preparation method for 9,9-dialkylfluorene-2,7-biborate, 9,9-spirobifluorene-2,7-biborate and monomer derived therefrom is as follows:

1-4 mole equivalents of n-butyllithium is added at −100~0° C. into a solution of 2,7-dibromofluorene and monomer derived therefrom in THF. After stirring for 1-10 hr, 2-10 mole equivalents of trimethyl borate is then added at −100~0° C. After stirring at room temperature for 1-48 hr, the reaction product is poured into water. Then the organic phase is separated, washed repeatedly with water, dried, concentrated, and dissolved in toluene. 2-10 mole equivalents of 1,3-propylene glycol is added. After refluxing for 1-72 hr, the reaction product is poured into water. The organic phase is separated, washed repeatedly with water, dried, concentrated and finally separated by column chromatography to produce 9,9-dialkylfluorene-2,7-biborate or 9,9-spirobifluorene-2,7-biborate and their derivatives.

3. Preparation of Dibromonaphthalimide Derivative Monomer dibromonaphthalimide derivative monomer mainly includes: main chain type dibromonaphthalimide derivative monomers, pendant chain type dibromonaphthalimide derivative monomers and pendant chain type 9,9-disubstituted dibromofluorene naphthalimide derivative monomers;

1) The general structural formula of the main chain type dibromonaphthalimide derivative monomers is as follows:

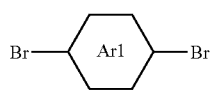

wherein Ar1 is the same as the Ar1 in the main chain type single white light polymeric material.

The preparation method for the main chain type dibromonaphthalimide derivative monomers is as follows:

Naphthalimide derivative Ar1 and 2-10 mole equivalents of tetra-n-butylammonium tribromide are dissolved in dichloromethane. After reacting at 0-40° C. for 10-1200 min, the reaction product is poured into water, and the organic phase is separated, washed repeatedly with water, dried, concentrated and recrystallized to obtain a main chain type dibromonaphthalimide derivative monomer.

2) Pendant chain type dibromonaphthalimide derivative monomer:

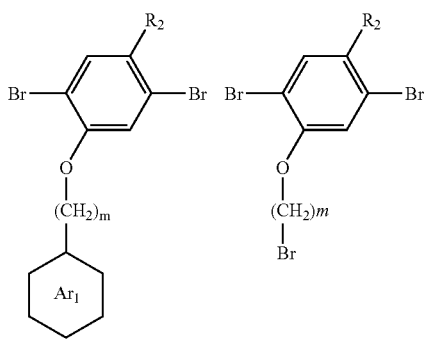

wherein Ar1 is the same as the Ar1 in the pendant chain type single white light polymeric material.

The preparation method for the pendant chain type dibromonaphthalimide derivative monomer is as follows:

First, 2-hydroxy-5-substituted-1,4-dibromobenzene and 1-3 mole equivalents of dibromoalkane with a chain segment number of m are dissolved in anhydrous ethanol, and refluxed in the presence of a solution of 1-10 mole equivalents of KOH for 2-10 hr to obtain 2-(m-bromoalkoxy)-5-substituted-1,4-dibromobenzene as above. Naphthalimide derivative Ar1 and 1-5 mole equivalents of 2-(m-bromoalkoxy)-5-substituted-1,4-dibromobenzene are dissolved in dimethyl sulfoxide. A solution of 1-10 mole equivalents of NaOH is added. After reacting at 20-150° C. for 1-5 days, the reaction is stopped with water. The organic phase is separated, washed repeatedly with water, dried, concentrated and separated by column chromatography to obtain a pendant chain type dibromonaphthalimide derivative monomer.

3) Pendant chain type 9,9-disubstituted dibromofluorene naphthalimide derivative monomer.

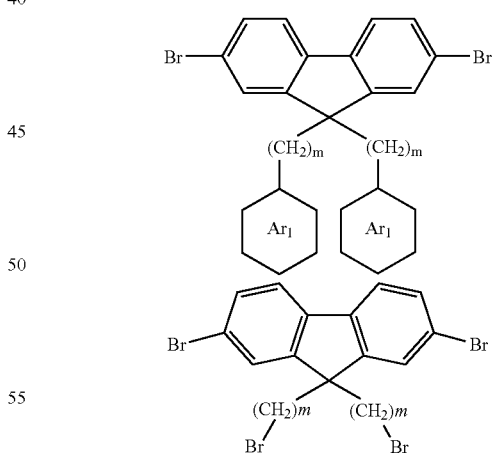

wherein Ar1 is the Ar1 in the pendant chain type single white light polymeric material.

Pendant chain type 9,9-disubstituted dibromofluorene naphthalimide derivative monomer mainly includes: (1) pendant chain type 9,9-dialkyl substituted dibromofluorene naphthalimide derivative monomer, and (2) pendant chain type 9,9-diaryl substituted dibromofluorene naphthalimide derivative monomer.

(1) The preparation method for pendant chain type 9,9-dialkyl substituted dibromofluorene naphthalimide derivative monomer is as follows:

First, 2,7-dibromofluorene and 2-6 mole equivalents of dibromoalkane with a chain segment of $(CH_2)m$ are dissolved in toluene, and 10-70% aqueous solution of 2-50 mole equivalents of NaOH is then added. The reaction system reacted at 30-100° C. under the protection of $N_2$ gas for 1-24 hr to obtain 9,9-(m-bromoalkyl)-2,7-dibromofluorene with the above structure. Then, naphthalimide derivative Ar1 and 1-5 mole equivalents of 9,9-(m-bromoalkyl)-2,7-dibromofluorene are dissolved in DMSO. After adding a solution of 1-10 mole equivalents of NaOH and reacting at 20-150° C. for 1-5 days, the reaction is stopped with water, the organic phase is separated, washed repeatedly with water, dried, concentrated, and separated by column chromatography to obtain pendant chain type 9,9-dialkyl substituted dibromofluorene naphthalimide derivative monomer.

(2) The preparation method for the pendant chain type 9,9-diaryl substituted dibromofluorene naphthalimide derivative monomer is as follows:

First, N,N-diphenyl-1,8-naphthalimide derivative reacted with a solution of 2-40 mole equivalents of phosphorus oxychloride ($POCl_3$) in dimethyl formamide (DMF) at −50~0° C.(low-temperature) for 2-10 hr to produce 4-aldo or 4,4'-dialdo-N,N-diphenyl-1,8-naphthalimide derivative. Then, the resulting product and 1-4 mole equivalents of 9-phenyl-9-(4-bromotributylphosphino-methylenephenyl)-2,7-dibromofluorene or 9,9-(4-bromotributylphosphino-methylenephenyl)-2,7-dibromofluorene are dissolved in a chloroform solution. And a solution of 1-10 mole equivalents of sodium ethoxide is then added. After reacting at 0-60° C. for 1-120 hr, the reaction product is poured into water, and the organic phase is separated, washed repeatedly with water, dried, concentrated, and finally separated by column chromatography to obtain pendant chain type 9,9-diaryl substituted dibromofluorene naphthalimide derivative monomer.

4. Preparation of Monobromonaphthalimide Derivative Monomer

The general structural formula of monobromonaphthalimide derivative monomer is as follows:

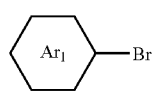

wherein Ar1 is the same as the Ar1 in the terminal group type single white light polymeric material.

The preparation method for monobromonaphthalimide derivative monomer is as follows:

Naphthalimide derivative Ar1H and 1-5 mole equivalents of tetra-n-butylammonium tribromide are dissolved in dichloromethane. After reacting at 0-40° C. for 10-1200 min, the reaction product is poured into water, and the organic phase is separated, washed repeatedly with water, dried, concentrated and recrystallized to obtain monobromonaphthalimide derivative monomer.

5. Preparation of Dibromoaromatic Monomer and Oligomer

The general structural formula of dibromoaromatic monomer and oligomer is as follows:

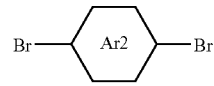

wherein Ar2 is the same as the Ar2 in the main chain type, pendant chain type and terminal group type polymeric structures.

The preparation method and reaction conditions are the same as those of 2,7-dibromofluorene and its derivative monomer.

6. Preparation of White Electroluminescent Polymeric Material

1) Preparation of main chain type white light polymeric material

The main chain type white light polymeric material is prepared using Yamamoto or Suzuki polymerizations.

(1) Yamamoto Polymerization

Under the protection of $N_2$ gas, 1 mol of 2,7-dibromofluorene derivative monomer, 0.01-50 mol % of dibromonaphthalimide derivative monomer and 0-50 mol % of dibromoaromatic monomer are dissolved in anhydrous toluene. Then the resulted solution is dropped into a DMF solution of 1-5 mole equivalents of Ni (0). After reacting at 50-100° C. for 20-200 hr, the reaction is stopped with a mixed solution of methanol and concentrated HCl, and the reaction product is extraction-separated, concentration precipitated, extracted by solvent and vacuum-dried to produce a fibrous polymeric luminescent material.

(2) Suzuki Polymerization 1 mol of 9,9-disubstituted-2,7-biborate derivative monomer, 0.01-50 mol % of dibromonaphthalimide derivative monomer and 0-50 mol % of dibromoaromatic monomer were dissolved in toluene, then 2.0M solution of 5-20 mole equivalents of potassium carbonate is added. Under the protection of $N_2$ gas and at 50-100° C., 0.05-10 mol % of tetrakis (triphenylphosphine) palladium (0) is added. After reacting for 20-200 hr, the reaction is stopped with 0.1M diluted HCl solution. And the reaction product is chloroform-extracted, methanol-settled, solvent-extracted and vacuum-dried to obtain a fibrous polymeric material.

2) Preparation of Pendant Chain Type White Light Polymeric Material

The preparation methods for pendant chain type white light polymeric material using Yamamoto and Suzuki polymerizations separately are the same as those of the main chain type white tight polymeric material, except that dibromonaphthalimide derivative monomer is substituted by pendant chain type dibromonaphthalimide derivative monomer or pendant chain type 9,9-disubstituted dibromofluorene naphthalimide derivative monomer.

3) Preparation of Terminal Group Type White Light Polymeric Material

The terminal group type white light polymeric material is prepared using Yamamoto or Suzuki polymerizations.

(1) Yamamoto Polymerization

Under the protection of $N_2$ gas, 2,7-dibromofluorene derivative monomer and 0-50 mol % of dibromoaromatic monomer Ar2 are dissolved in anhydrous toluene, then the resulting solution is dropped into a DMF solution of 1-5 mole equivalents of Ni (0). After reacting at 50-100° C. for 20-200 hr, 0.01-10 mol % of monobromonaphthalimide derivative monomer is added. After reacting at 50-100° C. for further 1-50 hr, the reaction is stopped with a mixed solution of methanol and concentrated HCl, and the reaction product is extraction-separated, concentration-precipitated, solvent-extracted and vacuum-dried to obtain a fibrous polymeric luminescent material.

(2) Suzuki Polymerization 1 mol of 9,9-disubstituted-2,7-biborate derivative monomer and 0-50 mol % of dibromoaromatic monomer Ar2 are dissolved in toluene, then 2.0M solution of 5-20 mole equivalents of potassium carbonate is added. Under the protection of $N_2$ gas and at 50-100° C., 0.05-10 mol % of tetrakis(triphenylphosphine) palladium (0) is added. After reaction for 1-200 hr, 0.01-10 mol % of monobromonaphthalimide derivative monomer Ar1 is added, and reacted at 50-100° C. for further 1-50 hr. The reaction is terminated with 0.1M diluted HCl solution, then the reaction product is chloroform-extracted, methanol-settled, solvent-extracted, and vacuum-dried to obtain a fibrous polymeric material.

EXAMPLES

Example 1

Synthesizing of
4-bromo-9-(4-t-butylphenyl)-1,8-naphthalimide

Under the protection of $N_2$ gas, 4-bromo-1,8-naphthalic anhydride (10.0 g, 36.2 mmol), p-t-butyl aniline (6.0 g, 40.1 mmol) were added into a reacting flask containing 120 ml of acetic acid as a solvent. After reacting while magnetic stirring at 130° C. for 10 hr, the reaction product was poured into water, filtered, washed repeatedly, and separated by column chromatography. 8.10 g (yield 55%) of a white solid 4-bromo-9-(4-t-butylphenyl)-1,8-naphthalimide was obtained. $^1$H NMR (CDCl$_3$, 300 MHz) δ 8.68(d, 1H), 8.59(d, 1H), 8.43(d, 1H), 8.04(d, 1H), 7.86 (t, 1H), 7.56 (d, 2H), 7.23 (d, 2H), 1.38 (s, 9H).

Example 2

Synthesizing of 4-N,N-diphenyl-9-(4-t-butylphenyl)-1,8-naphthalimide

Under the protection of $N_2$ gas, 3 ml of DMPU solvent was added into a mixture of 4-bromo-9-(4-t-butylphenyl)-1,8-naphthalimide (4.48 g, 11.0 mmol), diphenylamine (1.69 g, 10.0 mmol), anhydrous potassium carbonate (1.53 g, 11.0 mmol), cuprous iodide (0.096 g, 0.50 mmol), and 18-crown-6 (0.13 g, 0.50 mmol). After reacting while magnetic stirring at 190° C. for 20 hr, the reaction product was extracted with dichloromethane, acid washed, ammonia liquor washed, water washed repeatedly, and separated by column chromatography. 1.74 g (yield 35%) of an orange red solid 4-N,N-phenyl-9-(4-t-butylphenyl)-1,8-naphthalimide was obtained. $^1$H NMR (CDCl$_3$, 300 MHz) δ 8.61(d, 1H), 8.54(d, 1H), 8.22(d, 1H), 7.57-7.50 (m, 3H), 7.40 (d, 1H), 7.30-7.22(d, 6H), 7.11-7.04 (m, 6H), 1.38 (s, 9H).

Example 3

Synthesizing of 4-N,N-di(4-bromophenyl)-9-(4-t-butylphenyl)-1,8-naphthalimide

4-N,N-diphenyl-9-(4-t-butylphenyl)-1,8-naphthalimide (1.49 g, 3.0 mmol), tetra-n-butylammonium tribromide (3.16 g, 6.6 mmol) were dissolved in 50 ml of dichloromethane. After reacting at room temperature for 10 min, the reaction product was poured into water. The organic layer, after washing repeatedly, was separated by column chromatography. 1.91 g (yield 97%) of an orange red solid (pure intermediate product)-4-N,N-di(4-bromophenyl)-9-(4-t-butylphenyl)-1, 8-naphthalimide was obtained. $^1$H NMR (CDCl$_3$, 300 MHz) δ 8.60(d, 1H), 8.55(t, 1H), 8.16(d, 1H), 7.60(d, 1H), 7.56(d, 2H), 7.42-7.37 (m, 5H), 7.22(d, 2H), 6.90(d, 4H), 1.38 (s, 9H).

Example 4

Synthesizing of
4-carbazolyl-9-(4-t-butylphenyl)-1,8-naphthalimide

Under the protection of $N_2$ gas, 3 ml of DMPU solvent was added into a mixture of 4-bromo-9-(4-t-butylphenyl)-1,8-naphthalimide (4.48 g, 11.0 mmol), carbazole (1.67 g, 10.0 mmol), anhydrous potassium carbonate (1.53 g, 11.0 mmol), cuprous iodide (0.096 g, 0.50 mmol) and 18-crown-6 (0.13 g, 0.50 mmol). After reacting while magnetic stirring at 190° C. for 20 hr, the reaction product was extracted with dichloromethane, washed with acid, washed with ammonia liquor, washed with water repeatedly, and separated by column chromatography. 1.22 g (yield 25%) of a yellow solid pure 4-carbazolyl-9-(4-t-butylphenyl)-1,8-naphthalimide was obtained. $^1$H NMR (CDCl$_3$, 300 MHz): δ 8.85 (d, 1H), 8.7 (d, 1H), 8.45 (d, 1H), 7.57-7.50 (m, 3H), 7.40 (d, 1H), 7.30-7.22 (d, 6H), 7.00 (m, 4H), 1.38 (s, 9H).

Example 5

Synthesizing of 4-(4,4'-dibromocarbazolyl)-9-(4-t-butylphenyl)-1,8-naphthalimide 4-carbazolyl-9-(4-t-butylphenyl)-1,8-naphthalimide (0.99 g, 2.0 mmol) and tetra-n-butylammonium tribromide (2.10 g, 4.4 mmol) were dissolved in 30 ml of dichloromethane. After reacting at room temperature for 20 hr, the reaction product was poured into water. The organic layer, after washing repeatedly, was separated by column chromatography (dichloromethane). 1.24 g (yield 95%) of a yellow solid (pure intermediate product) 4-(4,4'-dibromocarbazolyl)-9-(4-t-butylphenyl)-1,8-naphthalimide was obtained. $^1$H NMR (CDCl3, 300 MHz): δ 8.85 (d, 1H), 8.72 (d, 1H), 8.28 (d, 1H), 7.91 (d, 1H), 7.68 (m, 2H), 7.60 (m, 2H), 7.50 (d, 2H), 7.25 (d, 1H), 6.90 (d, 2H), 1.38 (s, 9H).

Example 6

Synthesizing of 4-N,N-di(4-aldophenyl)-9-(4-t-butylphenyl)-1,8-naphthalimide

In a cryohydric bath, POCl$_3$ (32.8 g, 214 mmol) was dropped in DMF (15.6 g, 214 mmol). After stirring for 30 min, a solution of 4-N-(4-aldophenyl)-4-N-phenyl-9-(4-t-butylphenyl)-1,8-naphthalimide (1.40 g, 2.67 mmol) in DMF was then dropped in. After reacting for 82 hr at the temperature increased gradually to 97° C., the reaction product was washed with water, extracted by dichloromethane, cleaned repeatedly, dried, filtered, and separated by column chromatography. 0.34 g (yield 23%) of a product was obtained. $^1$H NMR (CDCl₃, 300 MHz) δ 9.93(s, 2H), 8.67(m, 2H), 8.11(d, 1H), 7.82 (d, 4H), 7.74-7.52 (m, 6H), 7.19(d, 4H), 1.38 (s, 9H).

Example 7

Synthesizing of 4-N,N-di(4-bromostyryl)phenyl)-9-(4-t-butylphenyl)-1,8-naphthalimide 4-N,N-di(4-aldophenyl)-9-(4-t-butylphenyl)-1,8-naphthalimide (0.34 g, 0.62 mmol) and 4-bromo-tributylphosphine bromide methylene benzene (0.62 g, 1.37 mmol) were dissolved in chloroform (20 ml), then a solution (5 ml) of metallic sodium (0.091 g, 3.91 mmol) in ethanol was dropped in. After reacting at room temperature for 10 hr, diluted HCl solution was added to stop the reaction. The reaction product was extracted by chloroform, washed repeatedly, dried, filtered, and separated by column chromatography. 0.37 g (yield 69%) of a product was obtained. $^1$H NMR (CDCl₃, 300 MHz) δ 8.59(d, 1H), 8.54(t, 1H), 8.20(d, 1H), 7.58-7.53 (m, 3H), 7.48-7.34 (m, 11H), 7.24-6.88(m, 11H), 6.58-6.47(m, 1H), 1.38 (s, 9H).

Example 8

Synthesizing of 4-N,N-(4,4'-di(4-p-tolylphenylamino)phenyl)-9-(4-t-butylphenyl)-1,8-naphthalimide Under the protection of N₂ gas, 4-N,N-di(4-bromophenyl)-9-(4-t-butylphenyl)-1,8-naphthalimide (0.65 g, 0.99 mmol), 4-N,N-p-tolylphenyl aminophenyl pinacolyl borate (0.85 g, 2.2 mmol), anhydrous potassium carbonate (1.60 g, 0.9 mmol), toluene (10 ml), and a mixture of water (10 ml) and Pd catalyst (30 mg) were added into a reacting flask. After reacting while magnetic stirring at 80° C. for 48 hr, the reaction product was extracted with dichloromethane, washed once with 1N HCl solution, washed with ammonia liquor till the water layer became colorless, washed repeatedly with water, dried with anhydrous Na₂SO₄, concentrated, and separated by silica gel column chromatography. 0.69 g (yield 69%) of a red solid was obtained. $^1$H NMR (CDCl₃, 300 MHz) δ 8.58 (m, 2H), 8.29(d, 1H), 7.59-7.43(m, 12H), 7.28-7.23(m, 7H), 7.15-7.01(m, 21H), 2.87 (s, 6H), 1.40 (s, 9H).

Example 9

Synthesizing of 4-N,N-(4,4'-di(4-p-tolyl-4-bromophenylamino)phenyl)-9-(4-t-butylphenyl)-1,8-naphthalimide 4-N,N-(4,4'-di(4-p-tolylphenylamino)phenyl)-9-(4-t-butylphenyl)-1,8-naphthalimide (0.51 g, 0.50 mmol) and tetra-n-butylammonium tribromide (0.53 g, 1.1 mmol) were dissolved in dichloromethane (10 ml). After reacting at room temperature for 10 min, the reaction product was poured into water. The organic layer, after washed with water repeatedly, was separated by column chromatography. 0.55 g (yield 95%) of an orange red solid was obtained. $^1$H NMR (CDCl₃, 300 MHz) δ 8.57(m, 2H), 8.27(d, 1H), 7.56-7.40(m, 12H), 7.25-7.20(m, 7H), 7.14-7.01(m, 19H), 2.87 (s, 6H), 1.39 (s, 9H).

Example 10

Synthesis of 9-phenyl-9-(4-bromomethylphenyl)-2,7-dibromofluorene

Into a flask, 9-phenyl-9-(4-methylphenyl)-2,7-dibromofluorene (0.90 g, 1.84 mmol), NBS (0.33 g, 1.84 mmol), BPO (0.044 g, 0.184 mmol) and CCl₄ (10 ml) were added and reacted under reflux for 2 hr. Then, the reaction system was cooled and filtered. After removing the filtrate, a gray solid of 9-phenyl-9-(4-bromomethylphenyl)-2,7-dibromofluorene (0.94 g) was obtained as a pure intermediate product (yield, 90%). $^1$HNMR (300 MHz, CDCl₃): δ 7.51-7.48 (m, 6H), 7.26-7.00 (M, 9H), 4.46 (s, 2H).

Example 11

Synthesis of 9-phenyl-9-(4-bromotributylphosphino-methylenephenyl)-2,7-dibromofluorene Into a flask, tributyl phosphorous (0.65 ml, 2.55 mmol) was heated to 100° C. under N2 gas, then a mixture solution of 9-phenyl-9-(4-bromomethylphenyl)-2,7-dibromofluorene (1.00 g, 1.76 mmol) and DMF (15 ml) was dropwisely added. The reaction system was heated to 140° C. to react for 24 hr, then cooled to room temperature, poured into ethyl ether and stirred. Repeated for three times. A gray powder of 9-phenyl-9-(4-bromotributylphosphino-methylenephenyl)-2,7-dibromofluorene (0.89 g) was obtained as a pure intermediate product (yield, 64%). $^1$HNMR (300 MHz, CDCl₃): δ 7.50-7.47 (m, 6H), 7.24-6.98 (M, 9H), 4.26-4.21 (d, 2H), 2.34 (t, 6H), 1.45(m, 12H), 0.98-0.94(t, 18H).

Example 12

Synthesis of 9-phenyl-9-((4-N-(4-(4'-styryl)phenyl)-4-N-phenyl-9-(4-tributylphenyl)-1,8-naphthalimide 9-phenyl-9-(4-bromotributylphosphino-methylenephenyl)-2,7-dibromofluorene (0.49 g, 0.64 mmol) and 4-N-(4-aldophenyl)-4-N-phenyl-9-(4-tributylphenyl)-1,8-naphthalimide (0.34 g, 0.64 mmol) was dissolved in chloroform (15 ml). And then a solution of metal sodium (0.058 g, 2.560 mmol) in ethanol (5 ml) was dropwisely added. Reacted for 10 hr at room temperature. Then a dilute hydrochloride solution is added to terminate the reaction. After extracted with chloroform, the product was washed repeatedly, dried, filtered and separated by column chromatography to obtain a red solid of 9-phenyl-9-((4-N-(4-(4'-styryl)phenyl-4-N-phenyl-9-(4-tributylphenyl)-1,8-napthalimide)-2,7-dibromofluorene (0.46 g, yield, 72%) as a pure intermediate product. $^1$HNMR (300 MHz, CDCl₃): δ 8.57 (d, 1H), 8.52 (d, 1H), 8.20 (d, 1H), 7.58-6.50 (M, 32H), 1.38 (s, 9H).

Example 13

Synthesis of 4-N-(4-aldophenyl)-4-N-(4-(4-styryl)phenyl)-9-(4-tributylphenyl)-1,8-naphthalimide bromotributylphosphinomethylenephenyl (0.37 g, 1.00 mmol) and 4-N,N-di(4-aldophenyl)-9-(4-tributylphenyl)-1, 8-naphthalimide (0.55 g, 1.00 mmol) was dissolved in chloroform (25 ml). And then a solution of metal sodium (0.092 g, 4.000 mmol) in ethanol (5 ml) was dropwisely added. Reacted for 20 hr at room temperature. Then a dilute hydrochloride solution is added to terminate the reaction. After extracted with chloroform, the product was washed repeatedly, dried, filtered and separated by column chromatography to obtain a red solid of 4-N-(4-aldophenyl)-4-N-(4-(4'-styryl) phenyl)-9-(4-tributylphenyl)-1,8-naphthalimide (0.41 g, yield, 65%) as a pure intermediate product. $^1$HNMR (300 MHz, CDCl$_3$): δ 8.57 (d, 1H), 8.52 (d, 1H), 8.20 (d, 1H), 7.58-6.50 (M, 32H), 1.38 (s, 9H).

Example 14

Synthesis of 9-phenyl-9-((4-N-(4-(4'-styryl)phenyl)-4-N-((4'-styryl)phenyl)-9-(4-tributylphenyl) -1,8-naphthalimide)-2,7-dibromofluorene 9-phenyl-9-(4-bromotributylphosphino-methylenephenyl)-2,7-dibromofluorene (0.61 g, 0.80 mmol) and 4-N-(4-aldophenyl)-4-N-(4-(4'-styryl)phenyl)-9-(4-tributylphenyl)-1,8-naphthalimide (1.00 g, 1.60 mmol) was dissolved in chloroform (20 ml). And then a solution of metal sodium (0.185 g, 8.0 mmol) in ethanol (5 ml) was dropwisely added. Reacted for 50 hr at room temperature. Then a dilute hydrochloride solution is added to terminate the reaction. After extracted with chloroform, the product was washed repeatedly, dried, filtered and separated by column chromatography to obtain a red solid of 9-phenyl-9-((4-N-(4-(4'-styryl)phenyl)-4-N-((4'-styryl)phenyl)-9-(4-tributylphenyl) -1,8-naphthalimide)-2,7-dibromofluorene (0.62 g, yield, 70%) as a pure intermediate product. $^1$HNMR (300 MHz, CDCl$_3$): δ 8.57 (d, 1H), 8.52 (d, 1H), 8.20 (d, 1H), 7.58-6.50 (m, 38H), 1.38 (s, 9H).

Example 15

Synthesis of 2-(2'-(4'-amino-1',8'-naphthalimide-9'-alkyl)ethoxyl)-5-hexoxyl-1,4-dibromobenzene Under protection of N2 gas, 4-amino-1,8-naphthalimide (1.06 g, 5 mmol) was dissolved in dimethyl sulfoxide (60 ml). Into the resulting solution, powdered KOH (2.8 g, 50 mmol) was added. The reaction was carried out at 150° C. for 10 min while magnetic stirring, and then 2-(2-bromoethoxyl)-5-hexoxyl-1,4-dibromobenzene (2.31 g, 5 mmol) was added stepwisely. After reacting for 1 hr, the resulting product was extracted with chloroform, washed repeatedly, dried, filtered, and separated by column chromatograph to obtain a pure intermediate product (2.06 g, yield, 70%). $^1$H NMR (CDCl$_3$, 300 MHz) δ 8.63 (d, 1H), 8.44 (d, 1H), 8.12 (d, 1H), 7.67 (t, 1H), 7.20 (s, 1H), 7.01 (s, 1H), 6.90 (d, 1H), 4.65 (t, 2H), 4.29 (t, 2H), 3.90 (t, 2H), 1.81-1.29 (m, 8H), 0.87 (t, 3H).

Example 16

Synthesis of 2-(2'-(4'-dianilino-1',8'-naphthalimide-9'-alkyl)ethoxyl)-5-hexoxyl-1,4-dibromobenzene Under protection of N2 gas, 2-(2'-(4'-amino-1',8'-naphthalimide-9'-alkyl)ethoxyl)-5-hexoxyl-1,4-dibromobenzene (0.589 g, 1.0 mmol), iodobenzene (0.41 g, 2.0 mmol), potassium carbonate (0.28 g, 2.0 mmol), 18-crown-6 (0.003 g, 0.01 mmol), cuprous iodide (0.002 g, 0.01 mmol) and DMPU (0.30 ml) were heated to 200° C. and reacted for 5 hr. After extracted with chloroform, the product was washed repeatedly, dried, filtered, and separated by column chromatography to obtain a red solid (0.33 g, yield, 45%). $^1$H NMR (CDCl$_3$, 300 MHz) δ 8.54 (d, 1H), 8.51 (d, 1H), 7.50 (t, 1H), 7.37 (d, 1H), 7.25-6.90 (m, 13H), 4.68 (t, 2H), 4.30 (t, 2H), 3.90 (t, 2H), 1.77 (m, 2H), 1.47-1.25 (m, 6H), 0.87 (t, 3H).

Example 17

Synthesis of 2-(12'-(4'-amino-1',8'-naphthalimide-9'-alkyl)dodecoxyl-5-hexoxyl-1,4-dibromobenzene Under protection of N2 gas, 4-amino-1,8-naphthalimide (1.06 g, 5 mmol) was dissolved in dimethyl sulfoxide (60 ml). Into the resulting solution, powdered KOH (0.28 g, 5 mmol) was added. The reaction was carried out at 50° C. for 10 min while magnetic stirring, and then 2-(12-bromododecoxyl)-5-hexoxyl-1,4-dibromobenzene (30.0 g, 50 mmol) was added stepwisely. After reacting for 120 hr, the resulting product was extracted with chloroform, washed repeatedly, dried, filtered, and separated by column chromatograph to obtain a pure intermediate product (2.906 g, yield, 81%). $^1$H NMR (CDCl$_3$, 300 MHz) δ 8.60 (d, 1H), 8.42 (d, 1H), 8.10 (d, 1H), 7.66 (t, 1H), 7.06 (s, 2H), 6.89 (d, 1H), 4.93 (s, 2H), 4.18 (t, 2H), 3.94 (t, 4H), 1.80-1.25 (m, 28H), 0.92 (t, 3H).

Example 18

Synthesis of 2-(12'-(4'-dianilino-1',8'-naphthalimide-9-alkyl)dodecoxyl)-5-hexoxyl-1,4-dibromobenzene Under protection of N$_2$ gas, 2-(12'-(4'-amino-1',8'-naphthalimide-9'-alkyl)dodecoxyl)-5-hexoxyl-1,4-dibromobenzene (0.7369 g, 1.0 mmol), iodobenzene (4.08 g, 10.0 mmol), potassium carbonate (2.8 g, 20.0 mmol), 18-crown-6 (0.015 g, 0.05 mmol), cuprous iodide (0.0095 g, 0.05 mmol) and DMPU (0.30 ml) were heated to 140° C. and reacted for 50 hr. After extracted with chloroform, the product was washed repeatedly, dried, filtered, and separated by column chromatography to obtain a red solid (0.283 g, yield, 33%). $^1$H NMR (CDCl$_3$, 300 MHz) δ 8.57 (d, 1H), 8.48 (d, 1H), 8.44 (d, 1H), 7.66 (t, 1H), 7.28-7.01 (m, 13H), 4.18 (t, 2H), 3.94 (t, 4H), 1.79-1.25 (m, 28H), 0.91 (t, 3H).

Example 19

Synthesis of 9,9-di(2-(4-amino-1,8-naphthalimide-9)-ethyl)-2,7-dibromofluorene

Under protection of N$_2$ gas, 4-amino-1,8-naphthalimide (1.06 g, 5 mmol) was dissolved in dimethyl sulfoxide (60 ml). Into the resulting solution, powdered KOH (2.8 g, 50 mmol) was added. The reaction was carried out at 150° C. for 10 min while magnetic stirring, and then 9,9-di(2-bromoethyl)-2,7-dibromofluorene (1.34 g, 2.5 mmol) was added stepwisely. After reacting for 1 hr, the resulting product was extracted with chloroform, washed repeatedly, dried, filtered, and separated by column chromatograph to obtain a pure intermediate product (1.40 g, yield, 70%). $^1$H NMR (CDCl$_3$, 300 MHz) δ 8.59 (d, 2H), 8.39 (d, 2H), 8.09 (d, 2H), 7.65 (t, 2H), 7.52-7.04 (m, 6H), 6.90 (d, 2H), 3.90 (t, 4H), 2.17 (t, 4H).

Example 20

Synthesis of 9,9-di(2-(4-dianilino-1,8-naphthalimide-9-)ethyl)-2,7-dibromofluorene Under protection of N$_2$ gas, 9,9-di(2-(4-amino-1,8-naphthalimide-9-)ethyl)-2,7-dibromofluorene (0.400 g, 0.5 mmol), iodobenzene (0.41 g, 2.0 mmol), potassium carbonate (0.414 g, 3.0 mmol), 18-crown-6 (0.015 g, 0.05 mmol), cuprous iodide (0.0095 g, 0.05 mmol) and DMPU (0.30 ml) were heated to 200° C. and reacted for 5 hr. After extracted with chloroform, the product was washed repeatedly, dried, filtered, and separated by column chromatography to obtain a red solid (0.138 g, yield, 25%). $^1$H NMR (CDCl$_3$, 300 MHz) δ 8.48 (t, 4H), 8.15 (d, 2H), 7.65 (d, 2H), 7.57 (s, 2H), 7.50-7.00 (m, 16H), 3.90 (t, 4H), 2.17 (t, 4H).

Example 21

Synthesis of 9,9-di(12-(4-amino-1,8-naphthalimide-9-)dodecyl)-2,7-dibromofluorene Under protection of N$_2$ gas, 4-amino-1,8-naphthalimide (1.6 g, 7.5 mmol) was dissolved in dimethyl sulfoxide (60 ml). Into the resulting solution, powdered KOH (0.28 g, 5 mmol) was added. The reaction was carried out at 50° C. for 10 min while magnetic stirring, and then 9,9-di(12-bromododecyl)-2,7-dibromofluorene (2.04 g, 2.5 mmol) was added stepwisely. After reacting for 120 hr, the resulting product was extracted with chloroform, washed repeatedly, dried, filtered, and separated by column chromatograph to obtain a pure intermediate product (2.00 g, yield, 74%). $^1$H NMR (CDCl$_3$, 300 MHz) δ 8.58 (d, 2H), 8.38 (d, 2H), 8.07 (d, 2H), 7.63 (t, 2H), 7.50-7.00 (m, 6H), 6.90 (d, 2H), 4.07 (t, 4H), 1.92 (t, 4H), 1.77-1.20 (m, 16H).

Example 22

Synthesis of 9,9-di(12-(4-dianilino-1,8-naphthalimide-9-)dodecyl)-2,7-dibromofluorene Under protection of N$_2$ gas, 9,9-di(2-(4-amino-1,8-naphthalimide-9-)dodecyl)-2,7-dibromofluorene (0.540 g, 0.5 mmol), iodobenzene (2.04 g, 10 mmol), potassium carbonate (1.38 g, 10 mmol), 18-crown-6 (0.003 g, 0.01 mmol), cuprous iodide (0.002 g, 0.01 mmol) and DMPU (0.30 ml) were heated to 140° C. and reacted for 50 hr. After extracted with chloroform, the product was washed repeatedly, dried, filtered, and separated by column chromatography to obtain a red solid (0.221 g, yield, 32%). $^1$H NMR (CDCl$_3$, 300 MHz) δ 8.47 (t, 4H), 8.14 (d, 2H), 7.63 (d, 2H), 7.55 (s, 2H), 7.50-7.00 (m, 16H), 4.07 (t, 4H), 1.92 (t, 4H), 1.77-1.20 (m, 16H).

Example 23

Synthesis of 2-(6'-(4'-amino-1',8'-naphthalimide-9'-alkyl)hexoyl)-5-hexoxyl-1,4-dibromobenzene Under protection of N$_2$ gas, 4-amino-1,8-naphthalimide (2.02 g, 10 mmol) was dissolved in dimethyl sulfoxide (60 ml). Into the resulting solution, powdered KOH (0.56 g, 10 mmol) was added. The reaction was carried out at 120° C. for 10 min while magnetic stirring, and then 2-(6-bromohexoxyl)-5-hexoxyl-1,4-dibromobenzene was added stepwisely. After reacting for 14 hr, the resulting product was extracted with chloroform, washed repeatedly, dried, filtered, and separated by column chromatograph to obtain a pure intermediate product (3.94 g, yield, 61%). $^1$H NMR (CDCl$_3$, 300 MHz) δ 8.63 (d, 1H), 8.44 (d, 1H), 8.12 (d, 1H), 7.67 (t, 1H), 7.20 (s, 1H), 7.01 (s, 1H), 6.90 (d, 1H), 4.18 (t, 2H), 3.94 (t, 4H), 1.81-1.29 (m, 16H), 0.87 (t, 3H)

Example 24

Synthesis of 2-(6'-(4'-dianilino-1',8'-naphthalimide-9'-alkyl)hexoyl)-5-hexoxyl-1,4-dibromobenzene Under protection of N$_2$ gas, 2-(6'-(4'-amino-1',8'-naphthalimide-9'-alkyl)hexoyl)-5-hexoxyl-1,4-dibromobenzene (0.618 g, 1.0 mmol), iodobenzene (1.020 g, 5.0 mmol), potassium carbonate (0.414 g, 3.0 mmol), 18-crown-6 (0.015 g, 0.05 mmol), cuprous iodide (0.0095 g, 0.05 mmol) and DMPU (0.30 ml) were heated to 190° C. and reacted for 48 hr. After extracted with chloroform, the product was washed repeatedly, dried, filtered, and separated by column chromatography to obtain a red solid (0.45 g, yield, 57%). $^1$H NMR (CDCl$_3$, 300 MHz) δ 8.55 (d, 1H), 8.46 (d, 1H), 8.44 (d, 1H), 7.63 (t, 1H), 7.30-7.01 (m, 13H), 4.19 (t, 2H), 3.90 (t, 4H), 1.79-1.25 (m, 16H), 0.91 (t, 3H).

Example 25

Synthesis of 1,4-dibromo-2-hexoxyl-5-(6-(4-di(4-iodophenyl-1-)amino-1,8-naphthalimide-9-)-hexoxyl)benzene 1,4-dibromo-2-hexoxyl-5-(6-(4-dianilino-1,8-naphthalimide-9-)-hexoxyl)benzene (3.99 g, 5 mmol) was dissolved in ethanol (30 ml). While stirring, iodine (3.05 g, 12 mmol) was added into the flask in batches. Reacted for 30 min. Then the reaction mixture was poured into water, extracted with chloroform, washed with water, dried, and separated by column chromatography to produce an orange-red solid (4.35 g, yield, 82%). $^1$H NMR (CDCl$_3$, 300 MHz) δ 8.55 (d, 1H), 8.46 (d, 11H), 8.44 (d, 1H), 7.45 (m, 5H), 7.30-7.01 (m, 7H), 4.19 (t, 2H), 3.90 (t, 4H), 1.79-1.25 (m, 16H), 0.91 (t, 3H).

Example 26

Synthesis of 1,4-dibromo-2-hexoxyl-5-(6-(4-di(4'-dianilino-biphenyl-4-)amino-1,8-naphthalimide-9-)-hexoxyl)benzene A mixture of 1,4-dibromo-2-hexoxyl-5-(6-(4-di(4-iodophenyl-1-)amino-1,8-naphthalimide-9-)-hexoxyl)benzene (2.10 g, 2 mmol), triarylamine borate (0.89 g, 2.4 mmol), KF (0.232 g, 4 mmol), tetra(triphenylphosphino)palladium (23 mg, 0.02 mmol), DMF (10 ml), and water (2 ml) was heated to 100° C. to react for 6 hr under N2 gas. The product was extracted with chloroform, water washed, dried, and separated by column chromatography to obtain a red solid (2.31 g, yield, 90%). $^1$H NMR (CDCl$_3$, 300 MHz) δ 8.55 (d, 1H), 8.46 (d, 1H), 8.44 (d, 1H), 7.41 (d, 1H), 7.30-7.01 (m, 21H), 4.00 (t, 2H), 3.69 (t, 4H), 1.79-1.25 (m, 16H), 0.91 (t, 3H).

Example 27

Synthesis of 1,4-dibromo-2-hexoxyl-5-(6-(4-di(4-aldophenyl-1-)amino-1,8-naphthalimide-9-)-hexoxyl)benzene 1,4-dibromo-2-hexoxyl-5-(6-(4-di(4-iodophenyl-1-)amino-1,8-naphthalimide-9-)-hexoxyl)benzene (3.20 g, 4 mmol) was dissolved in DMF (20 ml). Then POCl3 (1.38 g, 9 mmol) was added and the mixture was heated up to 120° C. to react for 10 hr. The product was extracted with chloroform, washed with water, dried, and separated by column chromatography to obtain an orange-red solid (1.81 g, yield, 53%).

¹H NMR (CDCl₃, 300 MHz) δ 8.90 (s, 2H), 8.55 (d, 1H), 8.46 (d, 1H), 8.44 (d, 1H), 7.85 (d, 4H), 7.63 (t, 1H), 7.38-7.01 (m, 7H), 4.19 (t, 2H), 3.90 (t, 4H), 1.79-1.25 (m, 16H), 0.91 (t, 3H).

Example 28

Synthesis of 1,4-dibromo-2-hexoxyl-5-(6-(4-di(4-styrylphenyl-1-)amino-1,8-naphthalimide-9-)-hexoxyl)benzene A mixture of 1,4-dibromo-2-hexoxyl-5-(6-(4-di(4-aldophenyl-1-)amino-1,8-naphthalimide-9-)-hexoxyl)benzene (1.71 g, 2 mmol), bromotributylphosphinomethylenebenzene (1.69 g, 4.5 mmol), sodium (0.192 g, 8 mmol), ethanol (10 ml) and chloroform (10 ml) was stirred at room temperature for 3 hr. The product was extracted with chloroform, washed with water, dried, and separated by column chromatography to obtain an orange-red solid (1.30 g, yield 65%). ¹H NMR (CDCl₃, 300 MHz) δ 8.55 (d, 1H), 8.46 (d, 1H), 8.44 (d, 1H), 7.63 (t, 1H), 7.38-6.87 (m, 17H), 4.19 (t, 2H), 3.90 (t, 4H), 1.79-1.25 (m, 16H), 0.91 (t, 3H).

Example 29

Synthesizing of 4-N-(4-aldophenyl)-4-N-phenyl-9-(4-t-butylphenyl)-1,8-naphthalimide In a cryohydric bath, POCl₃ (15.40 g, 100 mmol) was dropped in DMF (7.30 g, 100 mmol). After stirring under the protection of N₂ gas for 30 min, a solution of 4-N,N-phenyl-9-(4-t-butylphenyl)-1,8-naphthalimide (3.30 g, 6.65 mmol) in DMF was then dropped in. After reacting for 26 hr at the temperature increased gradually to 97° C., the reaction product was washed with water, extracted with dichloromethane, cleaned repeatedly, dried, filtered, and separated by column chromatography. 2.41 g (yield 69%) of a product was obtained. ¹H NMR (CDCl₃, 300 MHz) δ 8.67(d, 1H), 8.64(d, 1H), 8.11(d, 1H), 7.82 (d, 4H), 7.74-7.52 (m, 6H), 7.19(d, 4H), 1.38 (s, 9H).

Example 30

Synthesizing of 4-N-(4-(4'-bromostyryl)phenyl)-4-N-phenyl-9-(4-t-butylphenyl)-1,8-naphthalimide 4-N-(4-aldophenyl)-4-N-phenyl-9-(4-t-butylphenyl)-1,8-naphthalimide (0.20 g, 0.38 mmol), 4-bromo-tributylphosphine bromide methylene benzene (0.17 g, 0.38 mmol) were dissolved in chloroform (8 ml), then a solution (3 ml) of metallic sodium (0.030 g, 1.30 mmol) in ethanol was dropped in. After reacting at room temperature for 10 hr, a diluted HCl solution was added to stop the reaction. The reaction product was extracted by chloroform, washed repeatedly, dried, filtered, and separated by column chromatography. 0.19 g (yield 74%) of a product was obtained. ¹H NMR (CDCl₃, 300 MHz) δ 8.59(d, 1H), 8.54(t, 1H), 8.20(d, 1H), 7.58-7.53 (m, 3H), 7.48-7.34 (m, 1H), 7.24-6.88(m, 11H), 6.58-6.47(m, 1H), 1.38 (s, 9H).

Example 31

Synthesizing of 4-N-(4-methylphenyl)-4-N-phenyl-9-(4-t-butylphenyl)-1,8-naphthalimide Under the protection of N₂ gas, 4-bromo-9-(4-t-butylphenyl)-1,8-naphthalimide (5.00 g, 12.30 mmol), 4-methyl-diphenylamine (2.47 g, 13.50 mmol), anhydrous potassium carbonate (1.86 g, 13.50 mmol), cuprous iodide (0.24 g, 1.23 mmol), and 18-crown-6 (0.31 g, 1.23 mmol) were dissolved in DMPU solvent (3 ml). After reacting while magnetic stirring at 190° C. for 20 hr, the reaction product was extracted with dichloromethane, washed with acid, washed with ammonia liquor, washed with water repeatedly, and separated by column chromatography. 1.87 g (yield 30%) of an orange red solid (as pure intermediate product) 4-N-(4-methylphenyl)-4-N-phenyl-9-(4-t-butylphenyl)-1,8-naphthalimide was obtained. ¹H NMR (300 MHz, CDCl₃): δ 8.57 (d, 1H), 8.52 (d, 1H), 8.20 (d, 1H), 7.57-7.24 (m, 9H), 7.30-6.87 (d, 6H), 2.31(s, 3H), 1.38 (s, 9H).

Example 32

Synthesizing of 4-N-(4-methylphenyl)-4-N-(4-bromophenyl)-9-(4-t-butylphenyl)-1,8-naphthalimide 4-N-(4-methylphenyl)-4-N-phenyl-9-(4-t-butylphenyl)-1,8-naphthalimide (0.54 g, 1.06 mmol), tetra-n-butylammonium tribromide (0.55 g, 1.14 mmol) were dissolved in dichloromethane (10 ml). After reacting at room temperature for 20 min, the reaction product was poured into water, and the organic layer, after washed with water repeatedly, was separated by column chromatography. 0.61 g (yield 98%) of an orange red solid (as a pure final product) 4-N-(4-methylphenyl)-4-N-(4-bromophenyl)-9-(4-t-butylphenyl)-1,8-naphthalimide was obtained. ¹HNMR (300 MHz, CDCl₃): δ 8.59 (d, 1H), 8.54 (d, 1H), 8.21 (d, 1H), 7.58-7.52 (m, 3H), 7.38-7.21 (m, 5H), 7.12-6.85 (d, 6H), 2.31 (s, 3H), 1.38 (s, 9H).

Example 33

Synthesis of 4-N-(4-methylphenyl)-4-N-(4-tolyl-4'-phenylamino)phenyl-9-(4-tributylphenyl)-1,8-naphthalimide Under the protection of N₂ gas, a mixture of 4-N-(4-methylphenyl)-4-N-(4-bromophenyl)-9-(4-tributylphenyl)-1,8-naphthalimide (0.59 g, 1.0 mmol), 4-methyl-4'-trimethyleneborate-yl-trianilino (0.75 g, 2.2 mmol), anhydrous potassium carbonate (1.78 g, 1.0 mmol), tolune (10 ml), water (10 ml) and palladium catalyst (30 mg) was reacted at 80° C. for 48 hr. The product was extracted with CH2Cl2, washed with water, dried, and separated by column chromatography to obtain a red solid of 4-N-(4-methylphenyl)-4-N-(4-tolyl-4'-phenylamino)phenyl-9-(4-tributylphenyl)-1,8-naphthalimide (0.50 g, yield, 65%). ¹HNMR (300 MHz, CDCl₃): δ 8.57 (d, 1H), 8.51 (d, 1H), 8.20 (d, 1H), 7.56-7.50 (m, 3H), 7.38-7.18 (m, 11H), 7.10-6.78 (m, 13H), 2.31 (s, 3H), 2.27 (s, 3H), 1.38 (s, 9H).

Example 34

Synthesis of 4-N-(4-methylphenyl)-4-N-(4-methyl-4'-bromophenylamino)phenyl-9-(4-tributylphenyl)-1,8-naphthalimide 4-N-(4-methylphenyl)-4-N-(4-tolyl-4'-phenylamino)phenyl-9-(4-tributylphenyl)-1,8-naphthalimide (0.77 g, 1.0 mmol) and tetrabutylammonium bromide (0.49 g, 1.0 mmol) were dissolved in CH₂Cl₂ (10 ml) and reacted at room temperature for 10 min. The reaction mixture was poured into water, and the resulting organic layer was washed repeatedly with water. Then the product was separated by column chromatography to obtain a pure product of 4-N-(4-methylphenyl)-4-N-(4-tolyl-4'-bromophenylamino)phenyl-9-(4-tributylphenyl)-1,8-naphthalimide as an orange-red solid (0.83 g, yield 98%). $^1$HNMR (300 MHz, CDCl$_3$): δ 8.58 (d, 1H), 8.53 (d, 1H), 8.22 (d, 1H), 7.58-7.50 (m, 3H), 7.39-7.20 (m, 11H), 7.12-6.77 (m, 12H), 2.32 (s, 3H), 2.29 (s, 3H), 1.39 (s, 9H).

Example 35

Synthesis of 4-N-(4-aldophenyl)-4-N-p-bromophenyl-9-(4-tributylphenyl)-1,8-naphthalimide 4-N-(4-aldophenyl)-4-N-phenyl-9-(4-tributylphenyl)-1,8-naphthalimide (0.52 g, 1.0 mmol) and tributylammonium bromide (0.52 g, 1.07 mmol) were dissolved in CH$_2$Cl$_2$ (10 ml) and reacted at room temperature for 20 min. The reaction mixture was poured into water, and the resulting organic layer was washed repeatedly with water. Then the product was separated by column chromatography to obtain a pure product of 4-N-(4-aldophenyl)-4-N-bromophenyl-9-(4-tributylphenyl)-1,8-naphthalimide as an orange-yellow solid (0.59 g, yield 98%). $^1$H NMR (CDCl$_3$, 300 MHz) δ 9.86(s, 1H), 8.61 (d, 2H), 8.19 (d, 1H), 7.73 (d, 2H), 7.62 (t, 1H), 7.55 (t, 3H), 7.37 (t, 2H), 7.19-7.26 (m, 4H), 7.00 (d, 2H), 1.38 (s, 9H).

Example 36

Synthesis of 4-N-p-bromophenyl-4-N-(4-styryl)phenyl-9-(4-tributylphenyl)-1,8-naphthalimide 4-N-(4-aldophenyl)-4-N-bromophenyl-9-(4-tributylphenyl)-1,8-naphthalimide (0.48 g, 0.80 mmol) and tributylphosphinemethylene benzene chloride (0.29 g, 0.88 mmol) were dissolved in chloroform (15 ml). Then, a solution of metal sodium (0.055 g, 2.40 mmol) in ethanol (3 ml) was dropped in. The reaction was carried out for 10 hr. A diluted hydrochloride solution was added to stop the reaction. Then extracted with chloroform, washed with water, dried, and separated by column chromatography to obtain 4-N-bromophenyl-4-N-(4-styryl)phenyl-9-(4-tributylphenyl)-1,8-naphthalimide as an orange-red solid product (0.38 g, yield 72%). $^1$H NMR (CDCl$_3$, 300 MHz) δ 8.56 (m, 2H), 8.21 (m, 1H), 6.45-7.57 (m, 20H), 1.38 (s, 9H).

Example 37

Synthesizing and Characterizing of Polymeric Electroluminescent Material P1

Under the protection of N$_2$ gas, a mixture of bis(1,5-cyclooctadienyl) nickel (0.56 g, 2.0 mmol), 2,2'-bipyridine (0.22 g, 2.0 mmol), 1,5-cyclooctadiene (0.32 g, 2.0 mmol) and DMF (5 ml) in a reacting flask was reacted at 80° C. for half an hour, then a solution (5 ml) of 9,9'-dioctyl-2,7-dibromofluorene (0.4937 g, 0.90 mmol) and 4-N,N-di(4-bromophenyl)-9-(4-t-butylphenyl)-1,8-naphthalimide (0.066 g, 0.10 mmol) in toluene was added. After reacting at 100° C. for 5 days, the reaction product was poured into a mixture of methanol (100 ml)/acetone (100 ml)/concentrated HCl solution (100 ml) with stirring for 2 hr, filtered, precipitated thrice with methanol, extracted with acetone for 1 day in a Soxhlet extractors, and vacuum dried. 0.24 g (yield 59%) of an orange yellow solid was obtained. $^1$H NMR (300 MHz, CDCl3): δ 7.86-7.68(m, Ar—H), 2.17-1.15(m, CH$_2$), 0.84-0.79(m, CH$_3$). Product performances: number average molecular weight (Mn), 12,000; maximum UV-absorption (film), 380 nm; solid fluorescence emissions, 576 nm.

The assembling conditions of single-layer device (ITO/PEDOT/Polymer/Ca/Al) were as follows: the pre-cleaned ITO glass was used as anode, then a layer (40 nm) of conducting polymer, polythiophene derivative (PEDOT), was spin-coated on the anode. The ITO coated with PEDOT was vacuum dried at 110° C. for 1 hr. Then the chloroform solution containing 10 mg/ml of the polymer was spin-coated on the surface of ITO at 1500 rpm. Then, under high vacuum condition, metallic calcium (10 nm) and metallic aluminum (100 nm) were coated by vaporization. The performances of said single-layer electroluminescent device were as follows: starting voltage, 5.8V; maximum luminance, 2870 cd/m$^2$; maximum efficiency of electroluminescence, 0.8 cd/A; color coordinate, (0.54, 0.35).

Example 38

Synthesizing and Characterizing of Polymeric Electroluminescent Material P2

Under the protection of N$_2$ gas, a mixture of bis(1,5-cyclooctadienyl) nickel (0.84 g, 3.00 mmol), 2,2'-bipyridine (0.33 g, 3.0 mmol), 1,5-cyclooctadiene (0.48 g, 3.00 mmol) and DMF (5 ml) in a reacting flask was reacted at 80° C. for half an hour, then a solution (5 ml) of 9,9'-dioctyl-2,7-dibromofluorene (0.543 g, 0.990 mmol) and 4-N,N-di(4-bromophenyl)-9-(4-t-butylphenyl)-1,8-naphthalimide (0.0067 g, 0.010 mmol) in toluene was added. Reacted at 50° C. for 3 days. The rest steps were the same as those in Example 37. 0.25 g (yield 64%) of an orange yellow solid was obtained. $^1$H NMR (300 MHz, CDCl3): δ 7.88-7.69(m, Ar—H), 2.19-1.16 (m, CH$_2$), 0.84-0.80(m, CH$_3$). Product performances: number average molecular weight (Mn), 20,000; maximum UV-absorption (film), 382 nm; solid fluorescence emissions, 425, 448 and 550 nm.

The assembling conditions of single-layer device were the same as those of Example 37. The performances of said single-layer electroluminescent device were as follows: starting voltage, 6.6V; maximum luminance, 10500 cd/m$^2$; maximum efficiency of electroluminescence, 2.8 cd/A; color coordinate, (0.34, 0.48).

Example 39

Synthesizing and Characterizing of Polymeric Electroluminescent Material P3

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for an hour, then a solution (5 ml) of 9,9'-dioctyl-2,7-dibromofluorene (0.545 g, 0.995 mmol) and 4-N,N-di(4-bromophenyl)-9-(4-t-butylphenyl)-1,8-naphthalimide (0.0033 g, 0.0050 mmol) in toluene was added. Reacted at 80° C. for 1 day. The rest steps were the same as those in Example 37. 0.28 g (yield 72%) of an orange yellow solid was obtained. $^1$H NMR (300 MHz, CDCl3): δ 7.87-7.67(m, Ar—H), 2.15-1.12 (m, CH$_2$), 0.86-0.79(m, CH$_3$). Product performances: number average molecular weight (Mn), 17,000; maximum UV-absorption (film), 380 nm; solid fluorescence emissions, 438, 461 and 550 nm.

The assembling conditions of single-layer device were the same as those of Example 37. The performances of said single-layer electroluminescent device were as follows: starting voltage, 5.8V; maximum luminance, 18300 cd/m$^2$; maximum efficiency of electroluminescence, 3.8 cd/A; color coordinate, (0.29, 0.45).

Example 40

Synthesizing and Characterizing of Polymeric Electroluminescent Material P4

Under the protection of $N_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for 1 hour, then a solution (5 ml) of 9,9'-dioctyl-2,7-dibromofluorene (0.546 g, 0.997 mmol) and 4-N,N-di(4-bromophenyl)-9-(4-t-butylphenyl)-1,8-naphthalimide (0.0020 g, 0.0030 mmol) in toluene was added. Reacted at 80° C. for 2 days. The rest steps were the same as those in Example 37. 0.27 g (yield 70%) of an orange yellow solid was obtained. $^1$H NMR (300 MHz, CDCl3): δ 7.86-7.66(m, Ar—H), 2.18-1.15 (m, $CH_2$), 0.86-0.79(m, $CH_3$). Product performances: number average molecular weight (Mn), 19,000; maximum UV-absorption (film), 382 nm; solid fluorescence emissions, 426, 444 and 542 nm.

The assembling conditions of single-layer device were the same as those of Example 37. The performances of said single-layer electroluminescent device were as follows: starting voltage, 5.4V; maximum luminance, 12900 $cd/m^2$; maximum efficiency of electroluminescence, 4.2 cd/A; color coordinate, (0.29, 0.45).

Example 41

Synthesizing and Characterizing of Polymeric Electroluminescent Material P5

Under the protection of $N_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 85° C. for half an hour, then a solution (5 ml) of 9,9'-dioctyl-2,7-dibromofluorene (0.548 g, 0.9995 mmol) and 4-N,N-di(4-bromophenyl)-9-(4-t-butylphenyl)-1,8-naphthalimide (0.00033 g, 0.00050 mmol) in toluene was added. Reacted at 80° C. for 1 day. The rest steps were the same as those in Example 37. 0.30 g (yield 77%) of an orange yellow solid was obtained. $^1$H NMR (300 MHz, CDCl3): δ 7.85-7.68(m, Ar—H), 2.16-1.15 (m, $CH_2$), 0.84-0.78(m, $CH_3$). Product performances: number average molecular weight (Mn), 30,000; maximum UV-absorption (film), 384 nm; solid fluorescence emissions, 433, 447 and 540 nm.

The assembling conditions of the single-layer electroluminescent device were the same as those of Example 37. The performances of said single-layer electroluminescent device were as follows: starting voltage, 4.8V; maximum luminance, 8820 $cd/m^2$; maximum efficiency of electroluminescence, 3.9 cd/A; color coordinate for a white light, (0.30, 0.40).

Example 42

Synthesizing and Characterizing of Polymeric Electroluminescent Material P6

Under the protection of $N_2$ gas, a mixture of bis(1,5-cyclooctadienyl) nickel (0.619 g, 2.20 mmol), 2,2'-bipyridine (0.24 g, 2.20 mmol), 1,5-cyclooctadiene (0.352 g, 2.20 mmol) and DMF (5 ml) in a reacting flask was reacted at 80° C. for half an hour, then a solution (5 ml) of 9,9'-di(4-octyloxy)phenyl-2,7-dibromofluorene (0.5088 g, 0.695 mmol), 9,9-di(10'-(p-(5"-phenyl-1",3",4"-oxdiazole-2"-)phenyloxy)decyloxy)-2,7-dibromofluorene (0.3228 g, 0.30 mmol) and 4-N,N-di(4-bromophenyl)-9-(4-t-butylphenyl)-1,8-naphthalimide (0.0033 g, 0.0050 mmol) in toluene was added. Reacted at 85° C. for 4 days. The rest steps were the same as those in Example 37. 0.31 g (yield 46%) of an orange yellow solid was obtained. $^1$H NMR (CDCl3, 300 MHz): δ 8.10-7.42 (m, Ar—H), 6.98 (b, Ar—H), 4.20-3.75 (b, $OCH_2$), 2.61-1.14 (m, $CH_2$), 1.03-0.80 (m, $CH_3$). Product performances: number average molecular weight (Mn), 22,000; maximum UV-absorption (film), 382 nm; solid fluorescence emissions, 421, 447 and 558 nm.

The assembling conditions of said single-layer electroluminescent device were the same as those of Example 37. The performances of said single-layer electroluminescent device were as follows: starting voltage, 5.8V; maximum luminance, 9330 $cd/m^2$; maximum efficiency of electroluminescence, 1.8 cd/A; color coordinate for a white light, (0.30, 0.46).

Example 43

Synthesizing and Characterizing of Polymeric Electroluminescent Material P7

Under the protection of $N_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.545 g, 0.995 mmol) and 4-N,N-di(4-bromostyryl)-9-(4-t-butylphenyl)-1,8-naphthalimide (0.0043 g, 0.0050 mmol) in toluene was added. Reacted at 80° C. for 5 days. The rest steps were the same as those in Example 37. 0.25 g (yield 64%) of an orange yellow solid was obtained. $^1$H NMR (300 MHz, CDCl3): δ 7.85-7.66(m, Ar—H), 2.15-1.11 (m, $CH_2$), 0.83-0.78(m, $CH_3$). Product performances: number average molecular weight (Mn), 22,000; maximum UV-absorption (film), 382 nm; solid fluorescence emissions, 435, 451 and 551 nm.

The assembling conditions of the single-layer electroluminescent device were the same as those of Example 37. The performances of said single-layer electroluminescent device were as follows: starting voltage, 4.8V; maximum luminance, 12400 $cd/m^2$; maximum efficiency of electroluminescence, 2.7 cd/A; color coordinate for a white light, (0.29, 0.33).

Example 44

Synthesizing and Characterizing of Polymeric Electroluminescent Material P8

Under the protection of $N_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.493 g, 0.899 mmol), N,N'-di(4-methyl-phenyl)-N,N'-di(4-bromophenyl)-1,4-phenylenediamine (0.0672 g, 0.10 mmol) and 4-N,N-(4,4'-di-(4-p-tolyl-4-bromophenylamino)-9-(4-t-butylphenyl)-1,8-naphthalimide (0.0058 g, 0.0001 mmol) in toluene was added. Reacted at 80° C. for 3 days. The rest steps were the same as those in Example 37. 0.30 g (yield 75%) of an orange yellow solid was obtained. $^1$H NMR (300 MHz, CDCl3): δ 7.81-7.56 (m, Ar—H), 7.23-7.14 (m, Ar—H), 2.36 (b, $CH_3$), 2.03 (b, $CH_2$), 1.19-1.06 (m, $CH_2$), 0.88-0.79(m, $CH_3$). Product performances: number average molecular weight (Mn), 35,000; maximum UV-absorption (film), 382 nm; solid fluorescence emissions, 428, 450 and 552 nm.

The assembling conditions of said single-layer electroluminescent device were the same as those of Example 37. The performances of said single-layer electroluminescent device were as follows: starting voltage, 5.4V; maximum luminance, 8880 cd/m$^2$; maximum efficiency of electroluminescence, 1.8 cd/A; color coordinate for white light, (0.25, 0.34).

Example 45

Synthesizing and Characterizing of Polymeric Electroluminescent Material P9

Under the protection of N$_2$ gas, 2,7-dibromo-9,9-dioctylfluorene (0.2713 g, 0.495 mmol), 9,9-dioctylfluorene-2,7-bis(trimethyleneborate) (0.2792 g, 0.50 mmol), 4-N,N-(4,4'-di-(4-p-tolyl-4-bromophenyl-amino)phenyl)-9-(4-t-butylphenyl)-1,8-naphthalimide (0.00012 g, 0.0001 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. The reaction system reacted at 100° C. for 24 hr. The reaction mixture was poured into methanol to obtain a black solid and filtered. The black solid was dissolved by chloroform, washed repeatedly with water, dried by anhydrous Na$_2$SO$_4$, concentrated, precipitated in methanol for three times, and extracted with acetone for 24 hr. 0.26 g (yield 65%) of a light yellow solid was obtained. $^1$H NMR (300 MHz, CDCl3): δ 7.86-7.68(m, Ar—H), 2.18-1.15 (m, CH$_2$), 0.85-0.79(m, CH$_3$). Product performances: Mn, 30,600; maximum UV-absorption (solid), 382 nm; solid fluorescence emissions, 424,442 and 550 nm.

The assembling conditions of the single-layer device were the same as those in Example 37. The performances of said single-layer electroluminescent device were as follows: starting voltage, 5.2V; maximum luminance, 7950 cd/m$^2$; maximum efficiency of electroluminescence, 2.0 cd/A; color coordinate, (0.24, 0.31).

Example 46

Synthesizing and Characterizing of Polymeric Electroluminescent Material P10

Under the protection of N$_2$ gas, 2,7-dibromo-9,9-dioctylfluorene (0.1096 g, 0.195 mmol), 9,9-dioctylfluorene-2,7-bis(trimethyleneborate) (0.2792 g, 0.50 mmol), N,N'-di(4-methylphenyl)-N,N'-di(4-bromophenyl)-1,4-phenylenediamine (0.2016 g, 0.30 mmol) and 4-N,N-(4,4'-di-(4-p-tolyl-4-bromophenyl-amino)phenyl)-9-(4-t-butylphenyl)-1,8-naphthalimide (0.0058 g, 0.0050 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. The reaction system reacted at 50° C. for 120 hr. The other conditions and steps were the same as those in Example 45. 0.26 g (yield 65%) of a light yellow solid was obtained. $^1$H NMR (300 MHz, CDCl3): δ 7.83-7.59 (m, Ar—H), 7.24-7.11 (m, Ar—H), 2.35 (b, CH$_3$), 2.01 (b, CH$_2$), 1.18-1.02 (m, CH$_2$), 0.86-0.79(m, CH$_3$). Product performances: Mn, 30,600; maximum UV-absorption (solid), 382 nm; solid fluorescence emissions, 424, 442 and 561 nm.

The assembling conditions of the single-layer electroluminescent device were the same as those in Example 37. The performances of said single-layer electroluminescent device were as follows: starting voltage, 5.2V; maximum luminance, 7950 cd/m$^2$; maximum efficiency of electroluminescence, 2.0 cd/A; color coordinate, (0.34, 0.39).

Example 47

Synthesizing and Characterizing of Polymeric Electroluminescent Material P11

Under the protection of N$_2$ gas, 2,7-dibromo-9,9-dioctylfluorene (0.2166 g, 0.40 mmol), 9,9-dioctylfluorene-2,7-bis(trimethyleneborate) (0.2792 g, 0.50 mmol), and 4-N,N-(4,4'-di-(4-p-tolyl-4-bromophenyl-amino)phenyl)-9-(4-t-butylphenyl)-1,8-naphthalimide (0.116 g, 0.10 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. The reaction system reacted at 85° C. for 48 hr. The other conditions and steps were the same as those in Example 45. 0.26 g (yield 65%) of a light yellow solid was obtained. $^1$H NMR (300 MHz, CDCl3): δ 8.60-8.31 (m, Ar—H), 7.85-7.43 (m, Ar—H), 7.27-7.02 (m, Ar—H), 2.88-2.69 (b, CH$_3$), 2.17-1.13 (m, CH$_2$ and CH$_3$), 0.84-0.79 (b, CH$_3$). Product performances: Mn, 30,600; maximum UV-absorption (solid), 382 nm; solid fluorescence emissions, 581 nm.

The assembling conditions of the single-layer electroluminescent device were the same as those in Example 37. The performances of said single-layer electroluminescent device were as follows: starting voltage, 5.2V; maximum luminance, 1950 cd/m$^2$; maximum efficiency of electroluminescence, 1.0 cd/A; color coordinate, (0.60, 0.36).

Example 48

Synthesizing and Characterizing of Polymeric Electroluminescent Material P12

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.548 g, 0.9995 mmol) and 4-N,N-(4,4'-di(4-p-tolyl-4-bromophenyl-amino)carbazolyl)-9-(4-t-butylphenyl)-1,8-naphthalimide (0.0006 g, 0.0005 mmol) in toluene was added. The reaction system reacted at 85° C. for 5 days. The other conditions and steps were the same as Example 37. 0.22 g (yield 57%) of a yellow solid was obtained. $^1$H NMR (300 MHz, CDCl3): δ 7.88-7.68(m, Ar—H), 2.17-1.14(m, CH$_2$), 0.84-0.78(m, CH$_3$). Product performances: Mn, 21,200; maximum UV-absorption (solid), 385 nm; solid fluorescence emissions, 428, 442 and 525 nm.

The assembling conditions of the single-layer device were the same as Example 37. The performances of said single-layer electroluminescent device were as follows: starting voltage, 5.0V; maximum luminance, 6550 cd/m$^2$; maximum efficiency of electroluminescence, 2.1 cd/A; color coordinate for white light, (0.35, 0.40).

Example 49

Synthesizing and Characterizing of Polymeric Electroluminescent Material P13

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol)

and DMF (5 ml) in a reacting flask was reacted at 80° C. for half an hour, then a toluene solution (5 ml) of 9,9'-dioctyl-2,7-dibromofluorene (0.545 g, 0.995 mmol), and 9-phenyl-9-((4-N-(4-(4'-styryl)phenyl)-4-N-phenyl-9-(4-t-butylphenyl)-1,8-naphthalimido)-2,7-dibromofluorene (0.0050 g, 0.0049 mmol) was added. The reaction system reacted at 80° C. for 5 days. The other conditions and steps were the same as Example 37. 0.24 g (yield 62%) of a yellow solid was obtained. $^1$H NMR (300 MHz, CDCl3): δ 7.86-7.69(m, Ar—H), 2.18-1.15(m, $CH_2$), 0.84-0.79(m, $CH_3$). Product performances: Mn, 27,000; maximum UV-absorption (solid), 385 nm; solid fluorescence emissions, 428, 442 and 532 nm.

The assembling conditions of the single-layer device were the same as Example 37. The performances of said single-layer electroluminescent device were as follows: starting voltage, 5.8V; maximum luminance, 9050 cd/m$^2$; maximum efficiency of electroluminescence, 2.8 cd/A; color coordinate for white light, (0.27, 0.32).

Example 50

Synthesizing and Characterizing of Polymeric Electroluminescent Material P14

Under the protection of $N_2$ gas, 2,7-dibromo-9,9-dioctylfluorene (0.1070 g, 0.195 mmol), 9,9-dioctylfluorene-2,7-bis(trimethyleneborate) (0.2792 g, 0.50 mmol), N,N'-di(4-methylphenyl)-N,N'-di(4-bromophenyl)-1,4-phenylenediamine (0.2016 g, 0.30 mmol), 9-phenyl-9-((4-N-(4-(4'-styryl)phenyl)-4-N-phenyl-9-(4-t-butylphenyl)-1,8-naphthalimido)-2,7-dibromofluorene (0.0050 g, 0.0050 mmol), anhydrous potassium carbonate (0.4140 g, 3 mmol) and tetrakis(triphenylphosphine) palladium (0) (0.0060 g, 0.0005 mmol) were added into a reacting flask, then toluene (5 ml) and water (2.0 ml) were added. The reaction system reacted at 80° C. for 96 hr. The other conditions and steps were the same as Example 45. 0.25 g (yield 65%) of a light yellow solid was obtained. $^1$H NMR (300 MHz, CDCl3): δ 7.81-7.55 (m, Ar—H), 7.25-7.14 (m, Ar—H), 2.36 (b, $CH_3$), 2.02 (b, $CH_2$), 1.17-1.05 (m, $CH_2$), 0.86-0.78(m, $CH_3$). Product performances: Mn, 25,600; maximum UV-absorption (solid), 382 nm; solid fluorescence emissions, 424, 442 and 531 nm.

The assembling conditions of the single-layer electroluminescent device were the same as Example 37. The performances of said single-layer electroluminescent device were as follows: starting voltage, 5.6V; maximum luminance, 9970 cd/m$^2$; maximum efficiency of electroluminescence, 1.7 cd/A; color coordinate, (0.26, 0.33).

Example 51

Synthesizing and Characterizing of Polymeric Electroluminescent Material P15

Under the protection of $N_2$ gas, 2,7-dibromo-9,9-dioctylfluorene (0.2739 g, 0.4999 mmol), 9,9-dioctylfluorene-2,7-bis(trimethyleneborate) (0.2792 g, 0.5 mmol), 2-(6'-(4'-N,N-diphenylamino-1',8'-naphthalimido-9'-alkyl)hexoxy)-5-hexoxy-1,4-dibromobenzene (0.00081 g, 0.0001 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (3 ml) were added. The reaction system reacted at 100° C. for 24 hr. The other conditions and steps were the same as Example 45. 0.21 g (yield 54%) of a light yellow solid was obtained. $^1$H NMR (300 MHz, CDCl3): δ 7.85-7.66(m, Ar—H), 2.16-1.15(m, $CH_2$), 0.84-0.79(m, $CH_3$). Product performances: Mn, 23,000; maximum UV-absorption (solid), 378 nm; solid fluorescence emissions, 435 and 510 nm.

The assembling conditions of the single-layer electroluminescent device were the same as Example 37. The performances of said single-layer electroluminescent device were as follows: starting voltage, 5.8V; maximum luminance, 13080 cd/m$^2$; maximum efficiency of electroluminescence, 6.6 cd/A; color coordinate, (0.13, 0.50).

Example 52

Synthesizing and Characterizing of Polymeric Electroluminescent Material P16

Under the protection of $N_2$ gas, a mixture of bis(1,5-cyclooctadienyl) nickel (0.56 g, 2.0 mmol), 2,2'-bipyridine (0.22 g, 2.0 mmol), 1,5-cyclooctadiene (0.32 g, 2.0 mmol) and DMF (5 ml) in a reacting flask was reacted at 80° C. for half an hour, then a toluene solution (5 ml) of 9,9'-dioctyl-2,7-dibromofluorene (0.3288 g, 0.60 mmol), 2-(6'-(4'-N,N-diphenylamino-1',8'-naphthalimide-9'-alkyl)hexoxy)-5-hexoxyl-1,4-dibromobenzene (0.88 g, 0.1 mmol) and N,N'-di(4-methyl-phenyl)-N,N'-di(4-bromophenyl)-1,4-phenylenediamine (0.20162 g, 0.30 mmol) was added. The reaction system reacted at 100° C. for 1 day. The other conditions and steps were the same as Example 37. 0.24 g (yield 60%) of a yellow solid was obtained. $^1$HNMR 8.60-8.52 (b, Ar—H), 8.28-8.18 (b, Ar—H), 7.85-7.55 (b, Ar—H), 7.20-6.85(b, Ar—H), 4.22-4.14 (b, —$OCH_2$), 2.30-1.15 (b, $CH_2$), 0.88-0.78 (b, $CH_3$). Product performances: Mn, 26,000; maximum UV-absorption (solid), 375 nm; solid fluorescence emissions, 519 nm.

The assembling conditions of the single-layer electroluminescent device were the same as Example 37. The performances of said single-layer electroluminescent device were as follows: starting voltage, 5.2V; maximum luminance, 8450 cd/m$^2$; maximum efficiency of electroluminescence, 1.2 cd/A; color coordinate for white light, (0.26, 0.68).

Example 53

Synthesizing and Characterizing of Polymeric Electroluminescent Material P17

Under the protection of $N_2$ gas, a mixture of bis(1,5-cyclooctadienyl) nickel (0.844 g, 3.0 mmol), 2,2'-bipyridine (0.33 g, 3.0 mmol), 1,5-cyclooctadiene (0.48 g, 3.0 mmol) and DMF (5 ml) in a reacting flask was reacted at 80° C. for half an hour, then a toluene solution (5 ml) of 9,9'-dioctyl-2,7-dibromofluorene (0.548 g, 0.9999 mmol), and 1,4-dibromo-2-hexoxyl-5-(6-(4-di(4'-dianilino-biphenyl-4-)amino-1,8-naphthalimide-9-)-hexoxyl)benzene (0.13 g, 0.0001 mmol) was added. The reaction system reacted at 50° C. for 5 day. The other conditions and steps were the same as Example 37. 0.24 g (yield 60%) of an orange solid was obtained. $^1$H NMR (300 MHz, CDCl3): δ 7.88-7.69(m, Ar—H), 2.18-1.15(m, $CH_2$), 0.85-0.79(m, $CH_3$). Product performances: Mn, 24,800; maximum UV-absorption (solid), 375 nm; solid fluorescence emissions, 435 and 551 nm.

The assembling conditions of the single-layer electroluminescent device were the same as Example 37. The performances of said single-layer electroluminescent device were as follows: starting voltage, 5.0V; maximum luminance, 15400 cd/m$^2$; maximum efficiency of electroluminescence, 4.2 cd/A; color coordinate for white light, (0.27, 0.34).

Example 54

Synthesizing and Characterizing of Polymeric Electroluminescent Material P18

Under the protection of $N_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a toluene solution (5 ml) of 9,9'-dioctyl-2,7-dibromofluorene (0.54534 g, 0.995 mmol), and 1,4-dibromo-2-hexoxyl-5-(6-(4-di(4-styrylphenyl-1-)amino-1,8-naphthalimide-9-)-hexoxyl)benzene (0.0050 g, 0.005 mmol) was added. The reaction system reacted at 80° C. for 3 days. The other conditions and steps were the same as Example 37. 0.24 g (yield 60%) of an orange solid was obtained. $^1$H NMR (300 MHz, CDCl3): δ 7.87-7.68(m, Ar—H), 2.17-1.15(m, $CH_2$), 0.83-0.77(m, $CH_3$). Product performances: Mn, 24,800; maximum UV-absorption (solid), 375 nm; solid fluorescence emissions, 440 and 552 nm.

The assembling conditions of the single-layer electroluminescent device were the same as Example 37. The performances of said single-layer electroluminescent device were as follows: starting voltage, 4.8V; maximum luminance, 12400 cd/m$^2$; maximum efficiency of electroluminescence, 2.2 cd/A; color coordinate for white light, (0.30, 0.34).

Example 55

Synthesizing and Characterizing of Polymeric Electroluminescent Material P19

Under the protection of $N_2$ gas, a mixture of bis(1,5-cyclooctadienyl) nickel (0.844 g, 3.0 mmol), 2,2'-bipyridine (0.33 g, 3.0 mmol), 1,5-cyclooctadiene (0.48 g, 3.0 mmol) and DMF (5 ml) in a reacting flask was reacted at 80° C. for half an hour, then a toluene solution (5 ml) of 9,9'-dioctyl-2,7-dibromofluorene (0.545 g, 0.995 mmol) was added. The reaction system reacted at 100° C. for 1 day. A solution (0.5 ml) of 4-N-(4-(4'-bromostyryl)phenyl)-4-N-phenyl-9-(4-t-butylphenyl)-1,8-naphthalimide (0.0034 g, 0.0050 mmol) in toluene was then added. The reaction system reacted at 80° C. for further 1 hr. The other conditions and steps were the same as Example 37. 0.28 g (yield 72%) of a light yellow solid was obtained. $^1$H NMR (300 MHz, CDCl3): δ 7.86-7.68(m, Ar—H), 2.16-1.14(m, $CH_2$), 0.83-0.77(m, $CH_3$). Product performances: Mn, 19,600; maximum UV-absorption (solid), 383 nm; solid fluorescence emissions, 425, 447 and 528 nm.

The assembling conditions of the single-layer electroluminescent device were the same as Example 37. The performances of said single-layer electroluminescent device were as follows: starting voltage, 5.2V; maximum luminance, 16880 cd/m$^2$; maximum efficiency of electroluminescence, 2.6 cd/A; color coordinate for white light, (0.25, 0.38).

Example 56

Synthesizing and Characterizing of Polymeric Electroluminescent Material P20

Under the protection of $N_2$ gas, a mixture of bis(1,5-cyclooctadienyl) nickel (0.56 g, 2.0 mmol), 2,2'-bipyridine (0.22 g, 2.0 mmol), 1,5-cyclooctadiene (0.32 g, 2.0 mmol) and DMF (5 ml) in a reacting flask was reacted at 80 ° C. for half an hour. Then a solution (5 ml) of 9,9'-dioctyl-2,7-dibromofluorene (0.545 g, 0.995 mmol) in toluene was added. After reacting at 50° C. for 5 days, a solution (0.5 ml) of 4-N-(4-methylphenyl)-4-N-(4-bromophenyl)-9-(4-t-butylphenyl)-1,8-naphthalimide (0.0029 g, 0.0049 mmol) in toluene was added. The reaction system reacted at 50° C. for further 2 days. The other conditions and steps were the same as Example 37. 0.27 g (yield 70%) of a yellow solid was obtained. $^1$H NMR (300 MHz, CDCl3): δ 7.86-7.68(m, Ar—H), 2.17-1.15(m, $CH_2$), 0.85-0.79(m, $CH_3$). Product performances: Mn, 22,450; maximum UV-absorption (solid), 380 nm; solid fluorescence emissions, 430, 451 and 523 nm.

The assembling conditions of the single-layer electroluminescent device were the same as Example 37. The performances of said single-layer electroluminescent device were as follows: starting voltage, 6.8V; maximum luminance 19280 cd/m$^2$; maximum efficiency of electroluminescence, 7.4 cd/A; color coordinate, (0.34, 0.50).

Example 57

Synthesizing and Characterizing of Polymeric Electroluminescent Material P21

Under the protection of $N_2$ gas, 2,7-dibromo-9,9-dioctylfluorene (0.2714 g, 0.495 mmol), 9,9-dioctylfluorene-2,7-bis(trimethyleneborate) (0.2792 g, 0.5 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. After reacting at 100° C. for 24 hr, 4-N-(4-methylphenyl)-4-N-(4-bromophenyl)-9-(4-t-butylphenyl)-1,8-naphthalimide (0.0029 g, 0.005 mmol) was added. The reaction system reacted at 100° C. for further 1 hr. The other conditions and steps were the same as Example 45. 0.21 g (yield 54%) of a light yellow solid was obtained. $^1$H NMR (300 MHz, CDCl3): δ 7.84-7.65(m, Ar—H), 2.16-1.12(m, $CH_2$), 0.85-0.77(m, $CH_3$). Product performances: Mn, 20,300; maximum UV-absorption (solid), 387 nm; solid fluorescence emissions, 435, 443 and 525 nm.

The assembling conditions of the single-layer device were the same as Example 37. The performances of said single-layer electroluminescent device were as follows: starting voltage, 6.4V; maximum luminance, 17780 cd/m$^2$; maximum efficiency of electroluminescence, 7.2 cd/A; color coordinate, (0.34, 0.52).

Example 58

Synthesizing and Characterizing of Polymeric Electroluminescent Material P22

Under the protection of $N_2$ gas, 2,7-dibromo-9,9-dioctylfluorene (0.1096 g, 0.1999 mmol), 9,9-dioctylfluorene-2,7-bis(trimethyleneborate) (0.2792 g, 0.5 mmol), N,N'-di(4-methyl-phenyl)-N,N'-di(4-bromophenyl)-1,4-phenylenediamine (0.2016 g, 0.30 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. After reacting at 50° C. for 120 hr, 4-N-(4-methylphenyl)-4-N-(4-bromophenyl)-9-(4-t-butylphenyl)-1,8-naphthalimide (0.00058 g, 0.0001 mmol) was added. The reaction system reacted at 50° C. for further 48 hr. The other conditions and steps were the same as Example 45. 0.26 g (yield 59%) of a light yellow solid was obtained. $^1$H NMR (CDCl$_3$, 300 MHz): δ 7.81-7.56 (m, Ar—H), 7.23-7.10 (m, Ar—H), 2.34 (b, $CH_3$), 2.00(b, $CH_2$), 1.19-1.06 (m, $CH_2$), 0.86-0.77 (m, $CH_3$). Product performances: Mn, 23,400;

maximum UV-absorption (solid), 385 nm; solid fluorescence emissions, 435, 443 and 520 nm.

The assembling conditions of the single-layer device were the same as Example 37. The performances of said single-layer electroluminescent device were as follows: starting voltage, 5.2V; maximum luminance, 7980 cd/m$^2$; maximum efficiency of electroluminescence, 2.2 cd/A; color coordinate, (0.23, 0.28).

Example 59

Synthesizing and Characterizing of Polymeric Electroluminescent Material P23

Under the protection of N$_2$ gas, 2,7-dibromo-9,9-dioctylfluorene (0.2192 g, 0.40 mmol), 9,9-dioctylfluorene-2,7-bis(trimethyleneborate) (0.2792 g, 0.5 mmol), anhydrous potassium carbonate (0.4140 g, 3 mmol), and tetrakis(triphenylphosphine) palladium (0) (0.0060 g, 0.0005 mmol) were added into a reacting flask, then toluene (4 ml) and water (1.5 ml) were added. After reacting at 50° C. for 120 hr, 4-N-(4-methylphenyl)-4-N-(4-bromophenyl)-9-(4-t-butylphenyl)-1,8-naphthalimide (0.058 g, 0.10 mmol) was added. The reaction system reacted at 50° C. for further 48 hr. The other conditions and steps were the same as Example 45. 0.21 g (yield 53%) of a light yellow solid was obtained. $^1$H NMR (300 MHz, CDCl3): δ 8.62-8.33 (m, Ar—H), 7.85-7.43 (m, Ar—H), 7.24-7.02 (m, Ar—H), 2.85-2.75 (b, CH$_3$), 2.18-1.11 (m, CH$_2$ and CH$_3$), 0.85-0.78 (b, CH$_3$). Product performances: Mn, 7,400; maximum UV-absorption (solid), 380 nm; solid fluorescence emissions, 535 nm.

The assembling conditions of the single-layer device were the same as Example 37. The performances of said single-layer electroluminescent device were as follows: starting voltage, 5.4V; maximum luminance, 1770 cd/m$^2$; maximum efficiency of electroluminescence, 0.82 cd/A; color coordinate, (0.40, 0.58).

Example 60

Synthesizing and Characterizing of Polymeric Electroluminescent Material P24

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.3835 g, 0.6999 mmol) and N,N'-di(4-methylphenyl)-N,N'-di(4-bromophenyl)-1,4-phenylenediamine (0.2016 g, 0.30 mmol) in toluene was added. After reacting at 80° C. for 3 days, a solution (0.5 ml) of 4-N-(4-methylphenyl)-4-N-(4-bromophenyl)-9-(4-t-butylphenyl)-1,8-naphthalimide (0.00058 g, 0.0001 mmol) in toluene was added. Reacted at 80° C. for 1 day. The other steps and conditions are the same as those in Example 37. 0.27 g (yield 47%) of a yellow solid was obtained. $^1$H NMR (CDCl$_3$, 300 MHz): δ 7.82-7.58 (m, Ar—H), 7.24-7.12 (m, Ar—H), 2.37 (b, CH$_3$), 2.02 (b, CH$_2$), 1.18-1.05 (m, CH$_2$), 0.85-0.79 (m, CH$_3$). Product performances: number average molecular weight (Mn), 26,700; maximum UV-absorption (solid), 380 nm; solid fluorescence emissions, 430, 441 and 525 nm.

The assembling conditions of the single-layer electroluminescent device were the same as Example 37. The performances of said single-layer electroluminescent device were as follows: starting voltage, 6.0V; maximum luminance, 4350 cd/m$^2$; maximum efficiency of electroluminescence, 1.8 cd/A; color coordinate, (0.23, 0.21).

Example 61

Synthesizing and Characterizing of Polymeric Electroluminescent Material P25

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.5453 g, 0.995 mmol) in toluene was added. After reacting at 80° C. for 3 days, a solution (0.5 ml) of 4-N-(4-methylphenyl)-4-N-(4-methylphenyl-4'-bromophenylamino)phenyl-9-(4-t-butylphenyl)-1,8-naphthalimide (0.0042 g, 0.005 mmol) in toluene was added. Reacted at 80° C. for 1 day. The other steps and conditions are the same as those in Example 37. 0.25 g (yield 64%) of a yellow solid was obtained. $^1$H NMR (300 MHz, CDCl3): δ 7.87-7.70 (m, Ar—H), 2.19-1.15(m, CH$_2$), 0.84-0.79(m, CH$_3$). Product performances: number average molecular weight (Mn), 20,700; maximum UV-absorption (solid), 381 nm; solid fluorescence emissions, 433 and 545 nm.

The assembling conditions of the single-layer electroluminescent device were the same as Example 37. The performances of said single-layer electroluminescent device were as follows: starting voltage, 6.0V; maximum luminance, 10950 cd/m$^2$; maximum efficiency of electroluminescence, 4.3 cd/A; color coordinate, (0.28, 0.32).

Example 62

Synthesizing and Characterizing of Polymeric Electroluminescent Material P26

Under the protection of N$_2$ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.4932 g, 0.90 mmol) in toluene was added. After reacting at 80° C. for 3 days, a solution (0.5 ml) of 4-N-(4-methylphenyl)-4-N-(4-methylphenyl-4'-bromophenylamino)phenyl-9-(4-t-butylphenyl)-1,8-naphthalimide (0.084 g, 0.1 mmol) in toluene was added. Reacted at 80° C. for 1 day. The other steps and conditions are the same as those in Example 37. 0.26 g (yield 60%) of a yellow solid was obtained. $^1$H NMR (300 MHz, CDCl3): δ 8.61-8.32 (m, Ar—H), 7.82-7.41 (m, Ar—H), 7.28-7.00 (m, Ar—H), 2.86-2.68 (m, CH$_3$), 2.16-1.11 (m, CH$_2$ and CH$_3$), 0.84-0.78 (b, CH$_3$). Product performances: number average molecular weight (Mn), 6,700; maximum UV-absorption (solid), 381 nm; solid fluorescence emissions, 553 nm.

The assembling conditions of the single-layer electroluminescent device were the same as Example 37. The performances of said single-layer electroluminescent device were as follows: starting voltage, 5.4V; maximum luminance, 2950 cd/m²; maximum efficiency of electroluminescence, 1.3 cd/A; color coordinate, (0.43, 0.56).

Example 63

Synthesizing and Characterizing of Polymeric Electroluminescent Material P27

Under the protection of N₂ gas, a mixture of bis(1,5-cyclooctadienyl) nickel (0.619 g, 2.20 mmol), 2,2'-bipyridine (0.24 g, 2.2 mmol), 1,5-cyclooctadiene (0.352 g, 2.20 mmol) and DMF (5 ml) in a reacting flask was reacted at 80° C. for half an hour, then a solution (5 ml) of 9,9'-dioctyl-2,7-dibromofluorene (0.5453 g, 0.995 mmol) in toluene was added. After reacting at 80° C. for 3 days, a solution (0.5 ml) of 4-N-p-bromophenyl-4-N-(4-styryl)phenyl-9-(4-t-butylphenyl)-1,8-naphthalimide (0.0034 g, 0.005 mmol) in toluene was added. Reacted at 80° C. for 1 day. The other steps and conditions are the same as those in Example 37. 0.22 g (yield 57%) of a yellow solid was obtained. ¹H NMR (300 MHz, CDCl3): δ 7.88-7.68(m, Ar—H), 2.17-1.15(m, CH₂), 0.86-0.80(m, CH₃). Product performances: number average molecular weight (Mn), 19,200; maximum UV-absorption (solid), 376 nm; solid fluorescence emissions, 433 and 540 nm.

The assembling conditions of the single-layer electroluminescent device were the same as Example 37. The performances of said single-layer electroluminescent device were as follows: starting voltage, 5.0V; maximum luminance, 9940 cd/m²; maximum efficiency of electroluminescence, 3.3 cd/A; color coordinate for white light, (0.27, 0.33).

What is claimed is:

1. A white electroluminescent polymeric material, comprising a single white electroluminescent polymeric material selected from a group consisting of:

type (I): main chain type single white electroluminescent polymeric material,

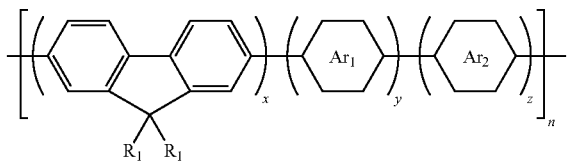

wherein: R₁ is alkyl or aryl, Ar1 is a naphthalimide derivative basic unit having one or more structures as listed below:

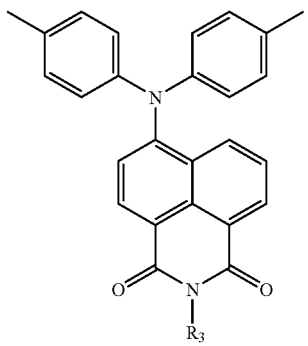

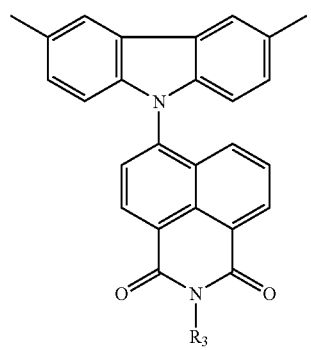

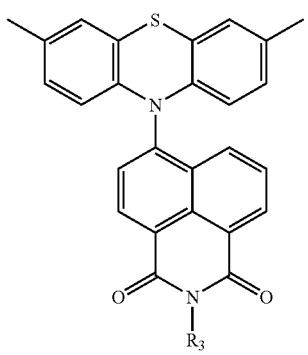

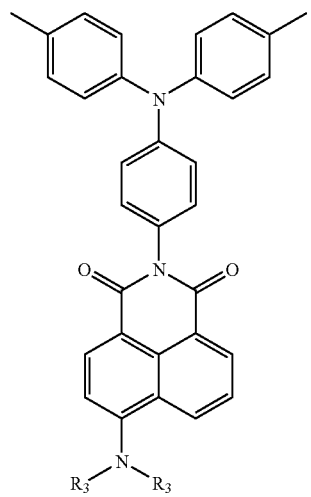

-continued
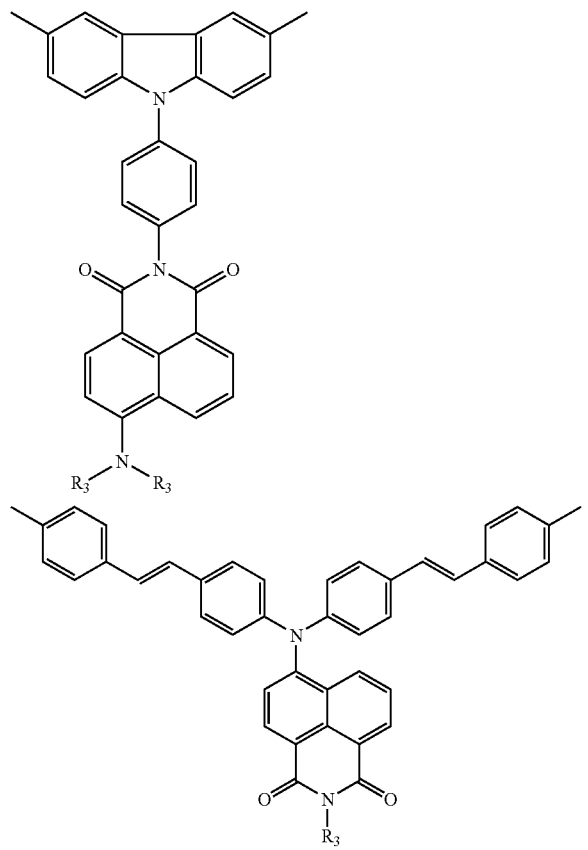
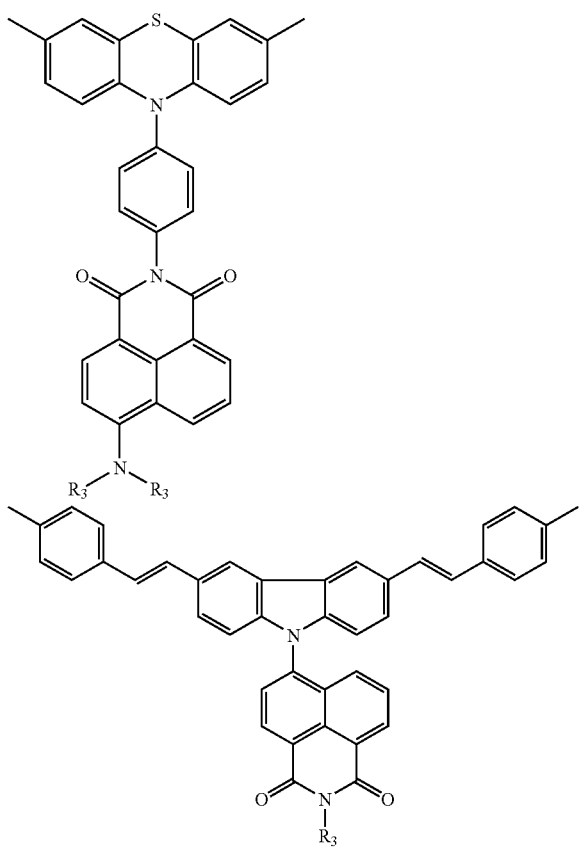
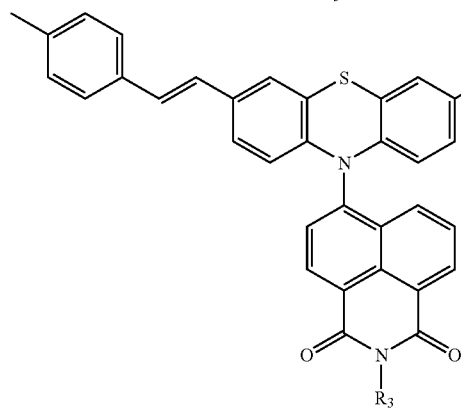
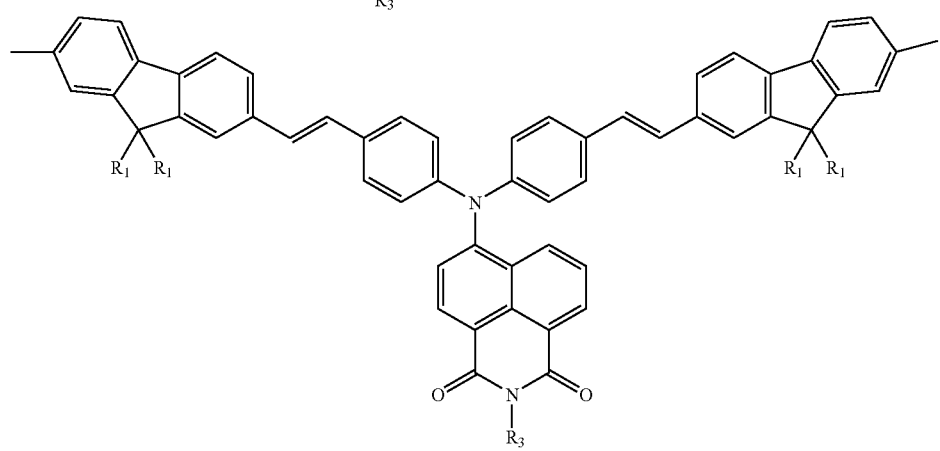

-continued
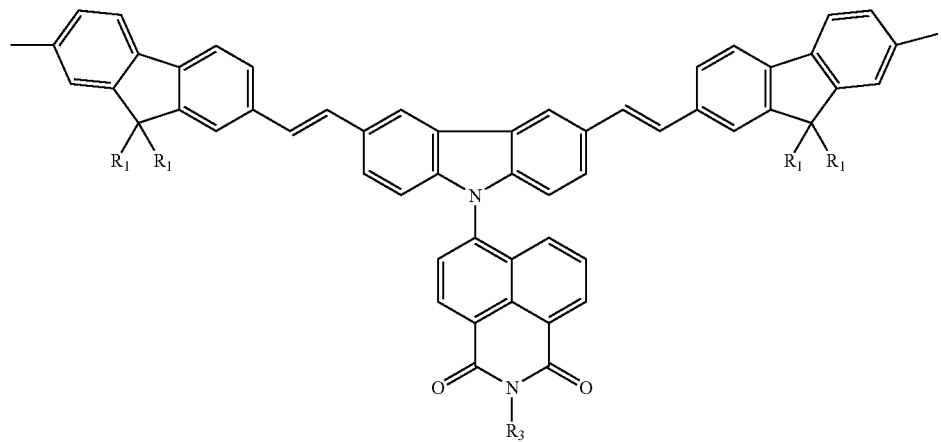
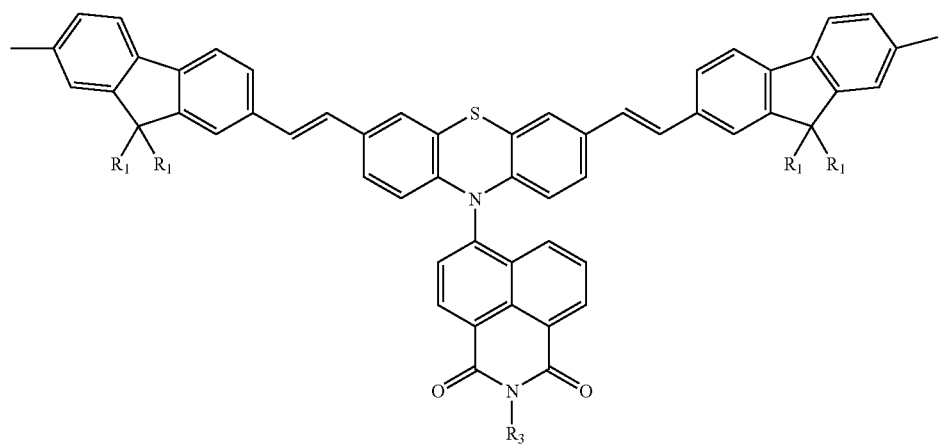
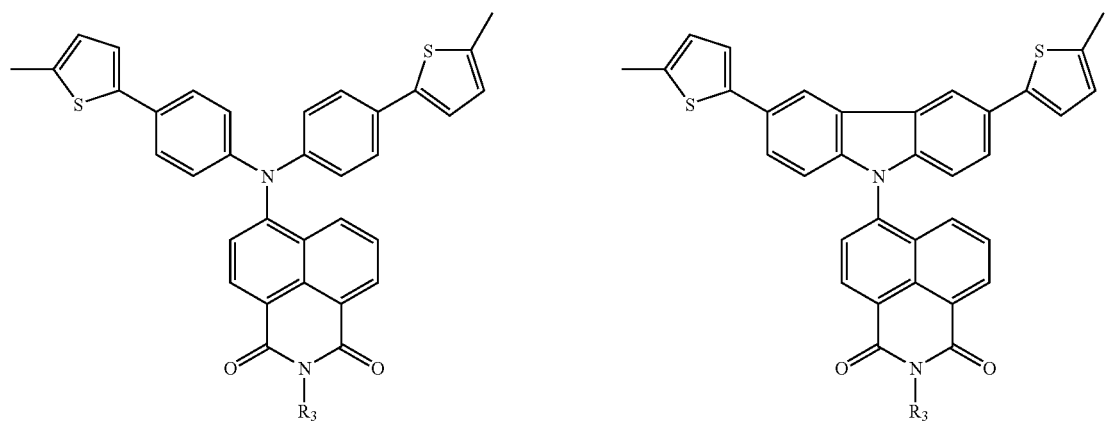

-continued
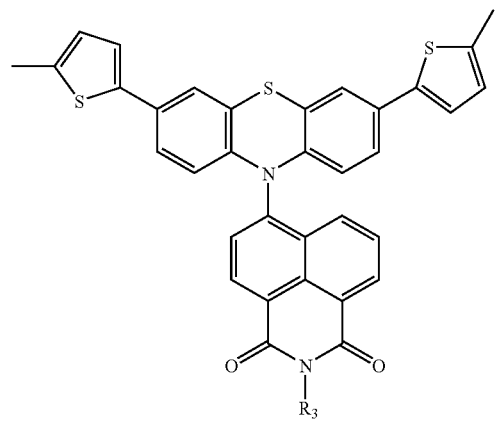
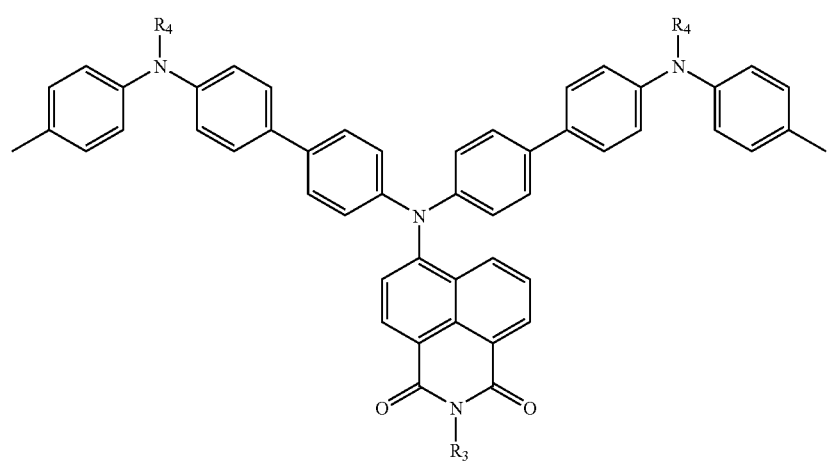
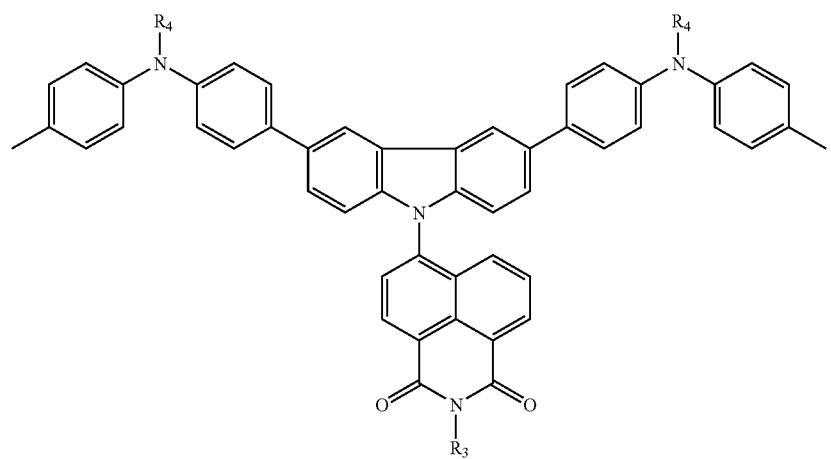

-continued
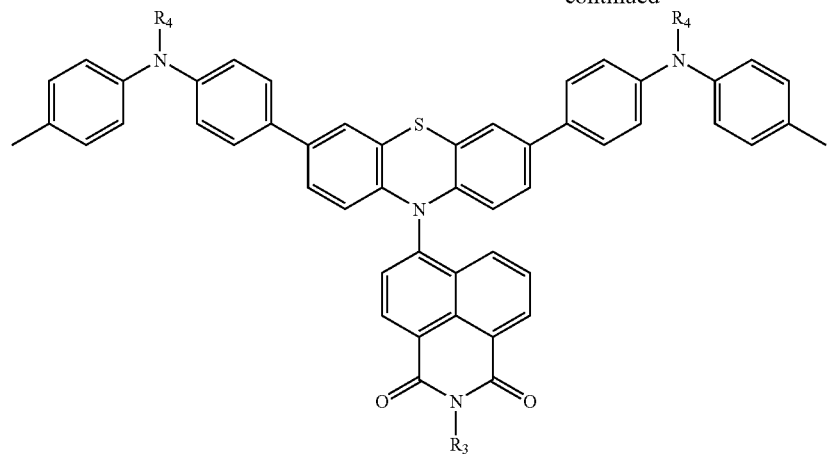
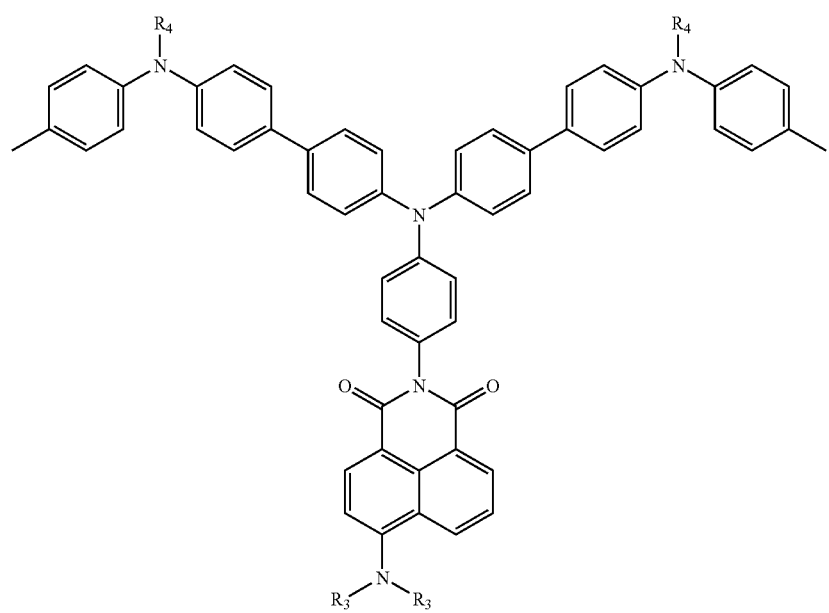
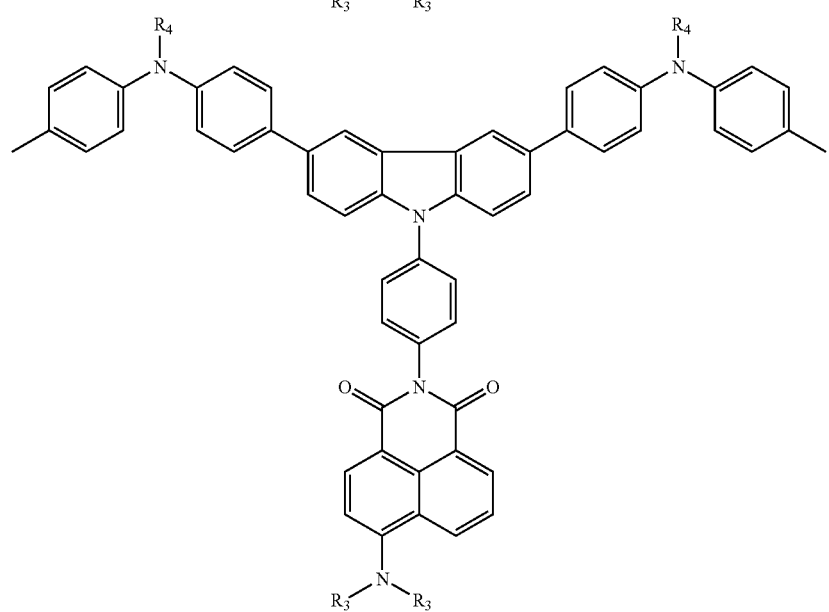

-continued
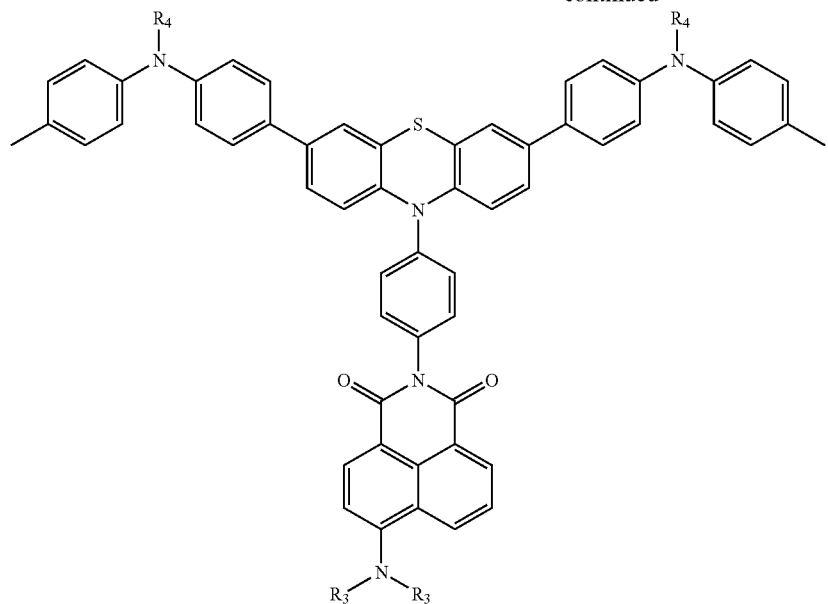
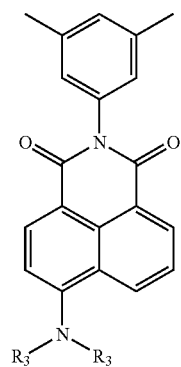
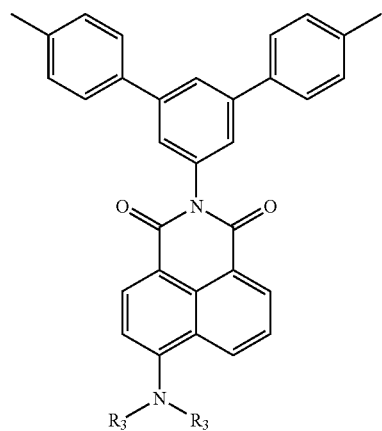
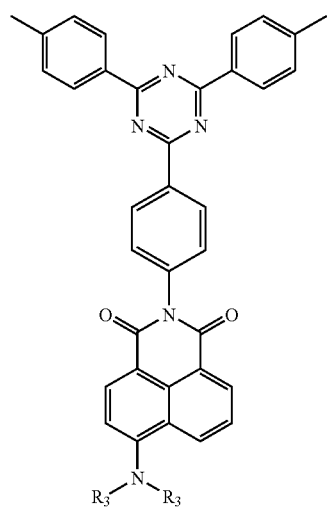
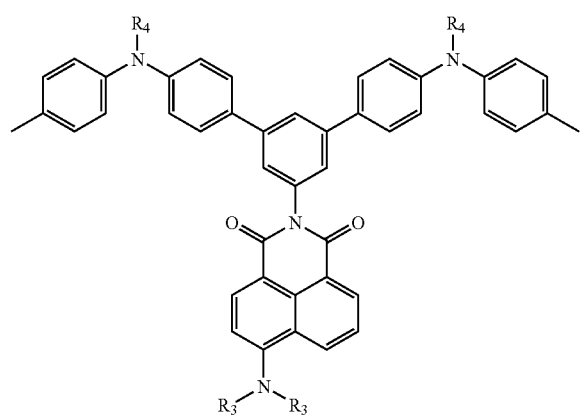

-continued
77
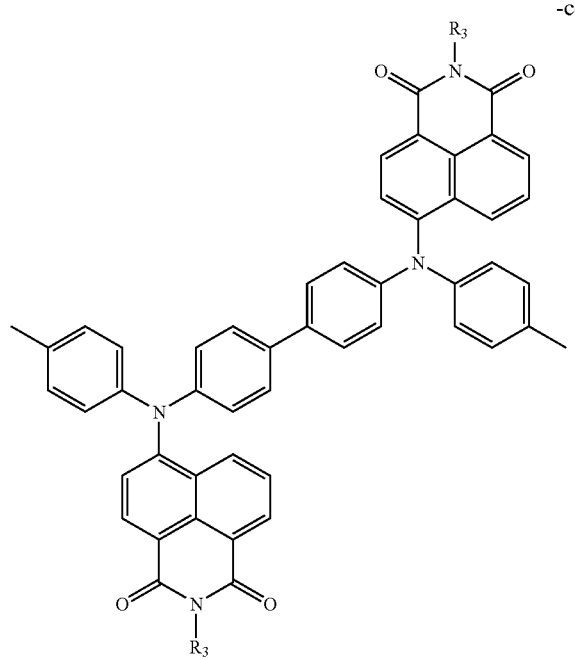
78
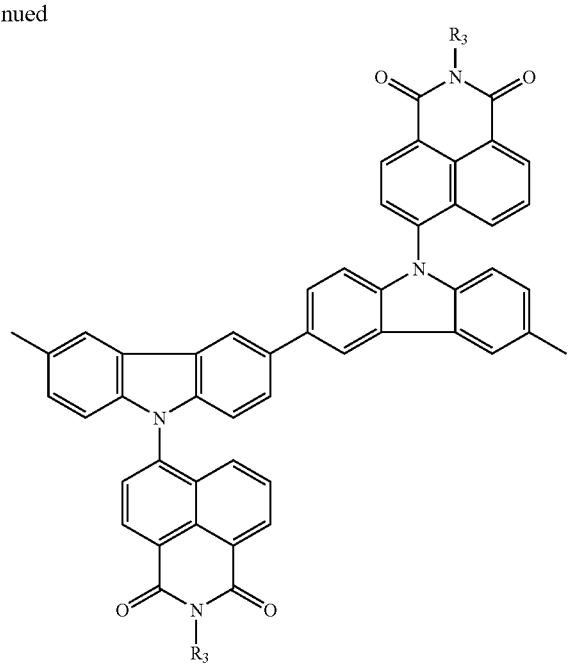
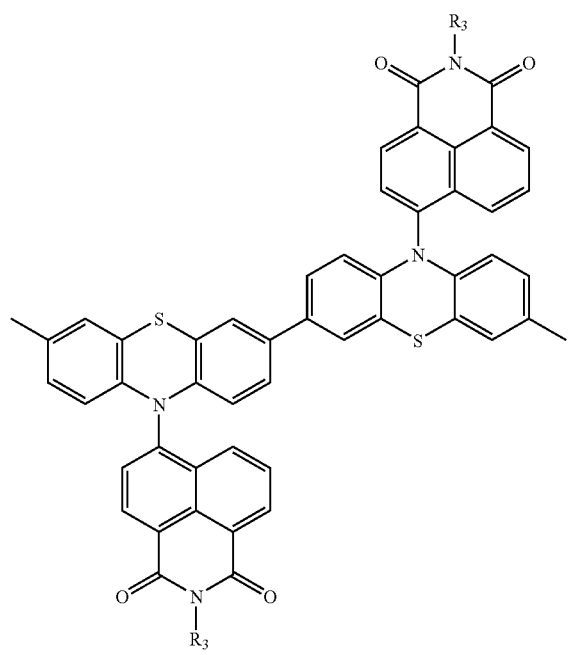

wherein, Ar2 is an electron transport basic unit, a hole transport basic unit or a luminescence basic unit; x, y, and z each represents the content of one basic unit, satisfying $0.6500<x<0.9999$, $0.0001 \leq v \leq 0.0050$, $0.0000<z<0.3000$, $x+y+z=1$, and $n=1$-300, wherein, the chain lengths of the alkyl and the alkoxy are 1-18; the aryl is selected from a group consisting of phenyl, naphthyl, fluorenyl, triphenylamino, oxadizolyl, and phenyl or naphthyl substituted by alkyl or alkoxy; $R_3$ and $R_4$ independently represent an alkyl having a chain length of 1-18 or an aryl, wherein the aryl is selected from a group consisting of phenyl, naphthyl, and phenyl or naphthyl substituted by alkyl or alkoxy;

Ar2 has one or more structural units selected from the following units:

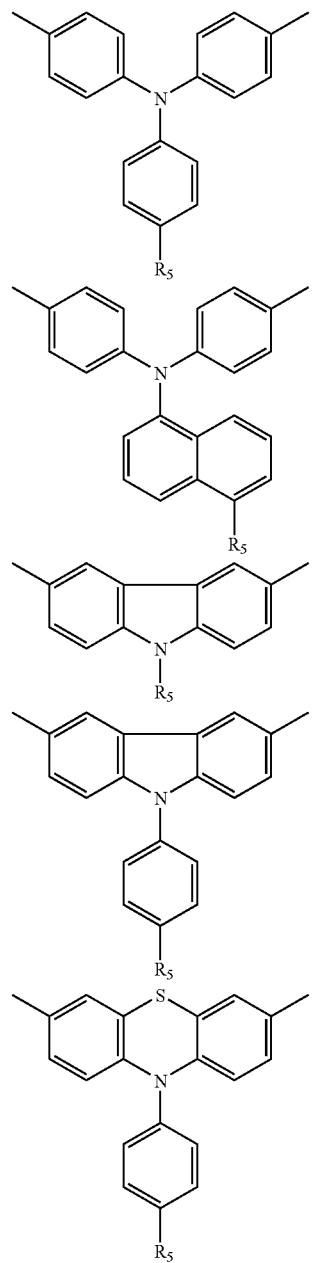

-continued

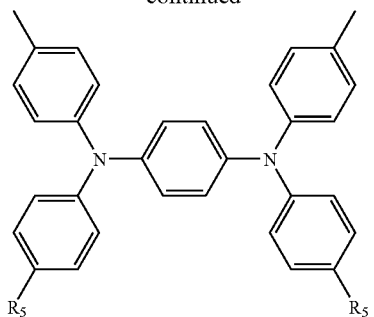

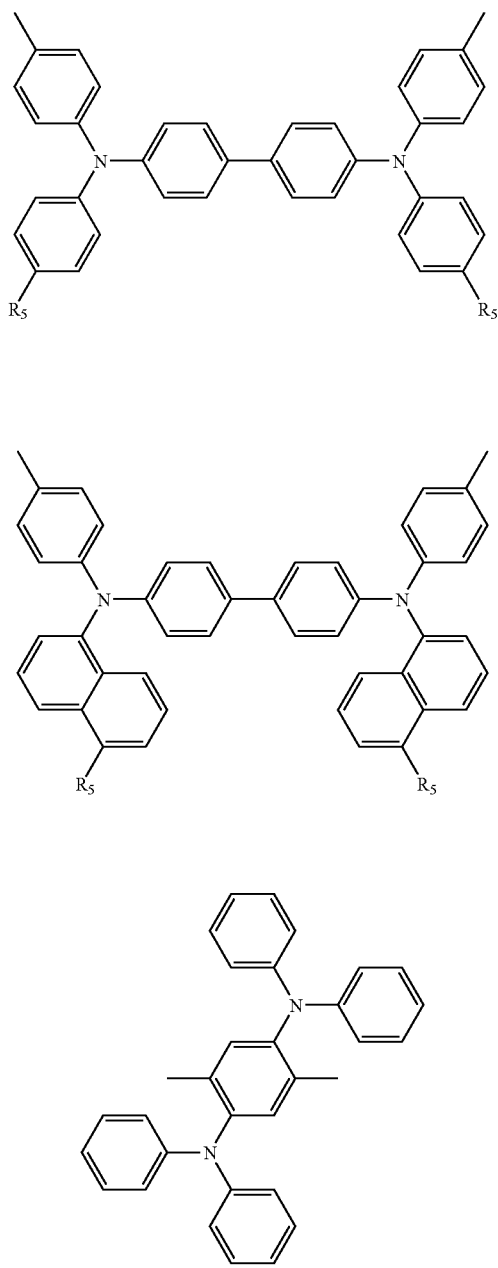

-continued
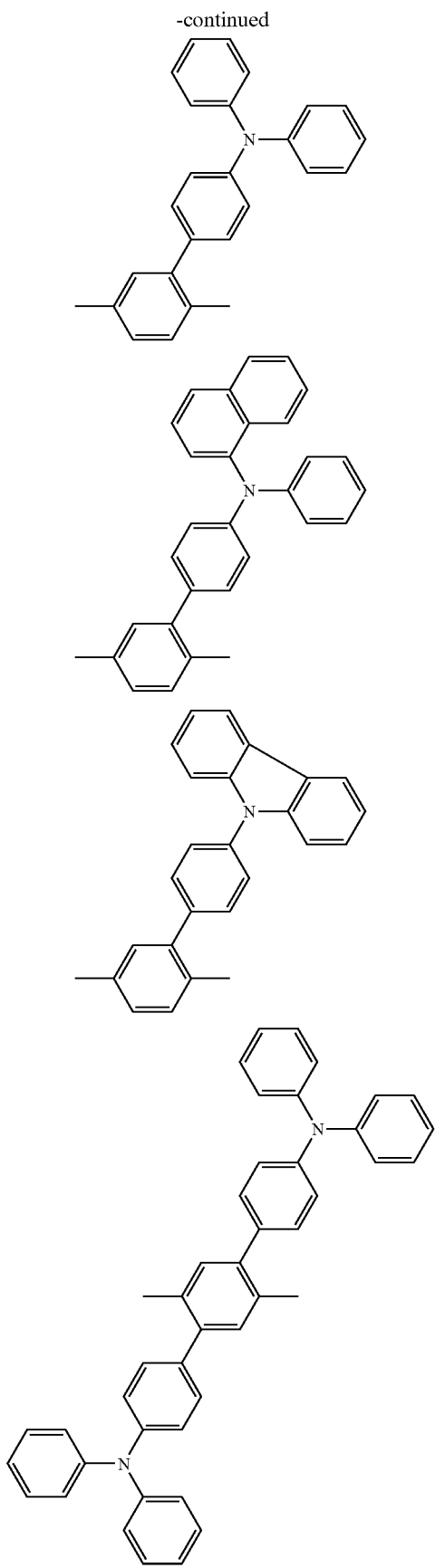
-continued
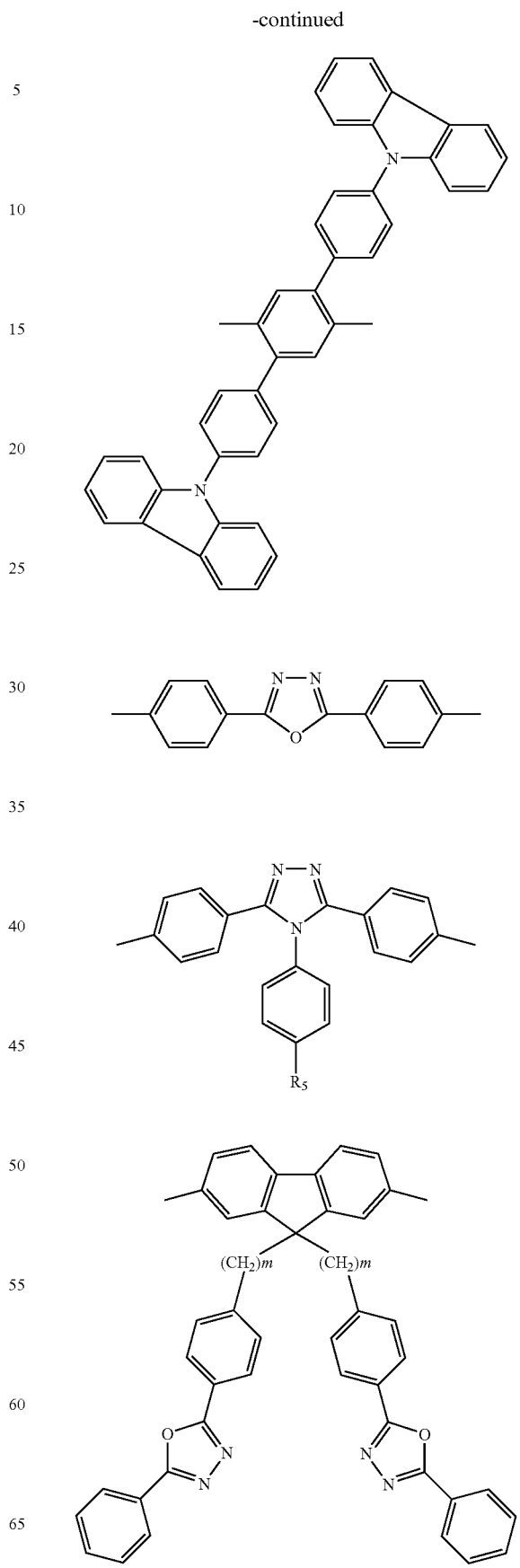

wherein $R_5$ is selected from a group consisting of alkyl, phenyl, naphthyl, and phenyl or naphthyl substituted by alkyl or alkoxy, m=0-20; wherein, the chain lengths of the alkyl and the alkoxy are 1-18;

type (II): pendant chain type single white electroluminescent polymeric material

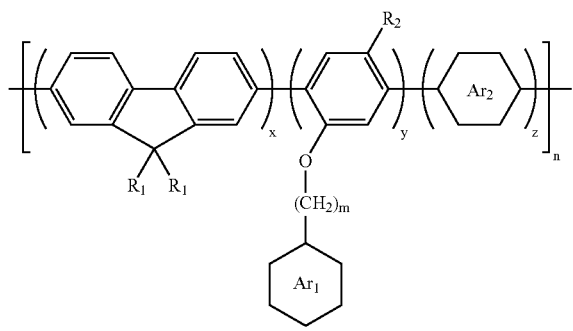

-continued

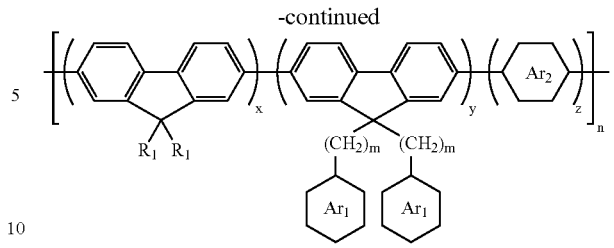

wherein: $R_2$ is selected from a group consisting of alkyl, alkoxy, phenyl, and phenyl substituted by alkyl or alkoxy; Ar1 is a naphthalimide derivative basic unit; the basic structure of Ar2 is the same as the Ar2 of the main chain type single white luminescent polymeric material; each basic unit content—x, y and z satisfy $0<x\leqq1$, $0<y<1$, $0\leqq z<1$, x+y+z=1, m=0-20, n=1-300; wherein the chain lengths of the alkyl and the alkoxy are 1-18;

Ar1 has one or more structures as listed below:

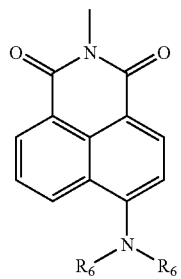

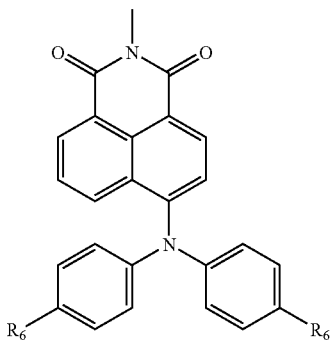

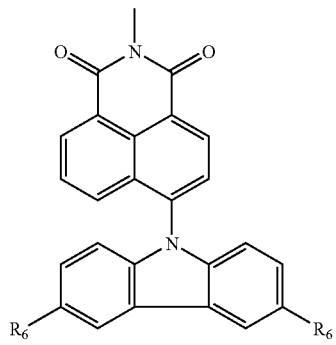

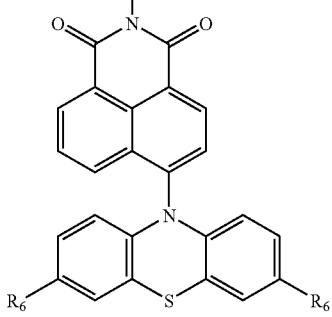

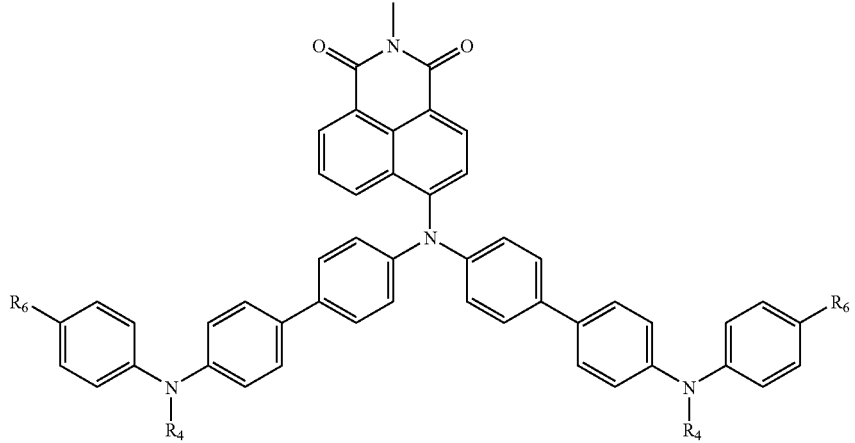

-continued
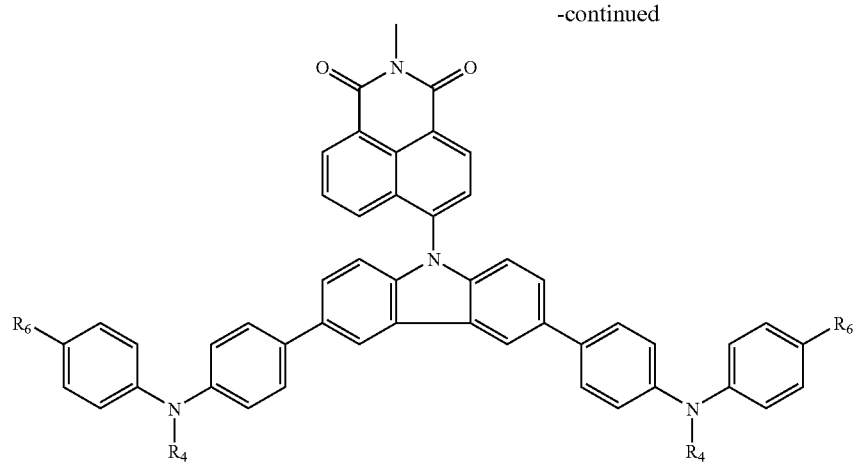
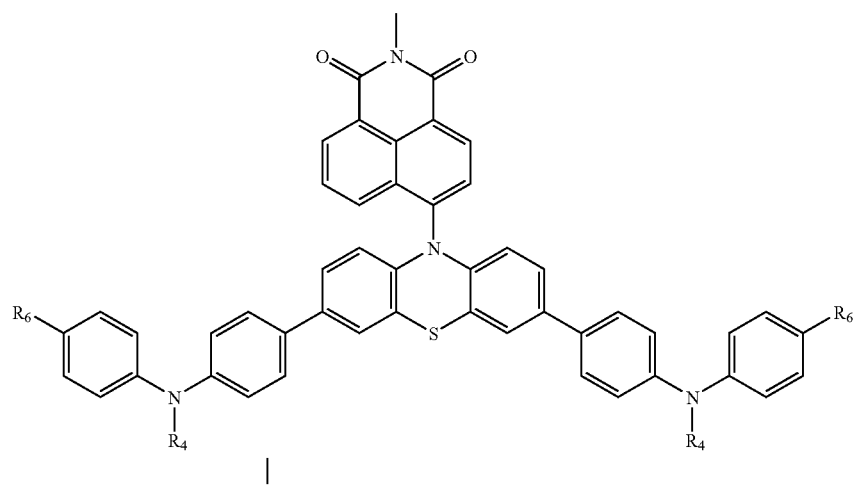
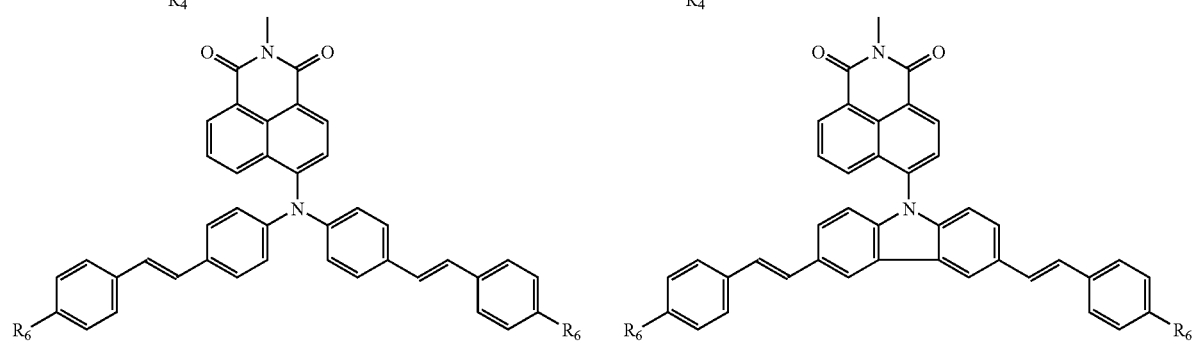
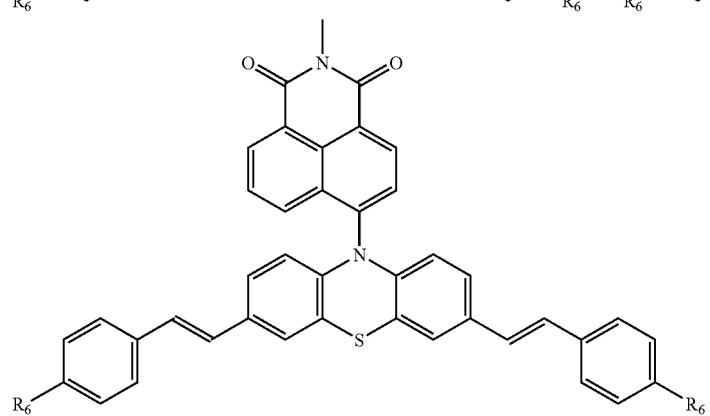

-continued
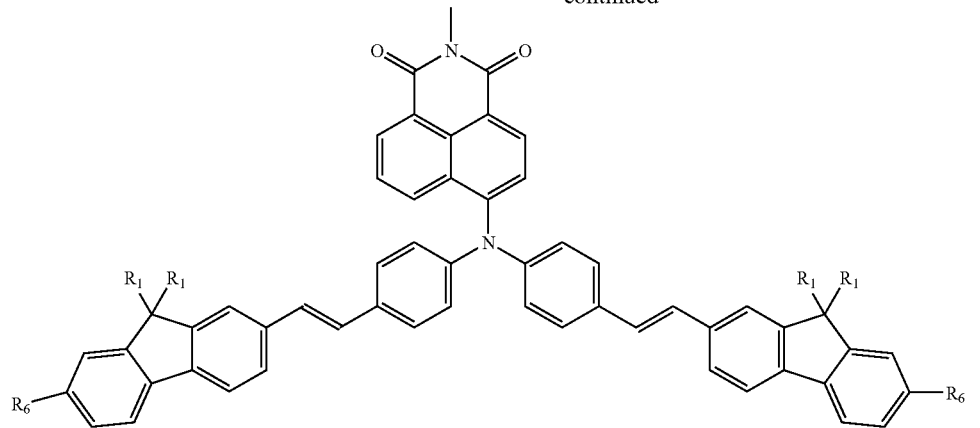
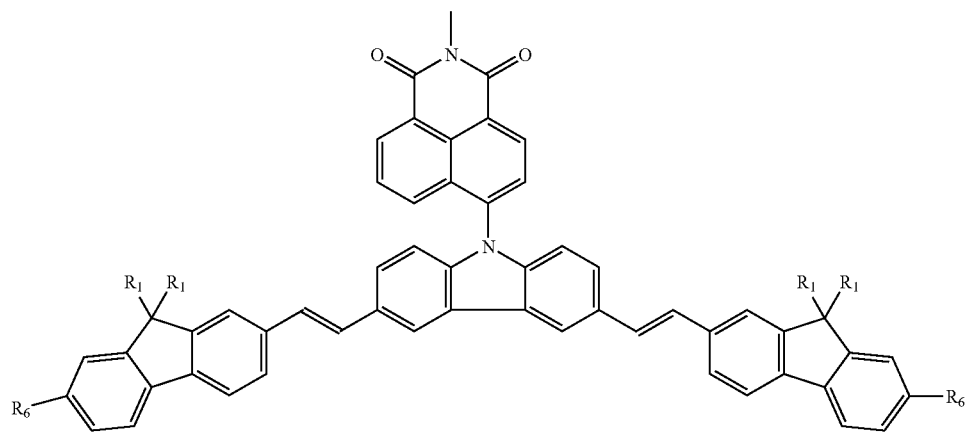
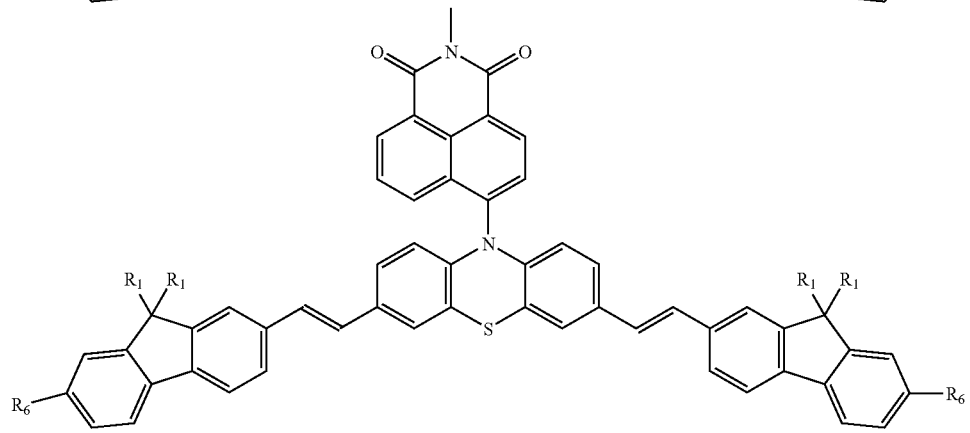
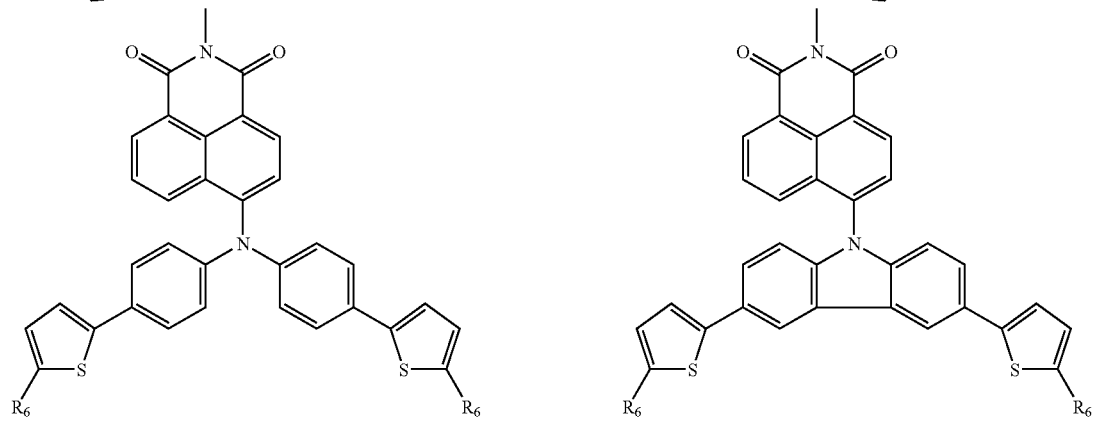

89
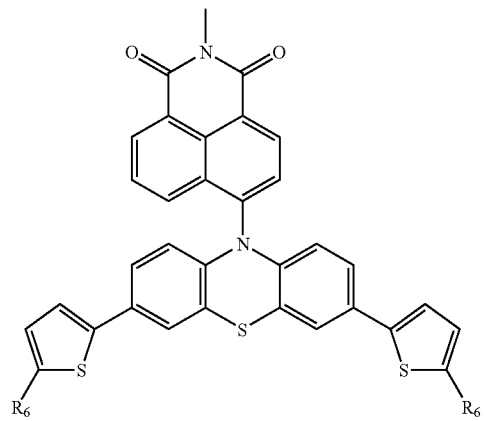
-continued
90
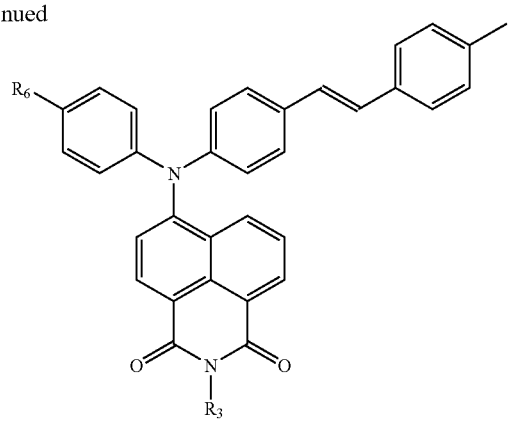
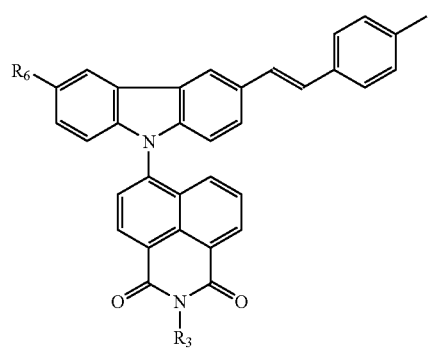
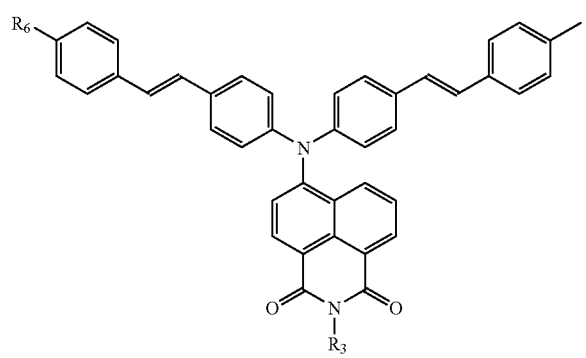
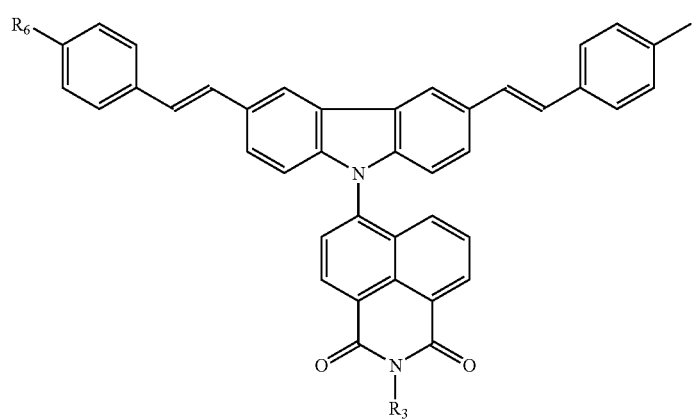

wherein R$_6$ is alkyl, phenyl, naphthyl, a phenyl or naphthyl group substituted by alkyl or alkoxy, wherein the chain lengths of the alkyl and the alkoxy are 1-18; and
type (III): Terminal group type single white electroluminescent polymeric material

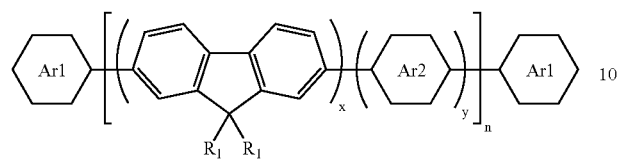

wherein: Ar1 is a naphthalimide derivative basic unit; the structure of Ar2 is the same as the Ar2 of the main chain type single white luminescent polymeric material; x and y are basic unit contents and satisfy 0<x≦1, 0<y<1, x+y=1; n=1-300;

Ar1 has one or more structures as listed below:

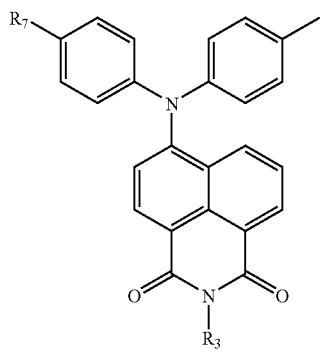

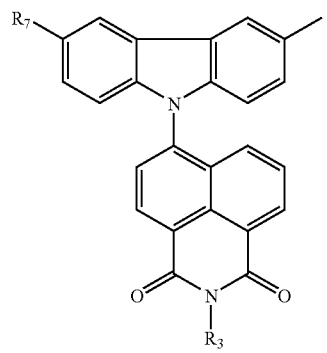

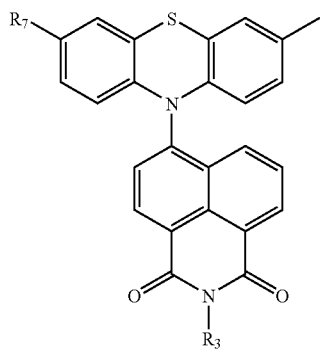

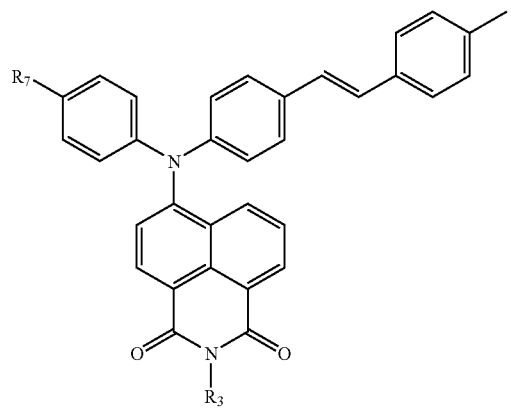

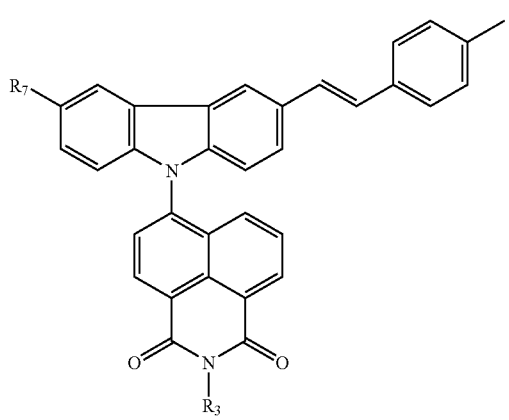

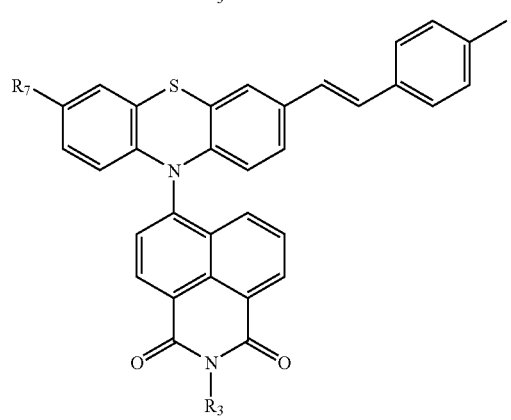

-continued
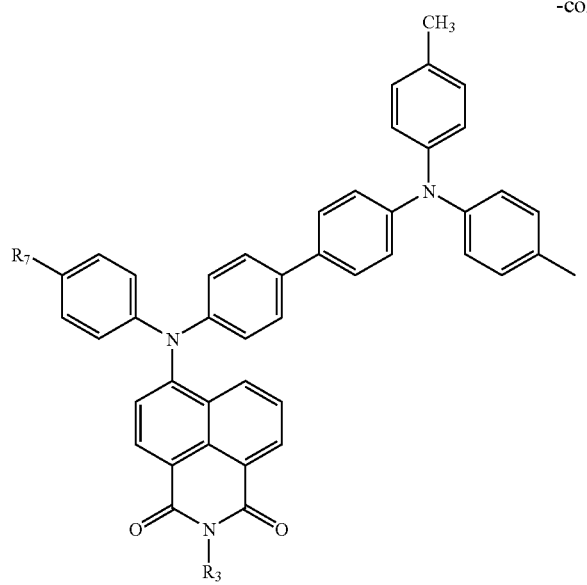
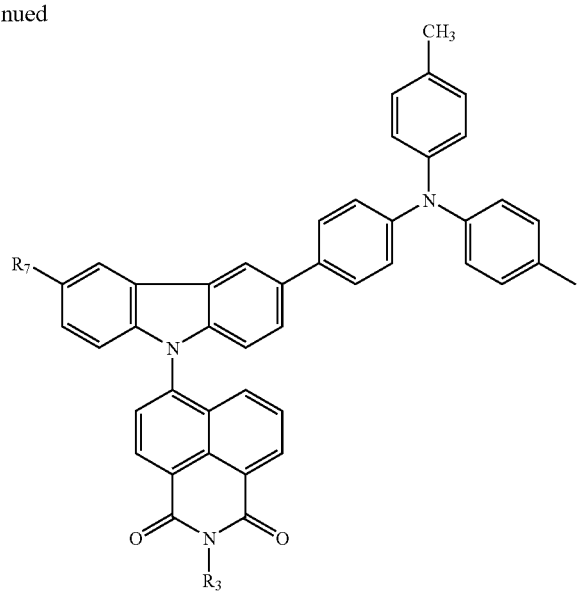
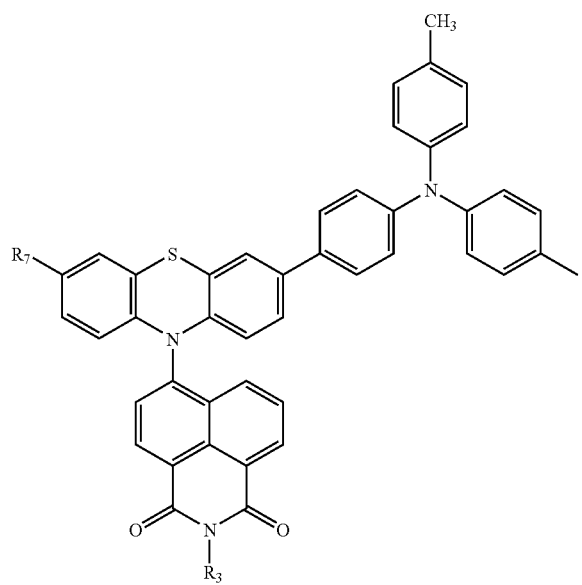
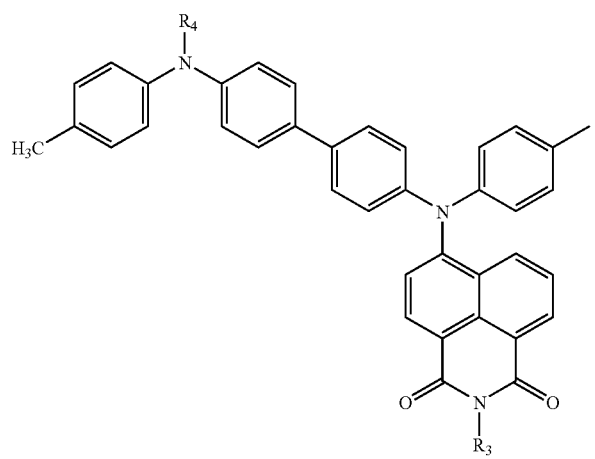
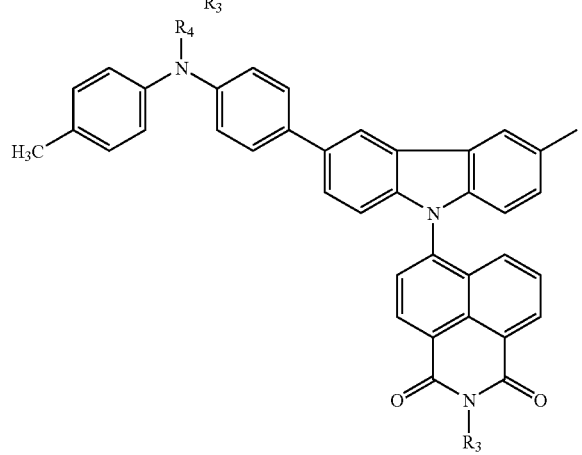
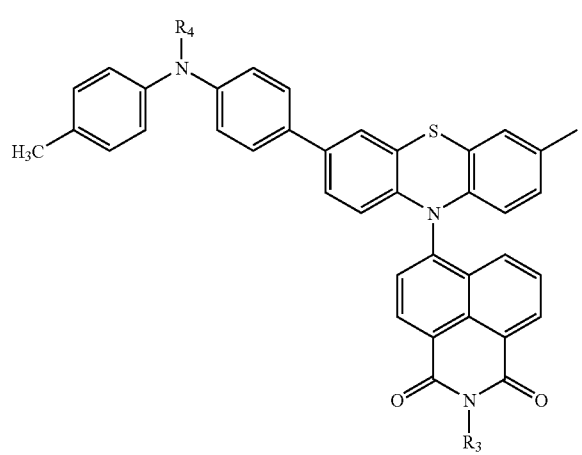

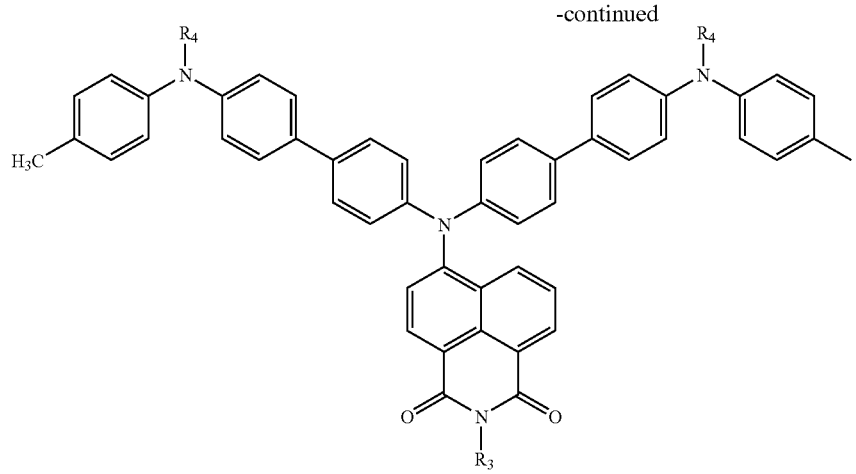
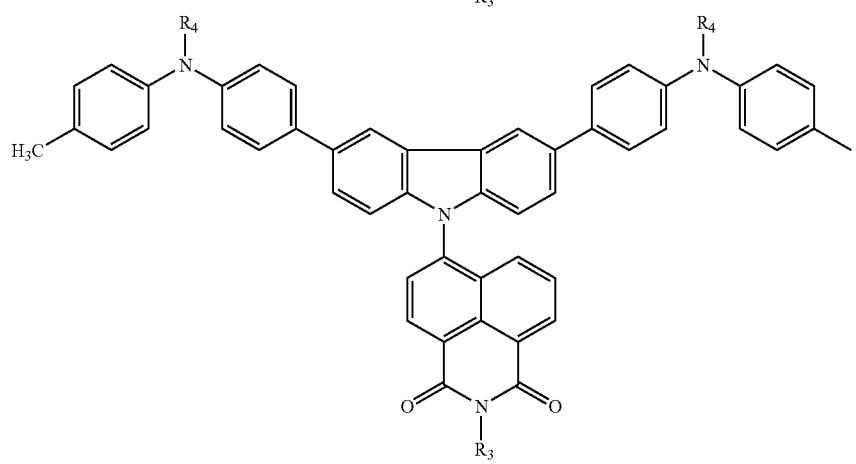
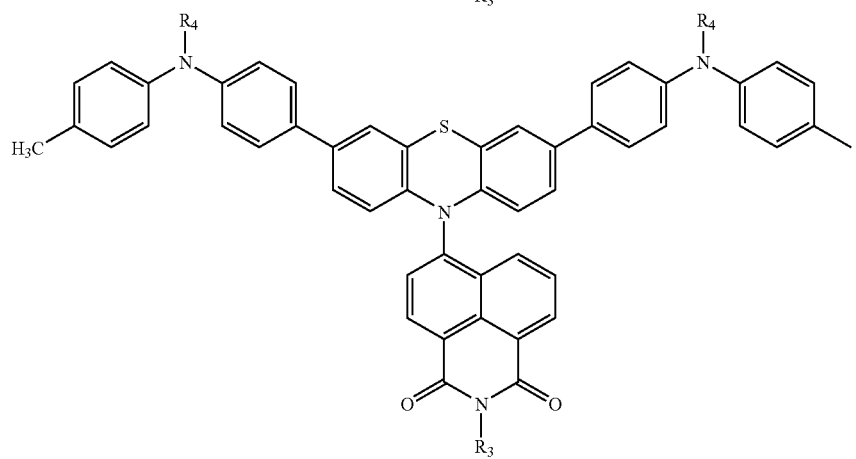
wherein R₇ is alkyl, phenyl, naphthyl, or a phenyl or naphthyl group substituted by alkyl or alkoxy; wherein the chain length of alkyl and alkoxy is 1-18.
* * * * *